United States Patent [19]

Beesmer et al.

[11] Patent Number: 5,196,872
[45] Date of Patent: Mar. 23, 1993

[54] DATA ACQUISTION AND PUPIL TRACKING APPARATUS FOR AN OPHTHALMOLOGOCIAL INSTRUMENT

[75] Inventors: Ross J. Beesmer; Tom N. Cornsweet, both of Irvine, Calif.; George Homsy, Eindhoven, Netherlands

[73] Assignee: Pulse Medical Instruments, Rockville, Md.

[21] Appl. No.: 602,136

[22] Filed: Oct. 23, 1990

Related U.S. Application Data

[62] Division of Ser. No. 448,718, Dec. 11, 1989, Pat. No. 5,042,937.

[51] Int. Cl.⁵ ............................................. A61B 3/14
[52] U.S. Cl. ................................. 351/208; 351/204; 351/211; 351/214
[58] Field of Search ............... 351/206, 211, 214, 204, 351/221

[56] References Cited

U.S. PATENT DOCUMENTS 5,042,937  8/1991  Cornsweet ........................ 351/204

Primary Examiner—Bruce Y. Arnold
Assistant Examiner—Hung Xoan Dang
Attorney, Agent, or Firm—Whitham & Marhoefer

[57] ABSTRACT

A pupil function analyzer has three major subsystem; an electro-optical system, an electronic interface system and a computer/software system. The electro-optical system can, in turn, be described in terms of three subsystems; one that delivers controlled lights to the patient's eyes, another that forms images of the two pupils on a video camera, and a third that moves the optics to maintain alignment with the patient's eyes. The electronic interface system converts signals from the video camera into digital signals to be read by the computer and also responds to the computer to move motors for the maintenance of optical alignment and also operates the light stimuli. The computer/software saves and analyzes the signals sent by the electronic interface, controls the alignment motors, and provides an operator interface, so that the operator can select tests and examine the results.

14 Claims, 46 Drawing Sheets

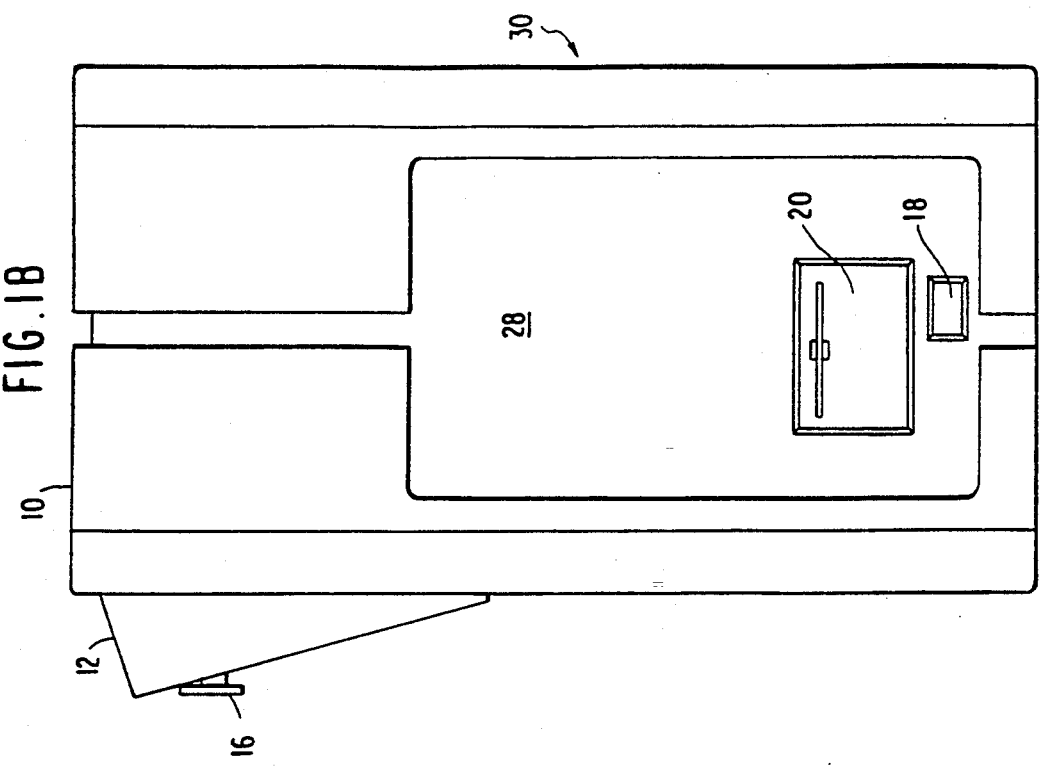
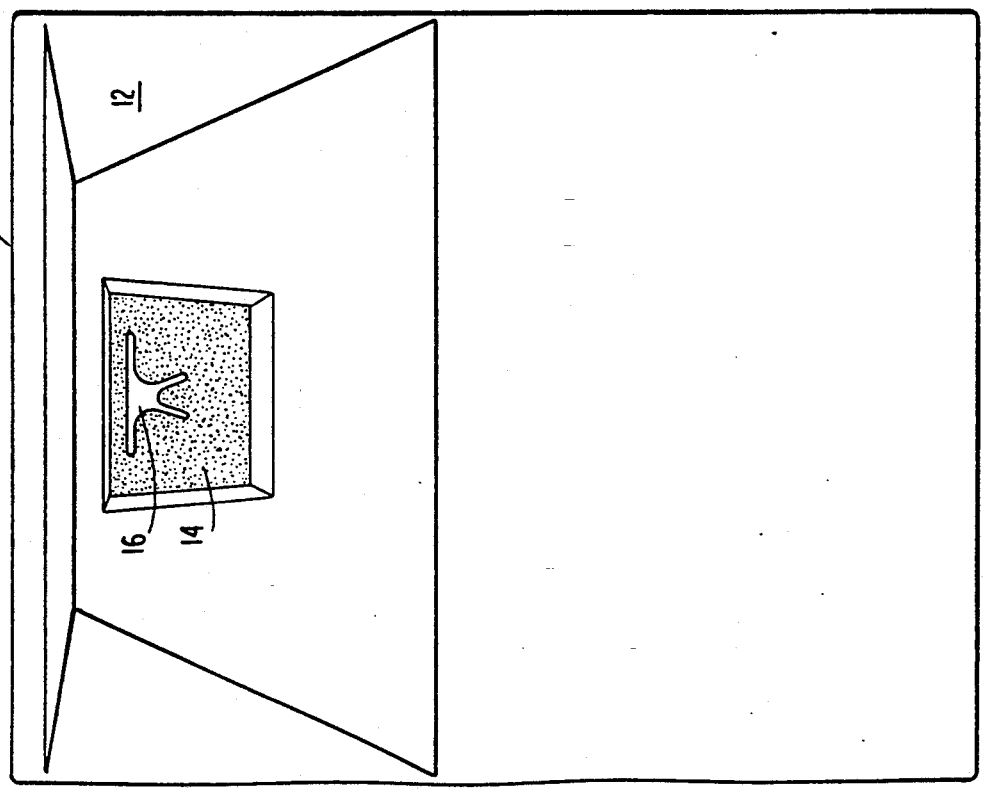

FIG. 5

| PUPIL PATHWAY ANALYZER | | PULSE MEDICAL INSTRUMENTS, INC. |
| PATIENT | TEST | LIBRARY | HELP |

DISPLAY  RUN
▶  √  TEST  NAME / STIMULUS FIELD(S)                32

ENTER PATIENT'S AGE IN YEARS:

24

7  8  9
4  5  6    OK — 46
1  2  3    CANCEL
0     DEL           44

| PUPIL PATHWAY ANALYZER | | | PULSE MEDICAL INSTRUMENTS, INC. |
| PATIENT | TEST | BEGIN | LIBRARY | HELP |

DISPLAY  RUN                                           32
▶  √  TEST  NAME / STIMULUS FIELD(S)

SCREENER /
    SWINGING IMPULSE / BOTH FULL FIELDS
    IMPULSE RESPONSE / FULL FIELD
    PERIMETRY PUPIL SIZE / FULL FIELD
    STEP RESPONSE / FULL FIELD
    COVER/UNCOVER / FULL FIELD

FIG. 7

| PUPIL PATHWAY ANALYZER | | | PULSE MEDICAL INSTRUMENTS, INC. |
| PATIENT | TEST | BEGIN | LIBRARY | HELP |

DISPLAY  RUN                                           32
▶  √  TEST  NAME / STIMULUS FIELD(S)

SCREENER /
    SWINGING IMPULSE / BOTH FULL FIELDS
    IMPULSE RESPONSE / FULL FIELD
    PERIMETRY PUPIL SIZE / FULL FIELD
    STEP RESPONSE / FULL FIELD
    COVER/UNCOVER / FULL FIELD

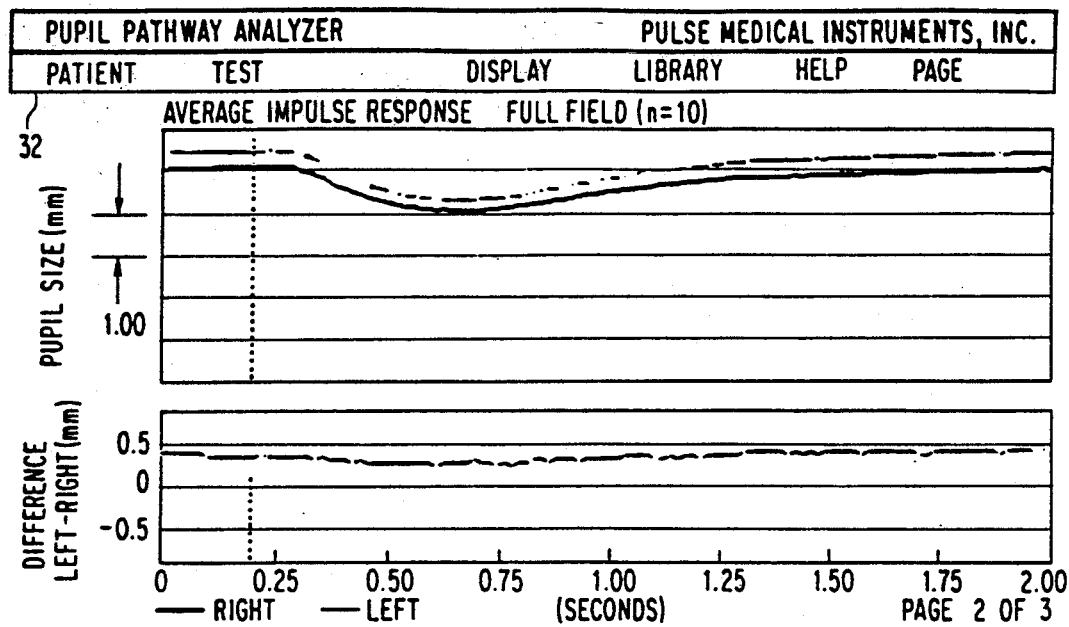

FIG. 21

| PUPIL PATHWAY ANALYZER | | | PULSE MEDICAL INSTRUMENTS, INC. | | |
|---|---|---|---|---|---|
| PATIENT | TEST | DISPLAY | LIBRARY | HELP | PAGE |

SCREENER
PERIMETRY PUPIL SIZE
SWINGING IMPULSE
SWINGING FLASHLIGHT
IMPULSE RESPONSE
STEP RESPONSE
DEPTH OF AFFERENT DEFECT
COVER / UNCOVER
HIPPUS
DEMONSTRATION
CLEAR TEST SEQUENCE

PUPIL SIZE
OF 1

| | RIGHT EYE | LEFT EYE |
|---|---|---|
| ) | 5.00 | 5.31 |

| PUPIL PATHWAY ANALYZER | | | PULSE MEDICAL INSTRUMENTS, INC. | |
|---|---|---|---|---|
| PATIENT | | LIBRARY | HELP | PAGE |

SELECT STIMULUS:

HIPPUS TEST

FULL FIELDS

TEMPORAL HEMIFIELDS

NASAL HEMIFIELDS

CUSTOMER FIELD

OK    CANCEL 32
72
76
74
PER
T EYE
5.31

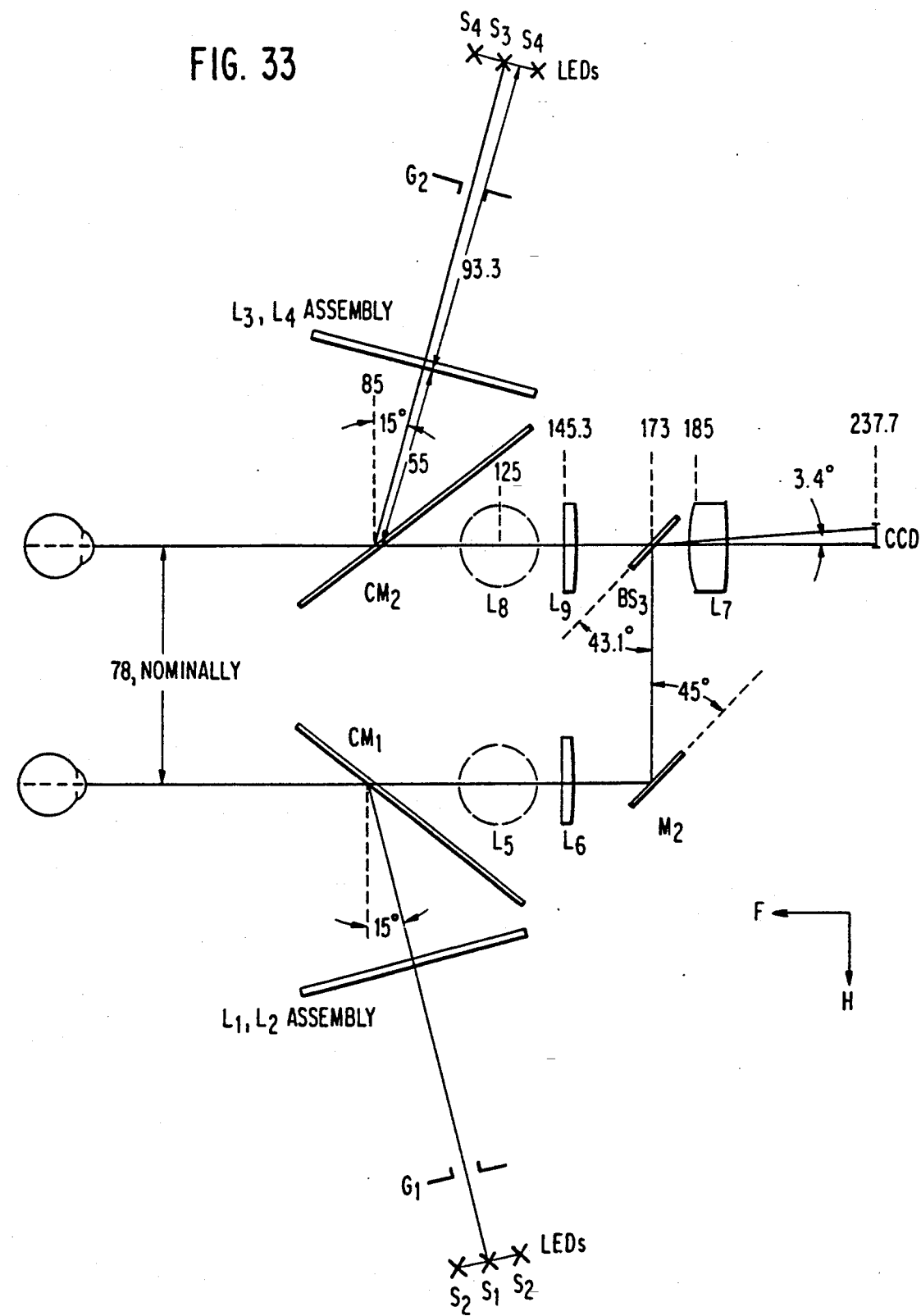

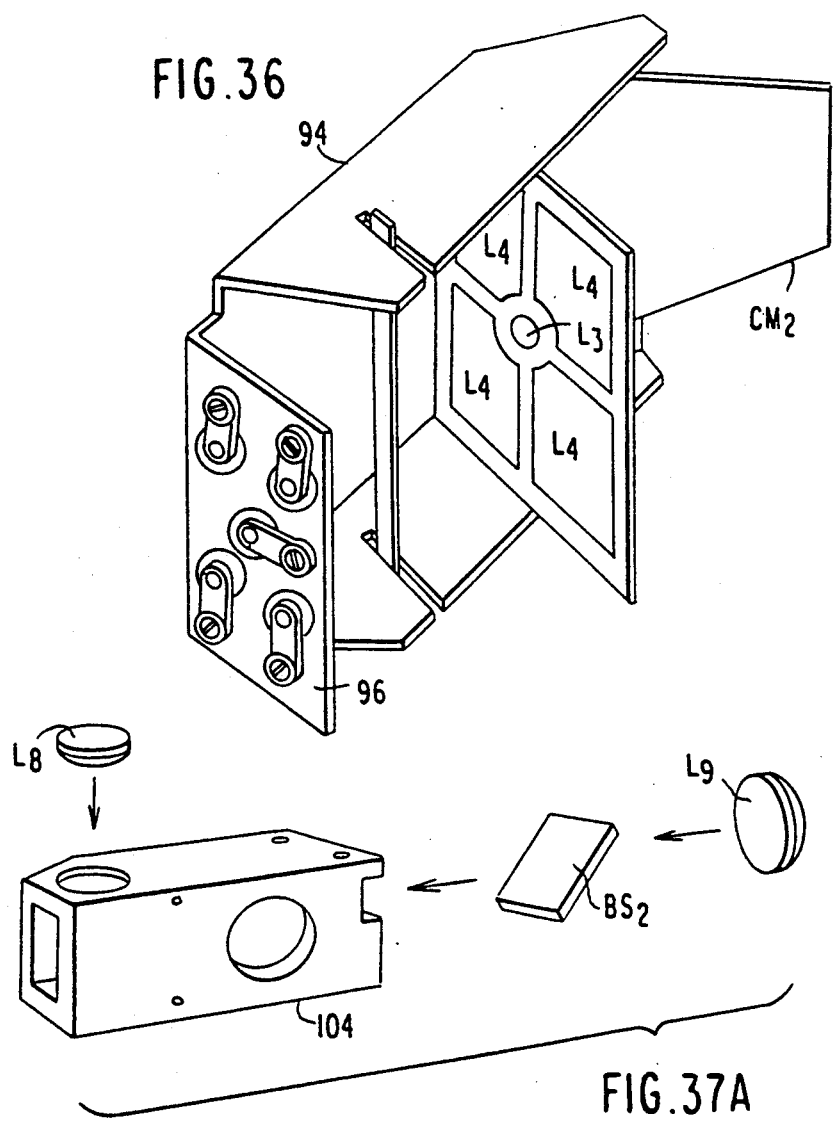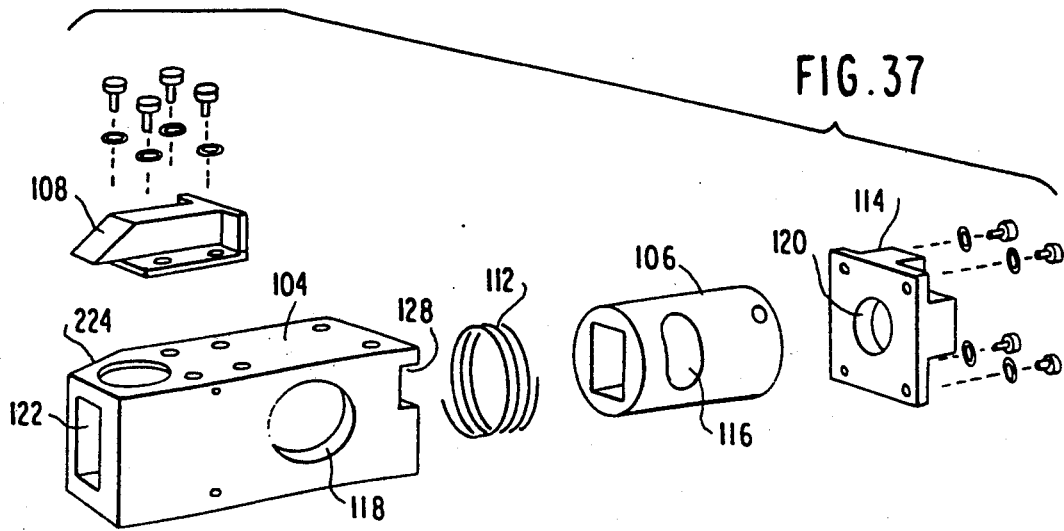

FIG. 43
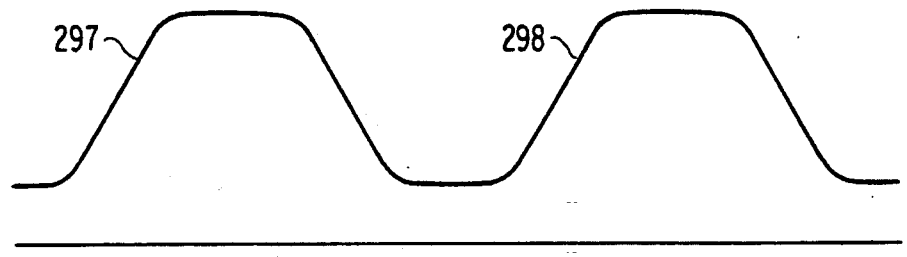
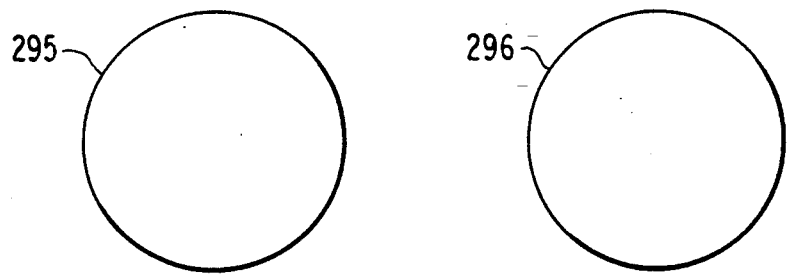
FIG. 43A
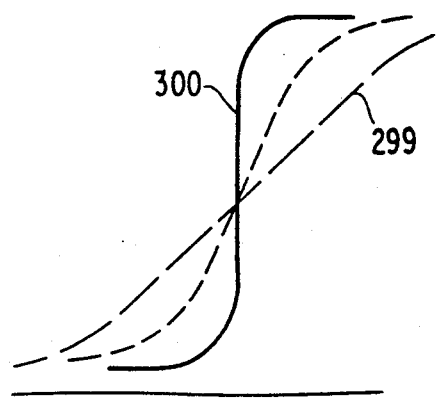

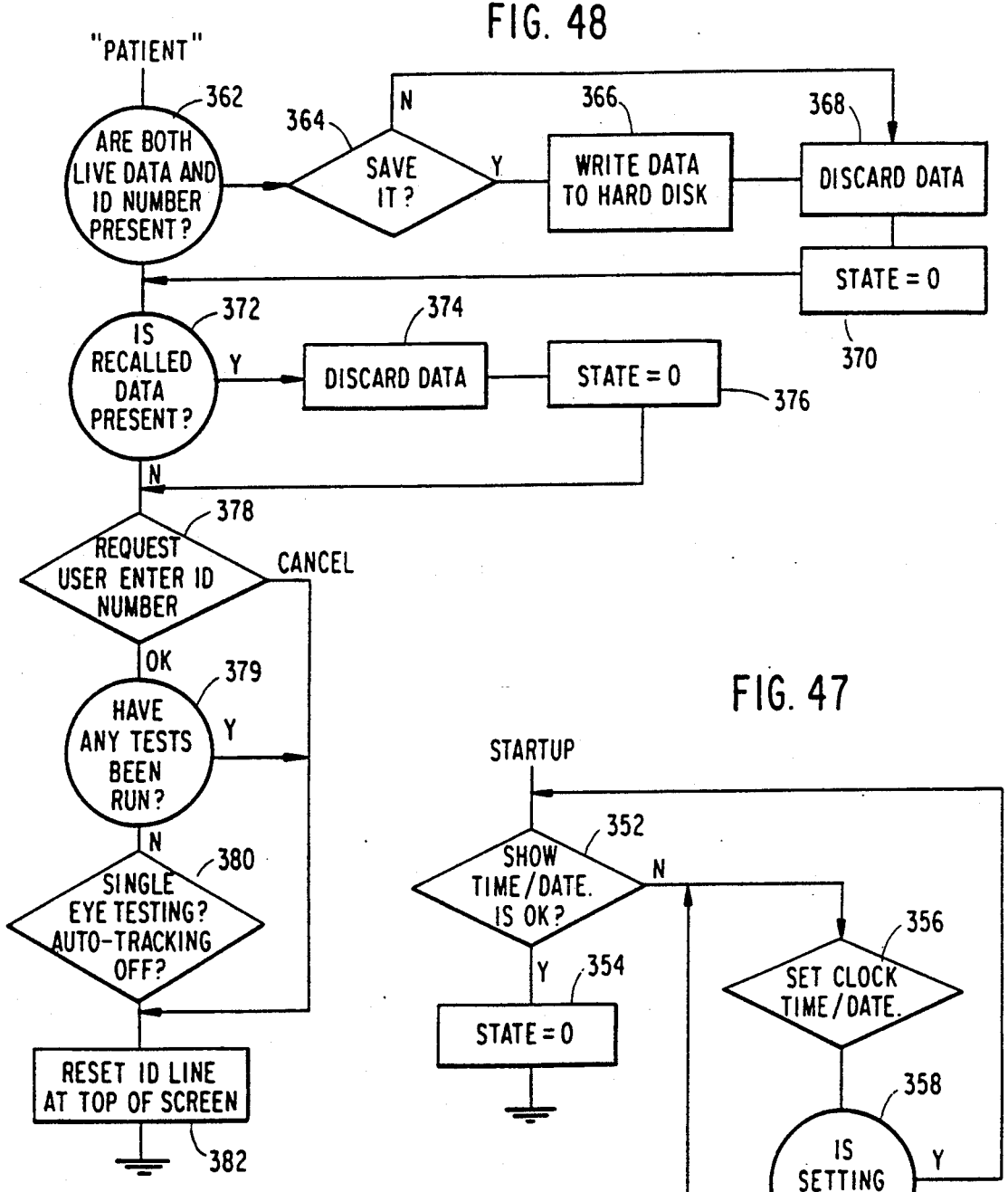

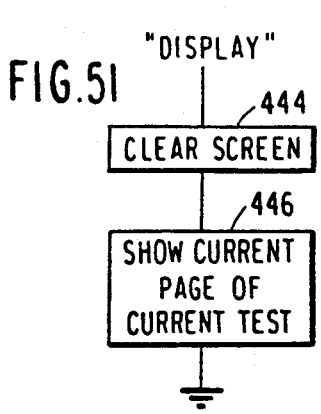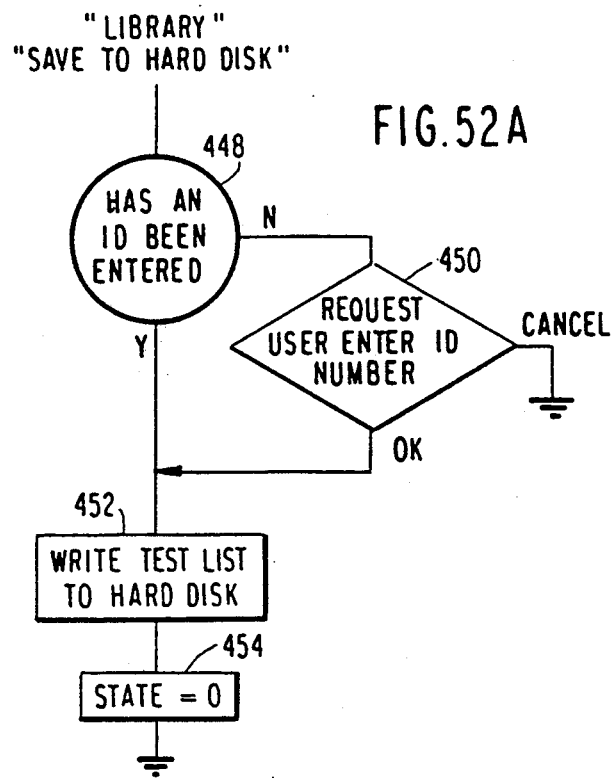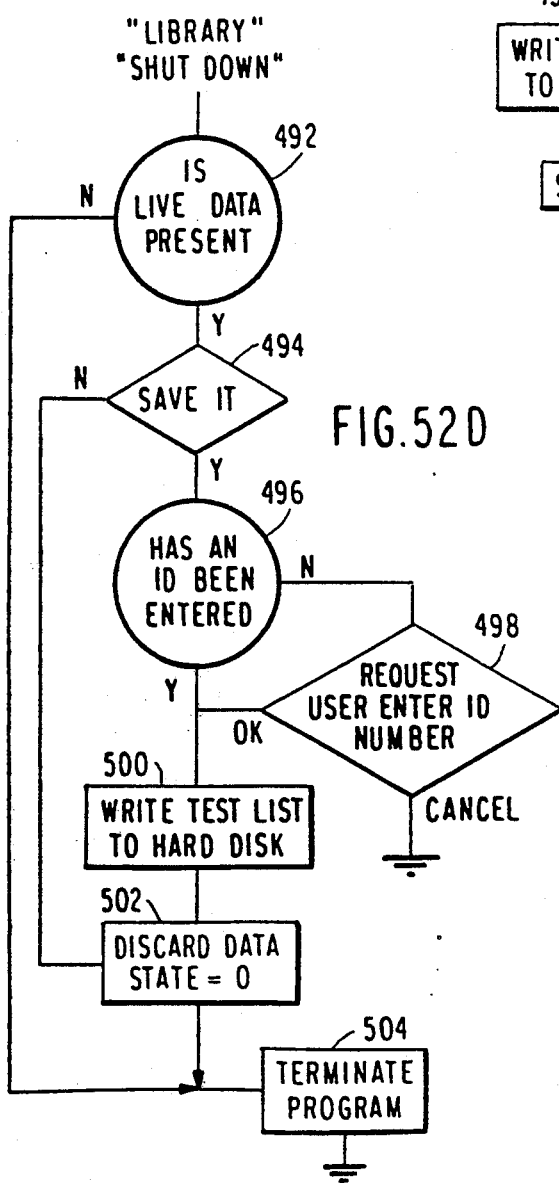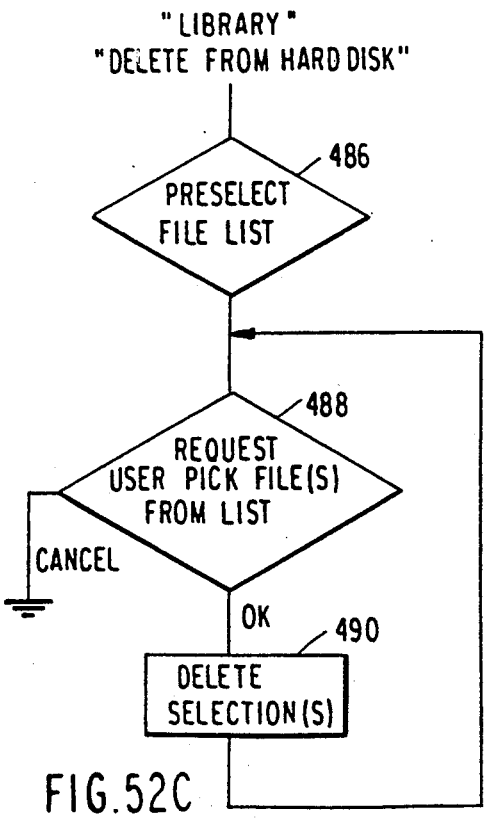

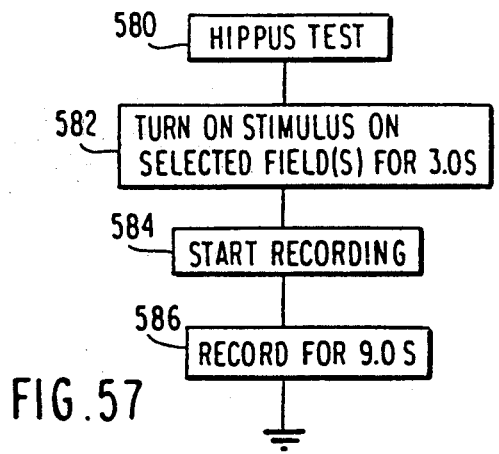
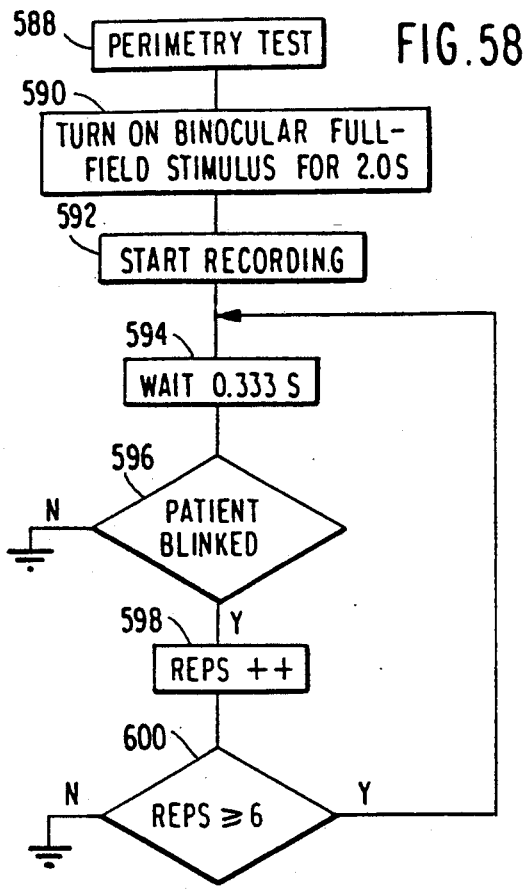
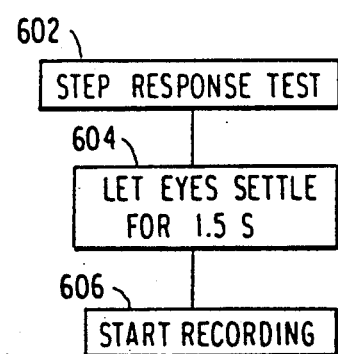
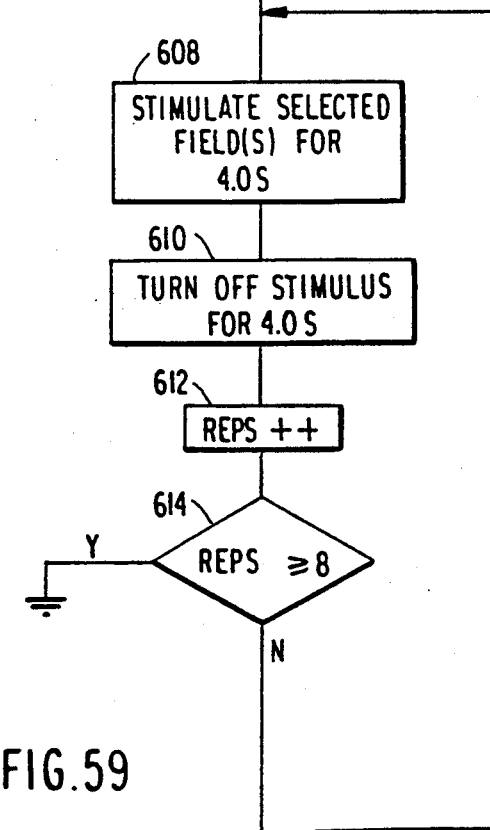
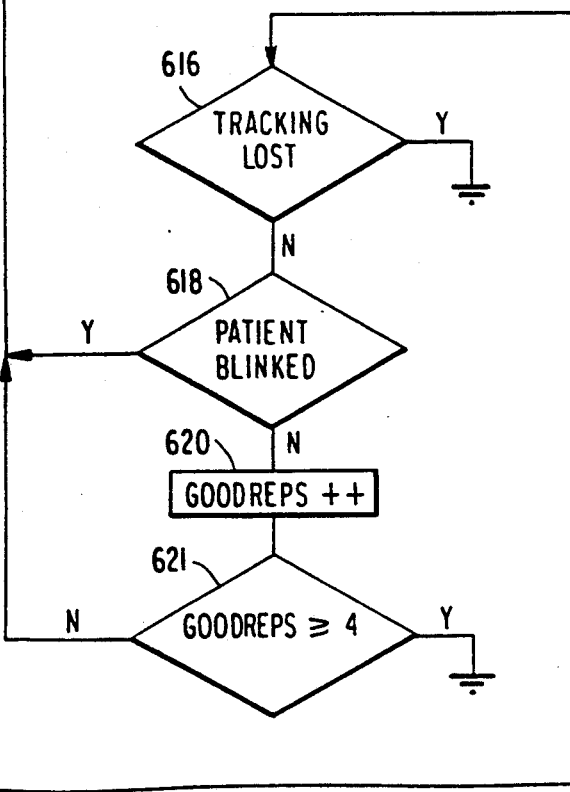

DATA ACQUISTION AND PUPIL TRACKING APPARATUS FOR AN OPHTHALMOLOGOCIAL INSTRUMENT

CROSS-REFERENCE TO RELATED APPLICATION

This application is a divisional application of copending application Ser. No. 07/448,718 filed Dec. 11, 1989, by Tom N. Cornsweet for "Optical System for an Ophthamological Instrument for Examination of Pupillary Responses", now U.S. Pat. No. 5,042,937, and assigned to a common assignee.

BACKGROUND OF THE INVENTION

1. Field of the Invention

The present invention generally relates to ophthalmological instruments and, more particularly, to a computer-controlled electro-optical instrument designed to automate and quantify clinical examination of pupillary responses and extrinsic eye muscle balance. The instant invention contemplates an automatic data acquisition and pupil tracking apparatus for such instruments.

2. Description of the Prior Art

The iris of the eye is (in humans) a ring-shaped colored muscle. The hole in the center of the iris, called the pupil, normally appears black because the surfaces behind it reflect back to an observer much less light than does the surrounding iris. When the eye is suddenly exposed to light, certain of the muscle fibers in the iris contract, causing the pupil to become smaller, or constrict. The pupils also constrict when a near object is viewed, and their diameter is also determined continuously by certain aspects of psychological state, for example, fear. Pupil diameter is also affected by the actions of many drugs, both systemic drugs and those applied directly to the eye.

The overall physiological system that controls pupil size includes many components, and because the various components may be affected in various ways by different diseases, toxins, tumors, and the like, disorders are often reflected in abnormal pupillary responses. Therefore, examination of the responses of the pupillary system is an important part of most neurological and ophthalmological medical examinations. To perform an examination of pupil responses, the physician dims the room lights, illuminates one eye and then the other with a small light, and observes the responses. This technique, even when performed by the most careful observer, lacks much in accuracy and provides no quantitative or permanent record of the results.

Various systems are known in the prior art which automate the examination of pupil function and provide a quantitative result. For example, U.S. Pat. No. 3,036,568 to Stark shows a pupillometer which monitors the response of an eye to light stimulus. An infrared light source is used to illuminate the eye. A glow lamp provides a visible light stimulus and, as a result of a constriction of the pupil, the light reflected from the iris to an infrared sensitive device varies. The output of the infrared sensitive device is supplied to a chart recorder In U.S. Pat. Nos. 3,533,683 and 3,533,684, Stark et al. show a dynamic pupillometer using a television camera system in which an infrared light source, a visual light stimulator and a television camera system are all directed at the eye of a patient. As in the previous Stark patent, the pupil contracts upon visual light stimulation thus allowing the iris to reflect more infrared light, but in this case the infrared light is detected by the camera. The instantaneous pupil size is determined by counting television scan lines.

Other examples of automated pupil function examination systems are disclosed in U.S. Pat. No. 3,966,310 to Larson which shows a hand held pupillometer and U.S. Pat. No. 4,755,043 to Carter which shows a digital portable scanning pupillometer.

It is also known to automate other eye examination procedures. For example, U.S. Pat. No. 4,370,033 to Kani et al. discloses an eyeball examining device which is used to analyze the eye retina. A visible light beam is projected onto any area of the eye retina, and a magnified image of the eye retina is displayed on an infrared television monitor. U.S. Pat. No. 4,618,230 to Ens et al. discloses a computer controlled visual stimulator that obtains an electroretinogram by an automated process.

While there exist several systems that address the problem of automating the examination of the pupil function, the scope of the examination is relatively limited and requires a highly skilled person to operate the system and analyze the results.

SUMMARY OF THE INVENTION

It is therefore a general object of the present invention to provide a highly automated, multifunction system for the quantitative examination of pupil function.

It is another more specific object of the invention to provide an automatic data acquisition and pupil tracking apparatus for a pupil function analyzer.

It is a further object of the invention to provide an automated binocular pupil function analyzer which independently measures both pupil diameters.

It is yet another object of the invention to provide an automated pupil function analyzer which both tracks and focuses images of a patient's pupils.

The pupil function analyzer according to the invention has three major subsystems; an electro-optical system, an electronic interface system and a computer/software system. The electro-optical system can, in turn, be described in terms of three subsystems; one that delivers controlled lights to the patient's eyes, another that forms images of the two pupils on a video camera, and a third that moves the optics to maintain alignment with the patient's eyes. The electronic interface system converts signals from the video camera into digital signals to be read by the computer and also responds to the computer to energize LEDs for optical stimuli and to move motors for the maintenance of optical alignment. The computer/software saves and analyzes the signals sent by the electronic interface, controls the alignment motors, and provides an operator interface, so that the operator can select tests and examine the results.

The operator selects a desired test or set of tests from a menu displayed on a display screen, such as a CRT. The patient then places his or her head in a headrest, and as soon as the operator presses any alignment arrow with the light pen, an image of the region of the patient's corresponding eye appears on the display screen. The operator uses a control device, such as a light pen which cooperates with the display screen, to move the image of one eye until it is roughly centered on a crosshair provided for the purpose. The process is repeated for the other eye. The operator then presses a start button, and the test proceeds automatically. During the test, the instrument automatically aligns the optics precisely on both eyes and maintains alignment even if the patient's eyes move, introduces lights into the eyes according to the sequence selected by the operator, measures the diameters and the positions of both pupils, and saves all the measurements. When the test is complete, a tone sounds indicating completion of the test and that the patient may move away from the instrument, and the operator selects the next step from a menu. This step can be to display any or all results, to print the results, and/or save the results on floppy disk for storage in the patient's file.

BRIEF DESCRIPTION OF THE DRAWINGS

The foregoing and other objects, aspects and advantages will be better understood from the following detailed description of a preferred embodiment of the invention with reference to the drawings, in which:

FIGS. 1A and 1B are, respectively, a patient elevation view and a side view of the basic pupil function analyzer according to the invention;

FIG. 3 illustrates an initial display screen which is displayed when the instrument is first turned on;

FIG. 5 illustrates a data entry screen for entering a patient's age before beginning a test;

FIG. 6 illustrates an initial screen showing the test which has been selected;

FIG. 7 illustrates the screen of FIG. 6 in which the BEGIN command has been selected;

FIG. 18 illustrates the second of the three data screens for the impulse response test;

FIG. 19 illustrates the third of the three data screens for the impulse response test;

FIG. 20 illustrates the data screen for the perimetry pupil size test;

FIG. 21 illustrates the overlying pull down window which is displayed when the TEST command is selected;

FIG. 22 illustrates the dialog box for configuring stimulus fields;

FIG. 33 is a schematic diagram showing the optical system viewed from the top;

FIG. 36 is a perspective view of the left light box assembly;

FIG. 37 is an exploded view of the left scope assembly;

FIG. 37A is an exploded view of the left scope box assembly;

FIG. 43 is a graphical representation of the analog video signal produced when a patient's pupils are scanned;

FIG. 43A is an enlarged graphical representation of a leading edge of the video signal;

FIGS. 47 to 54 are the flow diagrams showing the logic of the software which form the menu and dialog box interface for the system in which FIG. 47 is the flow diagram for the startup procedure, FIG. 48 is the flow diagram for the PATIENT command selected from the command bar of the display, FIG. 49 is the flow diagram showing the logic of the TEST command selected from the command bar of the display, FIG. 50 is the flow diagram showing the logic of the BEGIN command selected from the command bar of the display, FIG. 51 is the flow diagram showing the logic of the DISPLAY command selected from the command bar of the display, FIGS. 52A, 52B, 52C, and 52D are the flow diagrams showing the logic of the LIBRARY command selected from the command bar of the display, FIG. 53 is the flow diagram showing the logic of the HELP command selected from the command bar of the display, and FIG. 54 is the flow diagram showing the logic of the PAGE command selected from the command bar of the display; and FIGS. 55 to 64 are flow diagrams showing the logic for the several tests performed in which FIG. 55 is the flow diagram for the swinging flashlight test, FIG. 56 is the flow diagram for the swinging impulse test, FIG. 57 is the flow diagram for the hippus test, FIG. 58 is the flow diagram for the perimetry test, FIG. 59 is the flow diagram for the step response test, FIG. 60 is the flow diagram for the impulse test, FIGS. 61A and 61B, taken together, are the flow diagram for the relative afferent defect test, FIG. 62 is the flow diagram for the cover/uncover test, FIG. 63 is the screener flow diagram, and FIG. 64 is the demo flow diagram.

DETAILED DESCRIPTION OF A PREFERRED EMBODIMENT OF THE INVENTION

Figure 2:
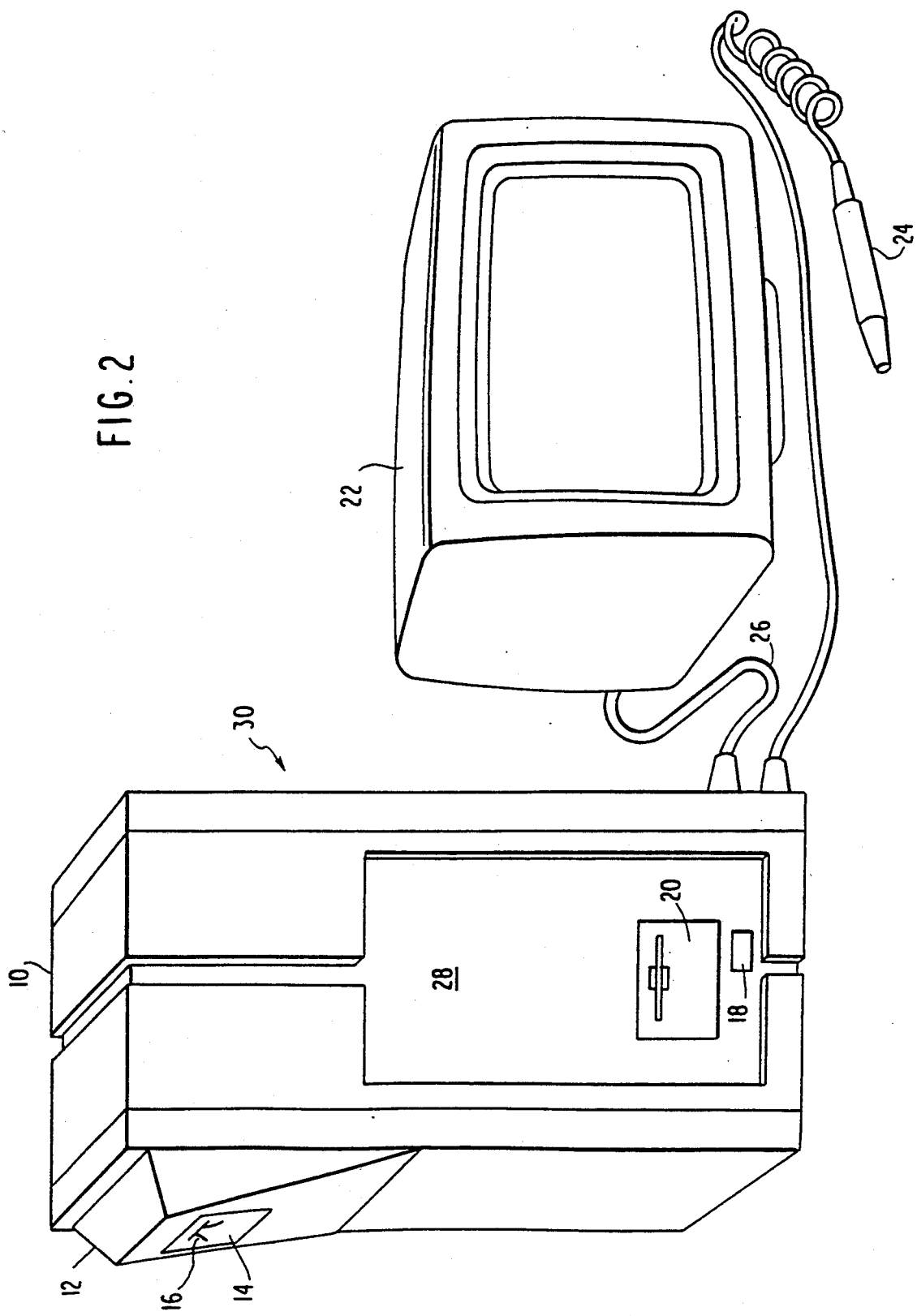
FIG. 2 is a perspective view of the pupil function analyzer showing an attached operator display monitor and light pen.

Referring now to the drawings, and more particularly to FIGS. 1A and 1B, there are shown, respectively, an elevation view on the patient's side of the instrument and a side view on the operator's side of the instrument. The basic instrument is housed in a compact case 10 having a small footprint so that it may be placed on a desktop. On the patient's side, FIG. 1A, there is a slight protrusion 12 with an aperture 14 into which the patient is instructed to gaze. The patient's head is positioned by a nose and brow piece 16 suspended within the aperture 14. On the operator's side, FIG. 1B, there is an on-off switch 18 and a floppy diskette drive 20. While data for each patient will normally be printed on paper by a printer (not shown) attached to the system, data may also be stored on a diskette for storage in a patient's folder.

A separate display 22 and light pen 24, as shown in FIG. 2, is provided for the operator of the system. The display may be any display compatible with the NTSC television standard and capable of supporting overlaid computer generated graphics. In a preferred embodiment, the display is a conventional IBM Personal Computer compatible computer monitor supporting both the color graphics adapter (CGA) and enhanced graphics adapter (EGA) standards, the former being compatible with the NTSC television standard. The display 22 is connected to the instrument by a cable 26 allowing the display to be placed at a convenient location for use by the operator. It will be understood, however, that the display 22 may be made integral with the instrument. For example, the display could be incorporated into the area 28 (shown in FIG. 1B) on the side of the case 10 or into the back of the case as generally indicated by the reference numeral 30.

The light pen 24 is the operator's input device. The instrument software generates screens or menus on the display 22 from which the operator can select various choices or into which the operator can input data by means of the light pen 24. For example, when numeric data, such as a patient's identification number (ID), needs to be input, a numeric keypad is displayed and the operator simply selects the numbers on the keypad using the light pen. In the same manner, if it is desired to input alphabetic data, a keyboard may be displayed. As will be described in more detail hereinafter, the light pen is also used for moving images of the patient's eyes so that those images are aligned with cross hairs on the display screen.

It will be understood by those skilled in the art that various operator input devices may be used in place of the light pen 24 and display 22. For example, a hardware keyboard and keypad could be used to input alphanumeric data. A hardware cursor positioning device such as a mouse, a track ball or a joy stick could be used to position the images of the patient's eyes on the cross hairs. While such hardware is conventional and well known, the approach taken in the design of the preferred embodiment of the invention is make the instrument as simple to use by an untrained operator as possible. The light pen 24 has been found to be a very easy to use input device which is easily mastered without intimidating the user. Of course, the light pen itself could be replaced by the operator's finger if the display 22 incorporates a touchscreen.

The approach taken in the design of the software for the instrument is to provide a "point-and-shoot" graphical user interface (GUI) with dialog boxes and pull down windows as pioneered by the Xeroxo Star computer and made popular by the Appleo Macintosh!! computer. This is best illustrated by way of example.

Figure 3:
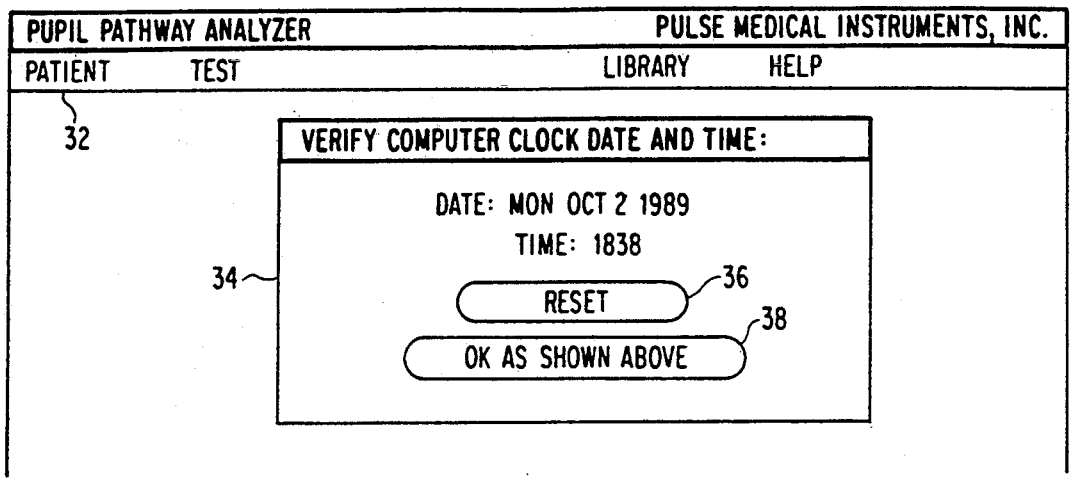

When the instrument is first turned on, the screen shown in FIG. 3 is displayed. It will be observed that this screen includes a command bar 32 along the top in which are displayed the commands which are currently active in the system. This initial screen displays a dialog box 34 which requests the operator to verify the computer clock data and time and displays the date and time with two "buttons". These are a RESET button 36 and an OK button 38, either of which the operator can select with the light pen 24. It is important to have the correct date and time because patient data is date stamped.

Figure 4:
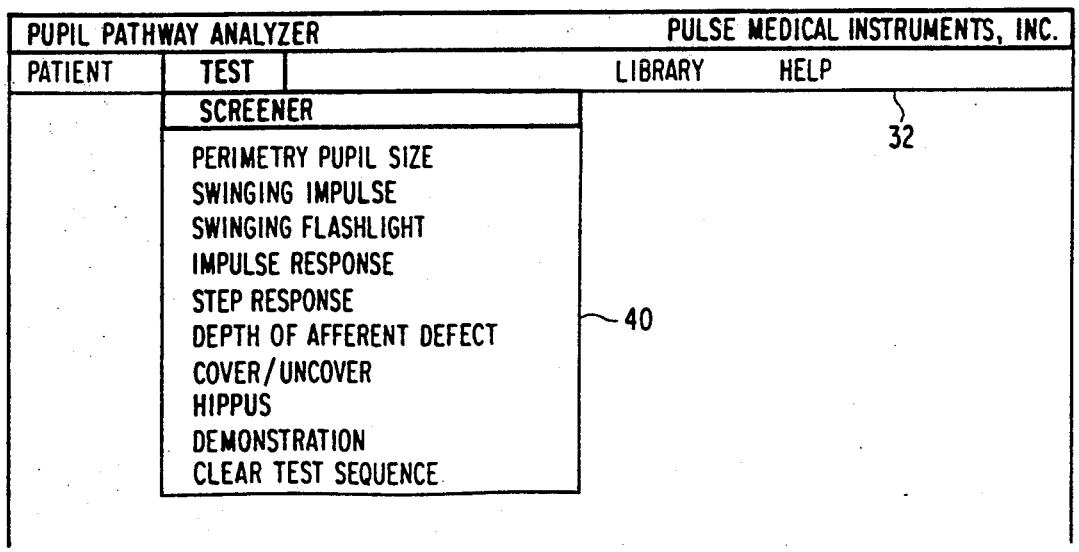
FIG. 4 illustrates a pull down menu which is displayed when the TEST command is selected from the command bar.

Assuming the operator selects the OK button 38, the dialog box 34 will disappear. The operator may next want to test a patient, and this is done by selecting TEST in the command bar 32 causing a pull down window 40 to be displayed as shown in FIG. 4. This pull down window provides a menu of several tests from which the operator may choose. In the case illustrated in FIG. 4 the screener test has been selected, as indicated by the reverse highlight, by sliding the light pen 24 down to that part of the pull down window and releasing the select button on the light pen. As will described in more detail, the screener test is actually a plurality of tests selected to generate a variety of data from a patient. In the preferred embodiment, the screener test may include, for example, an impulse test, a swinging impulse test, a perimetry pupil size test, and a cover/uncover test. It is, of course, possible for the physician who uses the instrument to specify a different combination of tests for the screener test.

When the screener test has been selected, the dialog box 42 is displayed as shown in FIG. 5. This dialog box requests the operator to enter the patient's age and displays a numeric keypad for that purpose. In the case illustrated, the operator has used the light pen 24 to select the numbers "2" and "4", and the age "24" is displayed at the top of the keypad. If an error has been made, the operator can select the CANCEL button 44, but in this case, the OK button 46 has been selected as indicated by the reverse highlight.

Once the patient's age has been entered, the screen shown in FIG. 6 is displayed. This screen indicates that for this particular screener test, the swinging impulse test, the impulse response test, the perimetry pupil size test, step response test, and the cover/uncover test.

FIG. 7 is similar to FIG. 6 except that the operator has now selected the BEGIN command from the command bar 32, as indicated by the reverse highlight. This causes the screen in FIG. 8 to be displayed. This screen includes a pair of cross hairs 48 and 50. Below the cross hairs are a pair of cursor pads 52 and 54, respectively, and between the cursor pads there is displayed an ALIGNED button 56.

Figure 8:
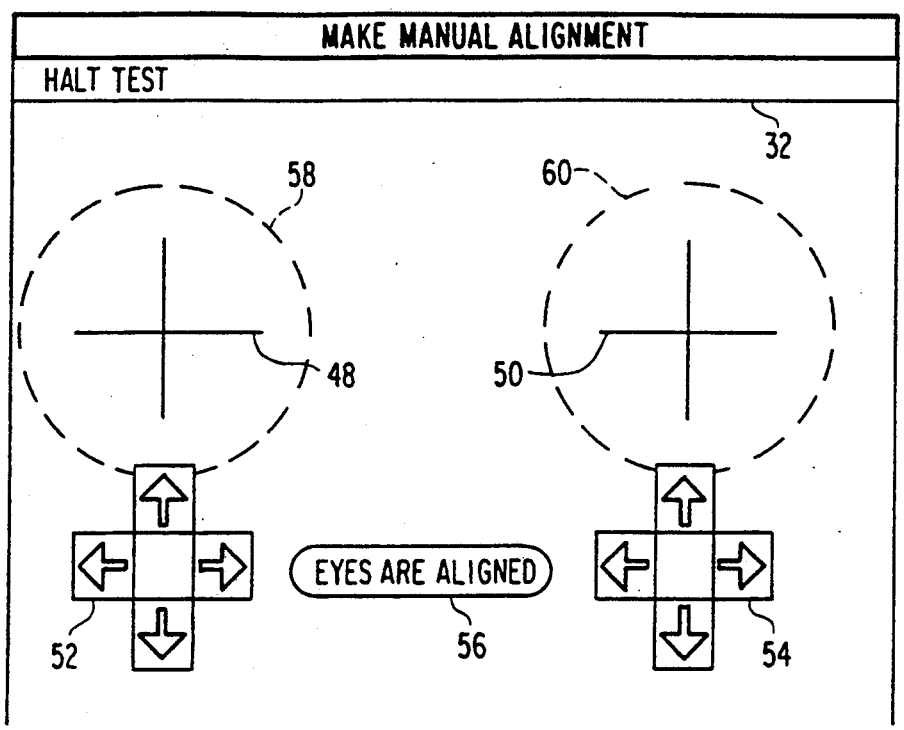
FIG. 8 illustrates the video screen used to align the images of the patient's eyes prior to the test being run.

While not immediately apparent from the screens shown in FIGS. 7 and 8, the protocol of the display changes when switching from the screen of FIG. 7 to the screen of FIG. 8. Up through the screen shown in FIG. 7, the display is in enhanced graphics (EGA) mode, but the screen in FIG. 8 is in color graphics (CGA) mode. EGA mode is a higher resolution mode and is preferred for displaying text and graphics data. CGA mode is a lower resolution mode, as may be observed by comparing the resolution of the text in the command bars 32 in FIGS. 7 and 8, but its line and field frequencies are compatible with the NTSC television standard. This mode is required for displaying images of the patient's eyes, and particularly the pupils. It will of course be understood that other high resolution display protocols, such as video graphics array (VGA) or one of its higher resolution variants, can be used for the display of text and graphics data rather than the EGA standard. If a lower resolution display can be tolerated, it is possible to use the CGA standard for all displays. It will also be understood that the NTSC standard, which is the standard in the United States, may be replaced by the PAL standard, which is the standard from much of Europe, or another video standard. Of course, it is understood that the display 22 used should be compatible with the protocol(s) adopted and this is readily accomplished with one of the many multi-sync monitors currently on the market.

Using the screen shown in FIG. 8, the operator first uses the cursor pads 52 and 54 to align the images of the patient's pupils on the cross hairs 48 and 50. Thus, if the image of the patient's right eye (left eye in the display) needs to be moved to the right to center it on the cross hairs 48, the operator selects the right pointing arrow in the cursor pad 52 with the light pen 24. Left and up and down motions of the images are accomplished in a similar manner. Once the images are roughly centered on the cross hairs 48 and 52, the operator selects the ALIGNED button 56, and at that point the instrument begins to automatically track the patient's eyes, holding their images centered in the cross hairs 48 and 50. In addition, when the ALIGNED button 56 is selected, the button 56, the cross hairs 48 and 50 and the two cursor pads 52 and 54 are removed from the display screen as they are no longer needed.

In FIG. 8, the patient's pupils 58 and 60 are indicated in dotted line as centered on the cross hairs 48 and 50, respectively. At this point, it should be observed that the pupils are magnified many times their actual size and displaced close to one another, occupying a large portion of the display screen. This allows the operator to observe with considerable precision the reactions of the pupils to various stimuli during a test. If the operator is a physician, this observed behavior will be of considerable value, providing a useful supplement to the data later displayed on the screen and printed.

Figure 9:
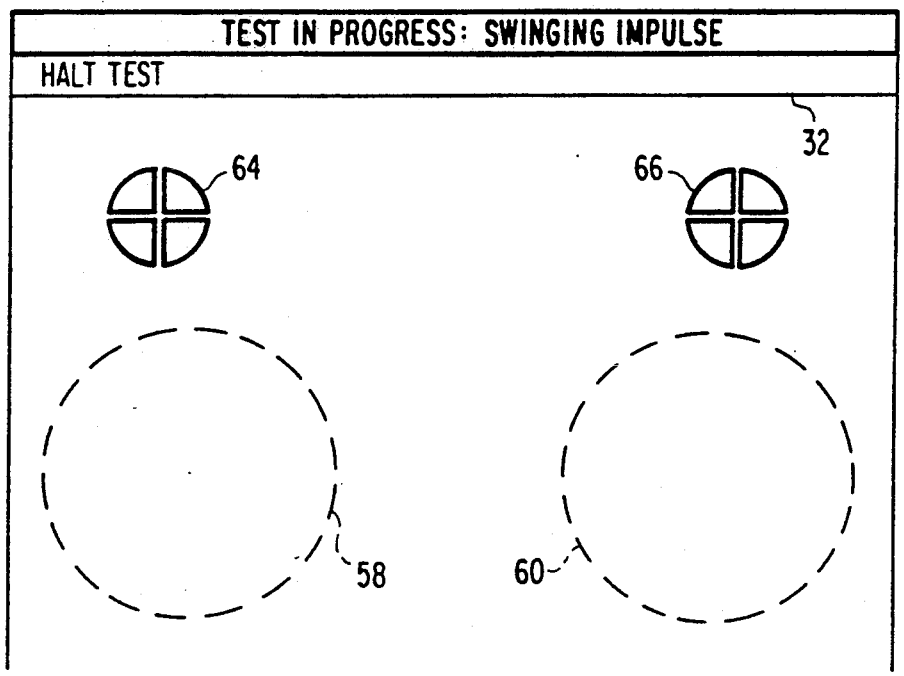
FIG. 9 illustrates the video screen during the swinging impulse test.

Beginning in FIG. 9, the instrument automatically begins the test(s) which have been selected. In FIG. 9, a message bar 62 is superposed above the command bar 32 and informs the operator that the swinging impulse test is in progress. The command bar includes only one command that the operator can select, and that is the HALT command. The images of the patient's pupils are shown in dotted line 58 and 60, and above them there are two circles 64 and 66 divided into four quadrants each. These two circles are used to indicate to the operator the nature of the stimulus being provided to each of the patient's eyes. For example., in the swinging impulse test, the circles would alternately flash, simulating a swinging light.

Figure 10:
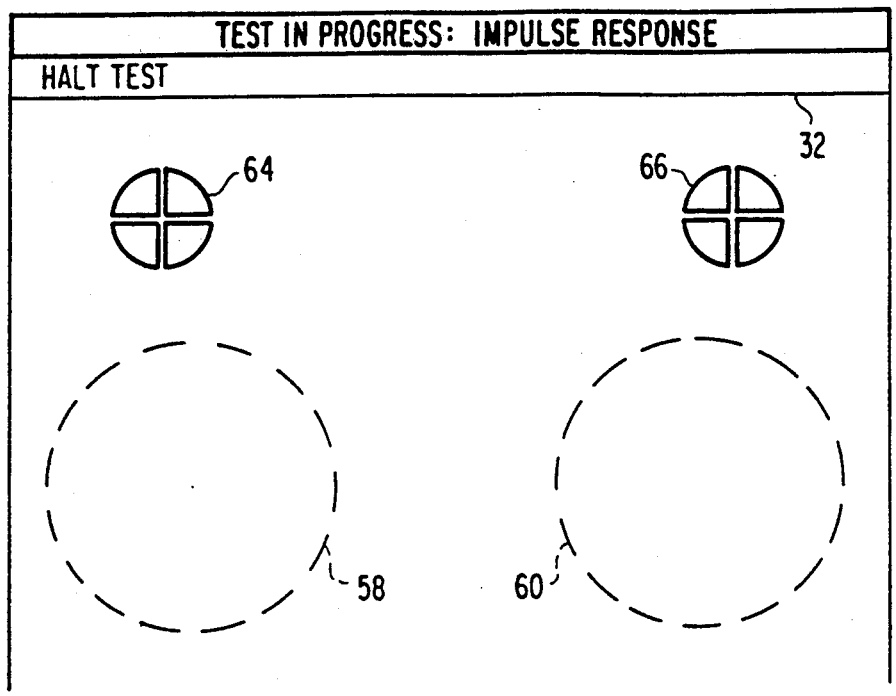
FIG. 10 illustrates the video screen during the impulse test.

The next test is the impulse response test as indicated by the message bar 62 in the screen illustrated in FIG. 10. In this case the two circles 64 and 66 would flash simultaneously.

Figure 11:
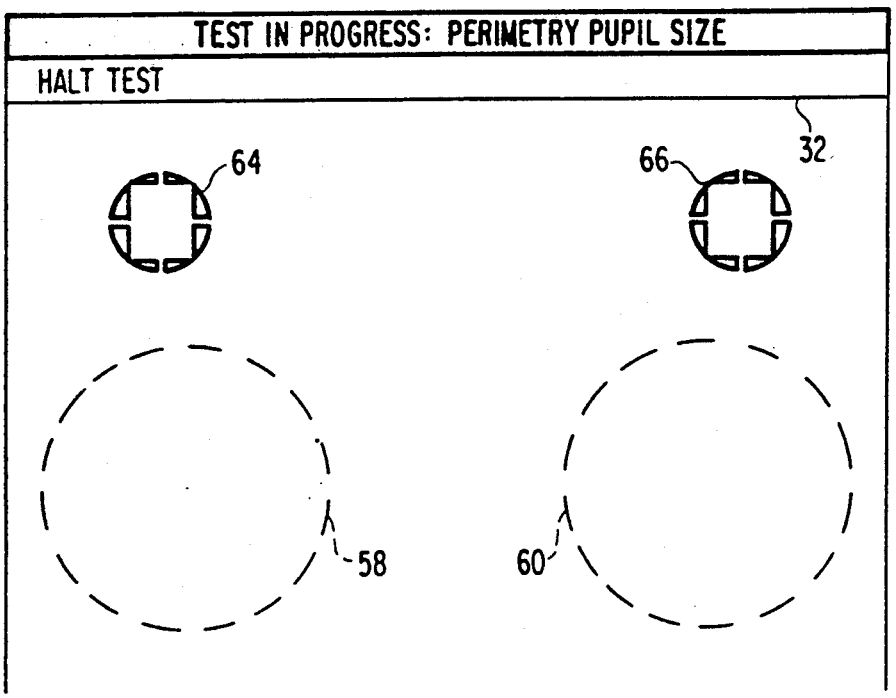
FIG. 11 illustrates the video screen during the perimetry pupil size test.

The next test in the example being described is the perimetry pupil size test as indicated by the message bar 62 in the screen illustrated in Figure 11. In this test, all four quadrants of the circles 64 and 66 are on. This is indicated by the bright squares superimposed on the circles 64 and 66. This also illustrates how the circles 64 and 66 appear in the previous two tests except that the bright squares flash in a prescribed manner rather than being on for the duration of the test. In addition, it should be understood that the squares are themselves composed of four quadrants, and it is possible to design the tests so that only one or less than all four quadrants of each eye are stimulated. In that event, only the quadrant(s) that is(are) stimulated are indicated by a bright square in the corresponding quadrant of the circles 62 and 64.

Figure 12:
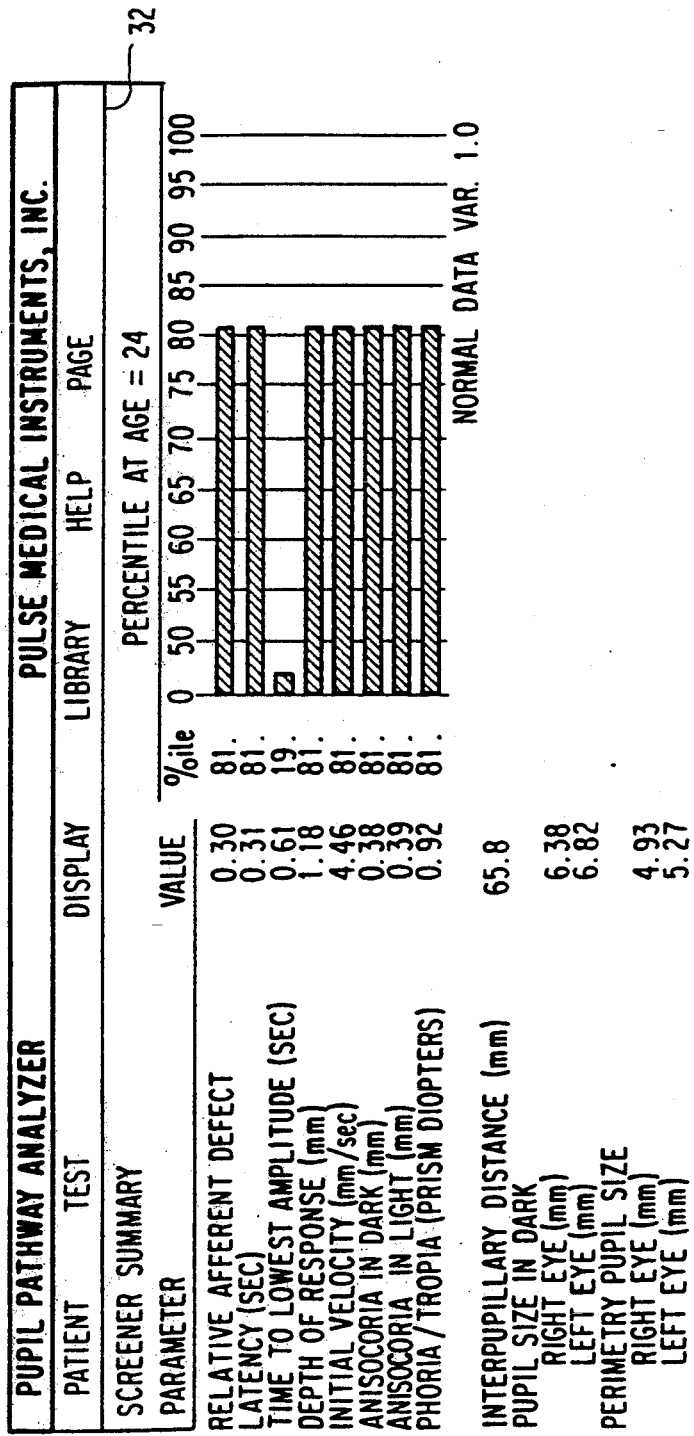
FIG. 12 illustrates the screener summary data screen.

Testing continues until the tests of the screener are completed. These include the step response test, and the cover/uncover test in the example being described. When the tests are complete for the screener, a buzzer, bell or other audible signal sounds indicating that the patient may remove his or her head from the aperture 14 of the instrument. An audible signal is also generated between tests of the screener indicating that the patient is allowed to blink. The display screen automatically switches from the CGA mode to the EGA mode in order to display the test data in a higher resolution mode. This data is generated by the microprocessor in the instrument and displayed automatically when testing is complete. The first screen displayed is illustrated in FIG. 12 and is a summary of the screener tests including the patient's percentile for his or her age.

Figure 13:
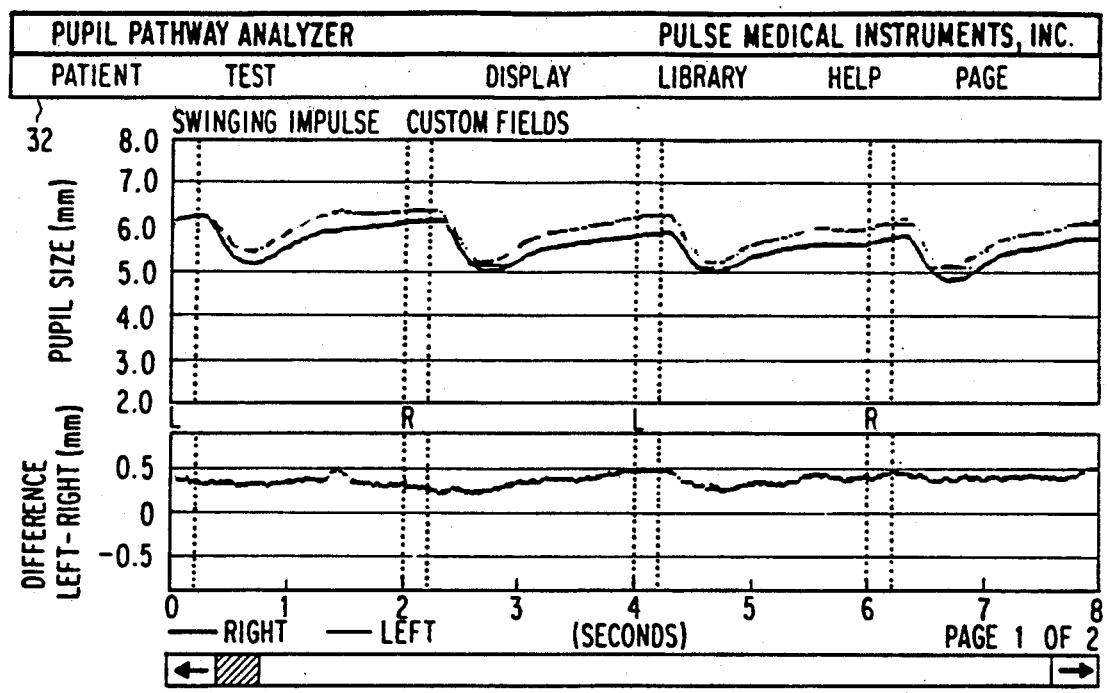
FIG. 13 illustrates the first of two graphical data screens for the swinging impulse test.
Figure 14:
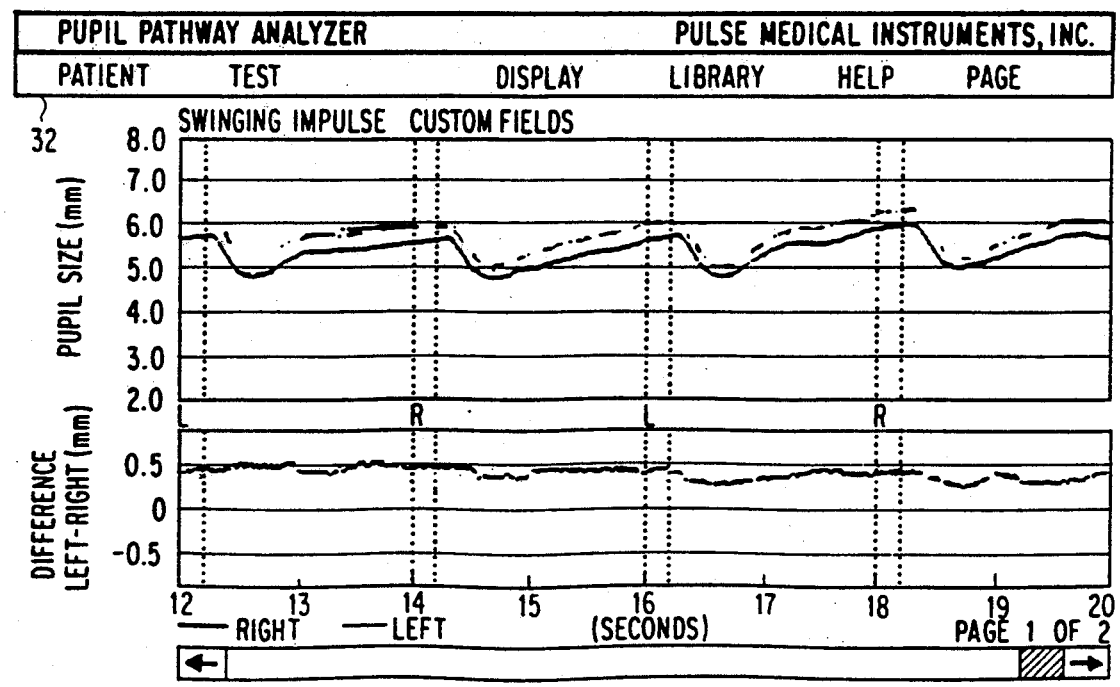
FIG. 14 illustrates the screen of FIG. 13 scrolled to the right.

By selecting the PAGE command (which only appears if there is more than one page to display), a graphical presentation of the results of the swinging impulse test is displayed in the screen illustrated in FIG. 13. It will be observed that the top part of the graph separately shows the reactions of the right and left pupils correlated with the impulses. The graphs for the right and left eyes are displayed in different colors (here, solid and dotted lines) so as to better distinguish them. The difference between the reactions of the right and left pupils is plotted in the lower part of the graph. In this screen, there is also displayed a cursor bar 68, and by selecting either the right or left arrows, the operator can scroll the graph in either the right or left direction so as to be able to view all the graphical data computed from the test. This is illustrated in FIG. 14 where the right cursor arrow has been selected. In addition, it will be observed that this screen represents one of two pages of graphical data, as indicated just above the cursor bar 68 at the right hand edge thereof. In order to view the second page, the operator simply selects the PAGE command in the command bar 32, and when this is done, the screen illustrated in FIG. 15 is displayed.

Figure 15:
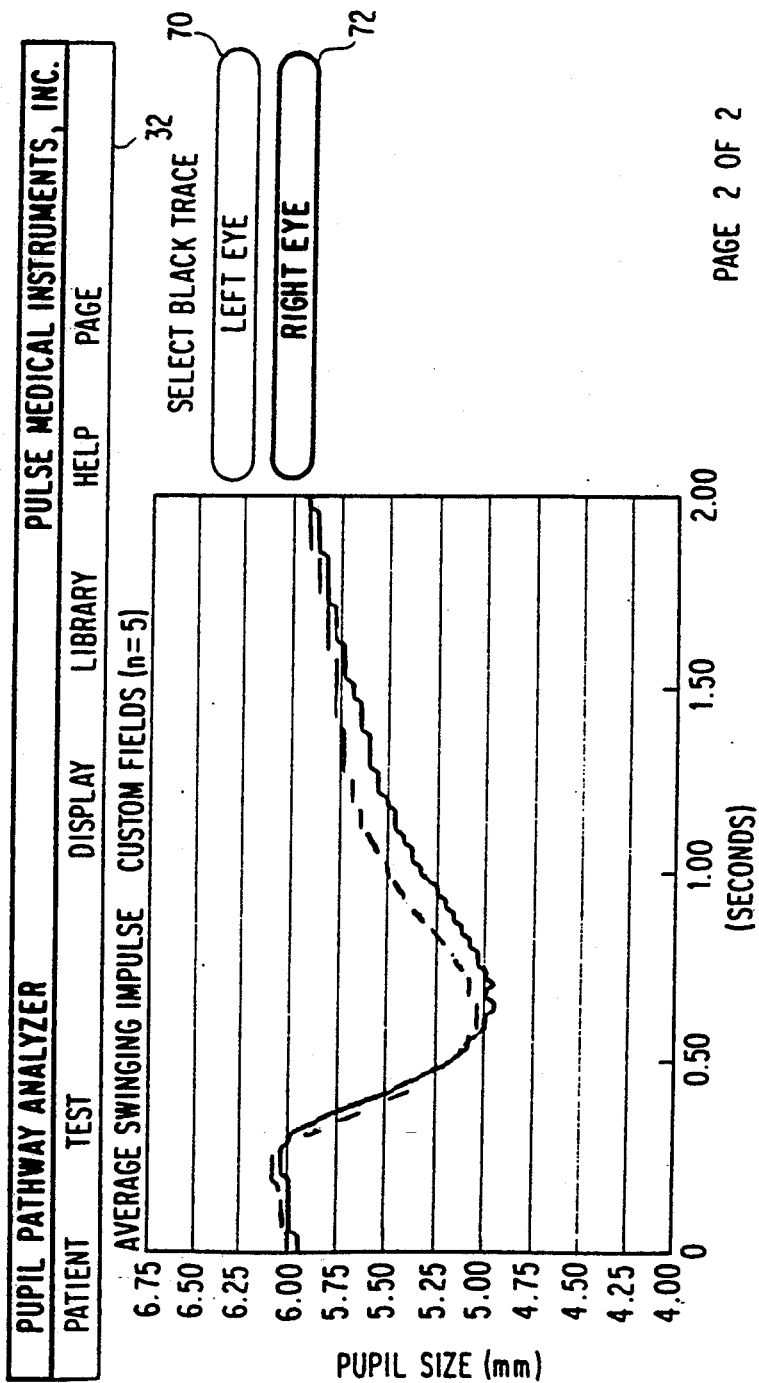
FIG. 15 illustrates the second of the two graphical data screens for the swinging impulse test.

The screen in FIG. 15 is a graph of the computed average for the swinging impulse test with each eye displayed in a different color. At the top of the screen, there is displayed "n=5" indicating that the displayed average was computed from five swinging impulse repetitions. Actually, more repetitions may have been run by the instrument, but due to blinks by the patient having been detected, the other repetitions would not have been used in the computation. This screen provides the operator with LEFT and RIGHT eye buttons 70 and 72, respectively, for purposes of selecting which of the graphs is displayed in black so that the operator can better distinguish between the graphs.

Figure 16:
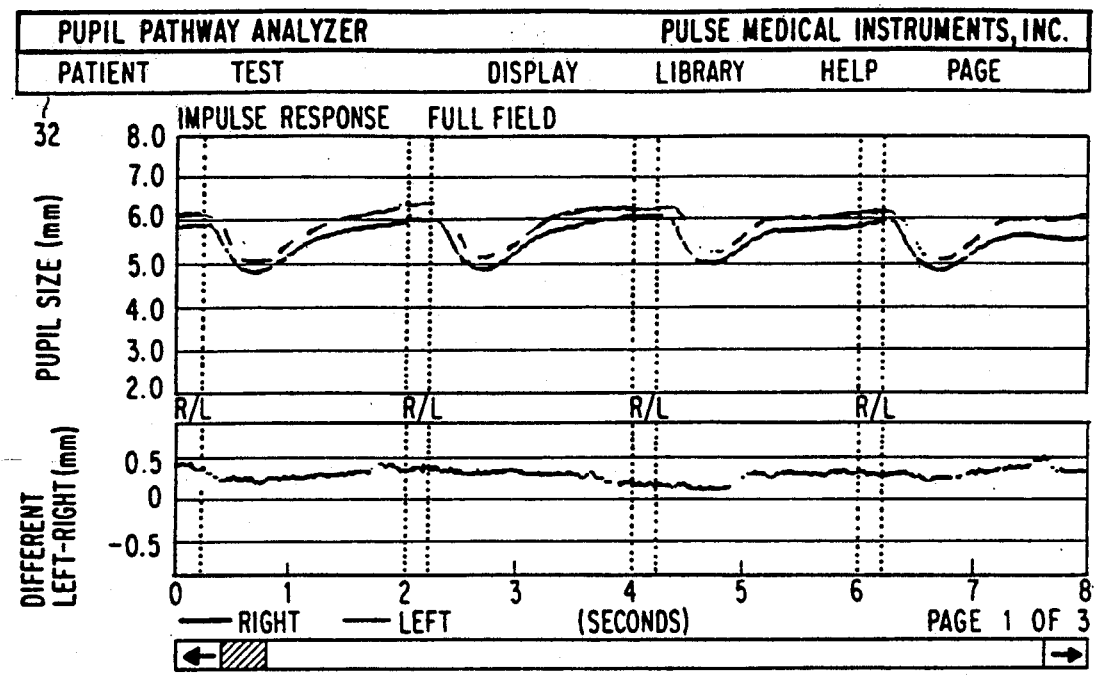
FIG. 16 illustrates the first of three data screens for the impulse response test.
Figure 17:
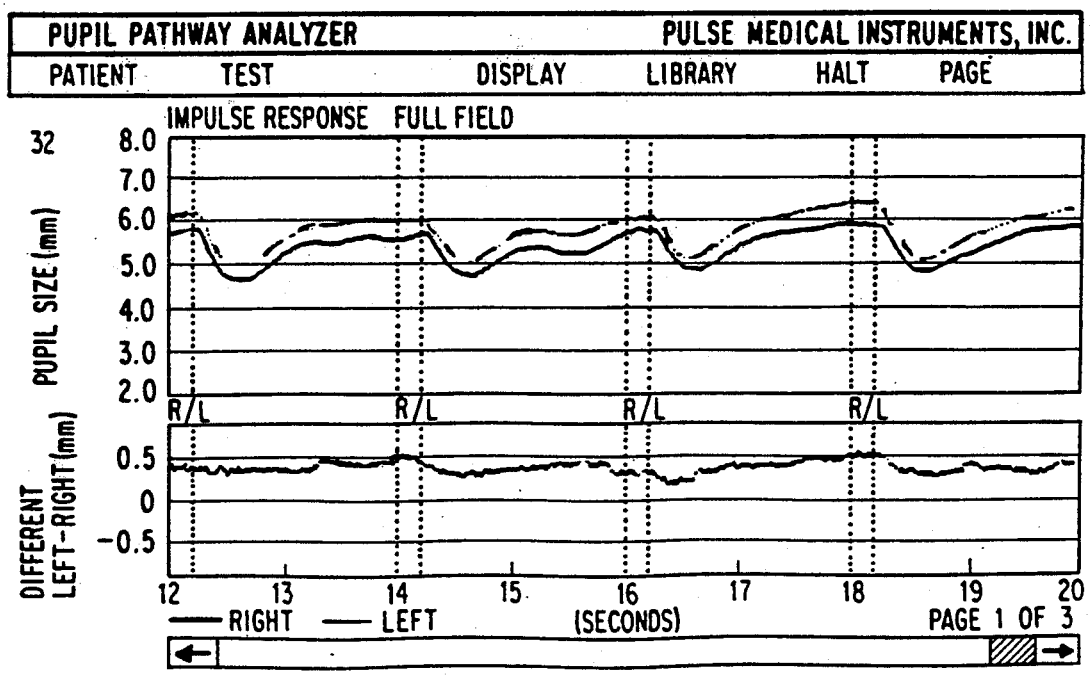
FIG. 17 illustrates the screen of FIG. 16 scrolled to the right.

The operator may now select the PAGE command from the command bar 32 to display the computed graphical data from the next test. The first screen for the impulse response test is shown in FIG. 16. This screen is similar to the screen illustrated in FIG. 14, but for impulse response data, and it too may be scrolled as indicated by the screen shown in FIG. 17. The display of graphical data for the impulse test indicates that it is but one of three pages. Therefore, the operator selects the PAGE command from the command bar 32 to display the screen shown in FIG. 18. This is a display of average impulse response computed from ten impulse response tests. The third page of the impulse response data is shown in FIG. 19 which provides an impulse response summary for each eye.

The next test run by the screener was the perimetry pupil size test, and by selecting the PAGE command from the command bar 32, the operator can display the data from that test. This is illustrated by the screen shown in FIG. 20 which provides the measured sizes of the pupils for the right and left eyes.

Similar displays of data are made for the other tests of the screener. When all the displays of data are concluded for the tests for the screener, the operator may want to run a further test, perhaps because of something observed in one of the screener tests. This the operator can do by simply selecting the TEST command from the command bar 32. This causes the pull down window 40 to be displayed over the current display as shown in FIG. 21. In the illustrated example, the operator now wants to run a Hippus test as indicated by the reverse highlight in the pull down window.

Figure 23:
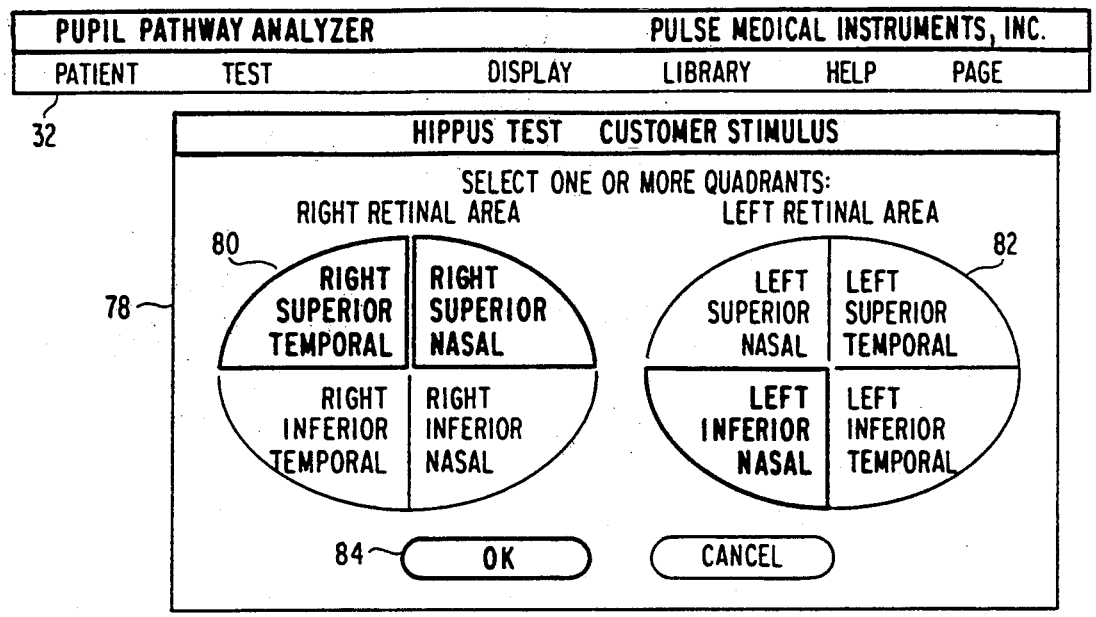
FIG. 23 illustrates the custom stimulus dialog box for configuring the stimulus for the Hippus test.

The operator is next presented with a dialog box 72 to select the desired stimulus as shown in FIG. 22. The operator has selected the "custom field" stimulus for the Hippus test and now has the option to select either the CANCEL or OK buttons 74 or 76. By selecting the OK button 76, the dialog box 78 is displayed as shown in FIG. 23. This dialog box provides two circles 80 and 82 corresponding to the circles 64 and 66 shown in FIG. 9, 10 and 11. The circles 80 and 82 are divided into to four quadrants as illustrated, and each of these four quadrants can be selected by the operator by using the light pen 24. Once the custom stimulus configuration has been selected, the operator has selected the OK button 84 to implement the custom stimulus for the Hippus test.

It will be understood from the foregoing description that similar stimulus configuration can be provided for any of the other tests performed by the instrument. In each case, the screen displayed in FIG. 23, but for the particular test involved, is used to configure the stimulus fields.

Figure 24:
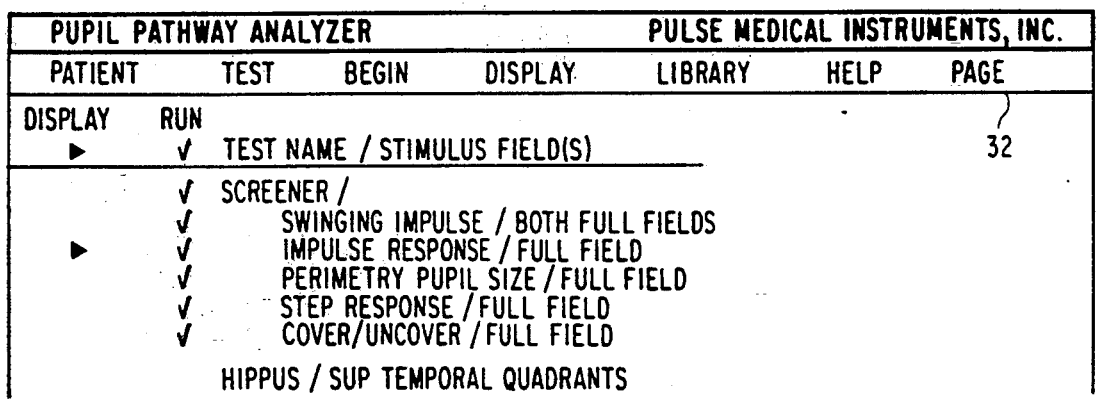
FIG. 24 illustrates the test list screen, showing the names of the tests already run and those which have been selected but not yet run.
Figure 25:
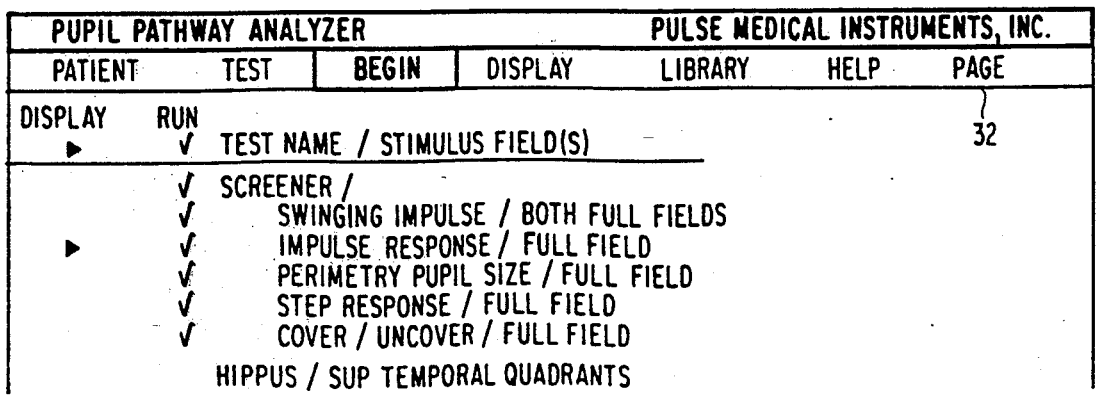
FIG. 25 illustrates the selection of the BEGIN command for the Hippus test.

Once the stimulus fields have been configured, the test list is displayed as illustrated in Figure 24. It will be observed that this screen is the same as that shown in FIG. 6 except that the Hippus test has been added. The screener tests are all displayed with a check mark to the left indicating that these tests have already been run for this patient. In FIG. 25, the operator selects the BEGIN command in the command bar 32 to start the test.

Figure 26:
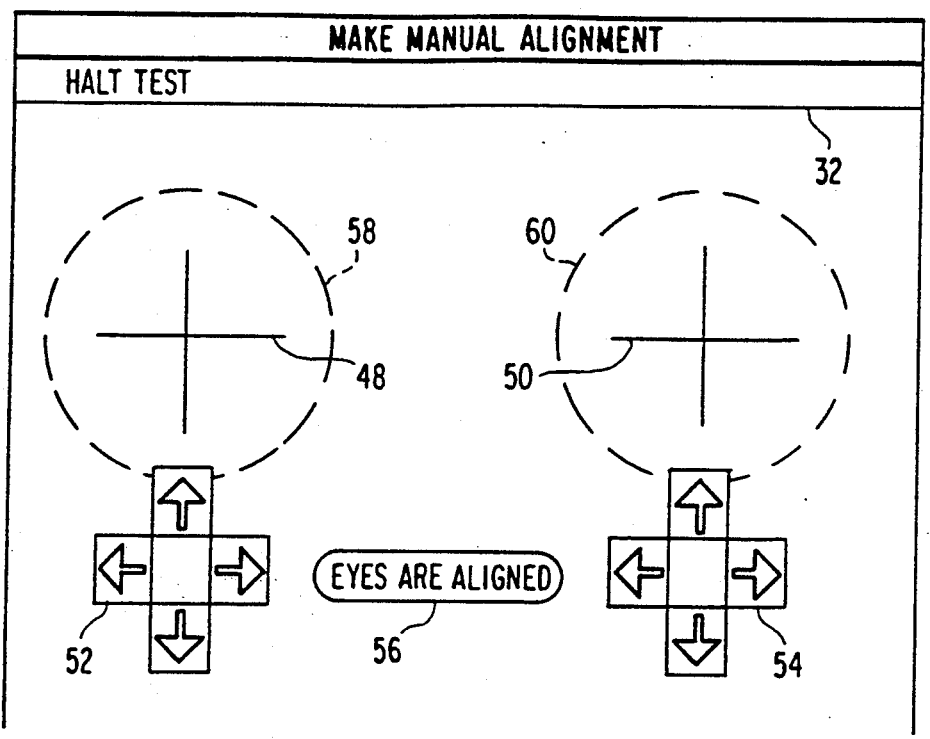
FIG. 26 illustrates the video screen used to align the images of the patient's pupils on the video screen.
Figure 27:
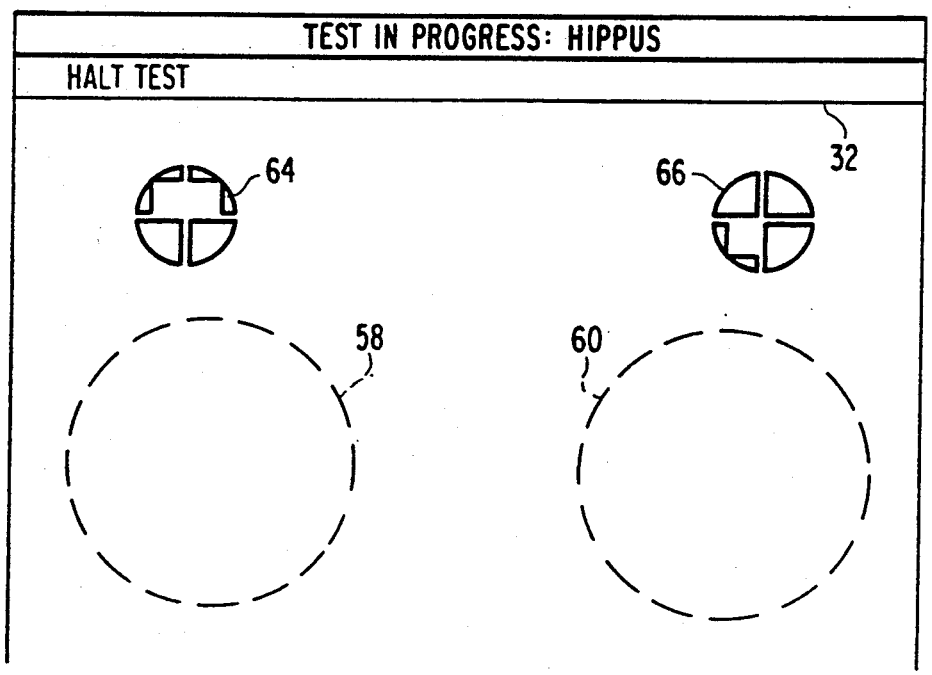
FIG. 27 illustrates the video screen during the Hippus test.

At this point the display switches from EGA to CGA mode and again displays the alignment video display screen, as shown in FIG. 26. Once the patient's pupils 58 and 59 are aligned with the cross hairs 48 and 50, the instrument runs the test as shown in FIG. 27. Note in this figure that the circles 64 and 66 show the custom field stimulus used for this particular test.

Figure 28:
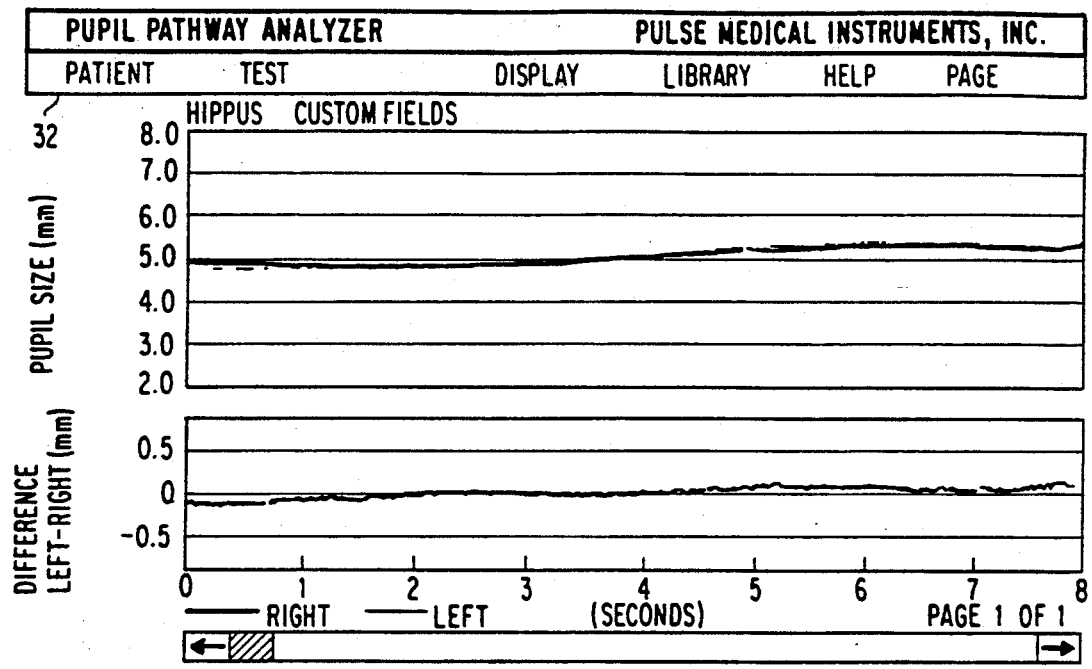
FIG. 28 illustrates the graphical data screen showing the results of the Hippus test.
Figure 29:
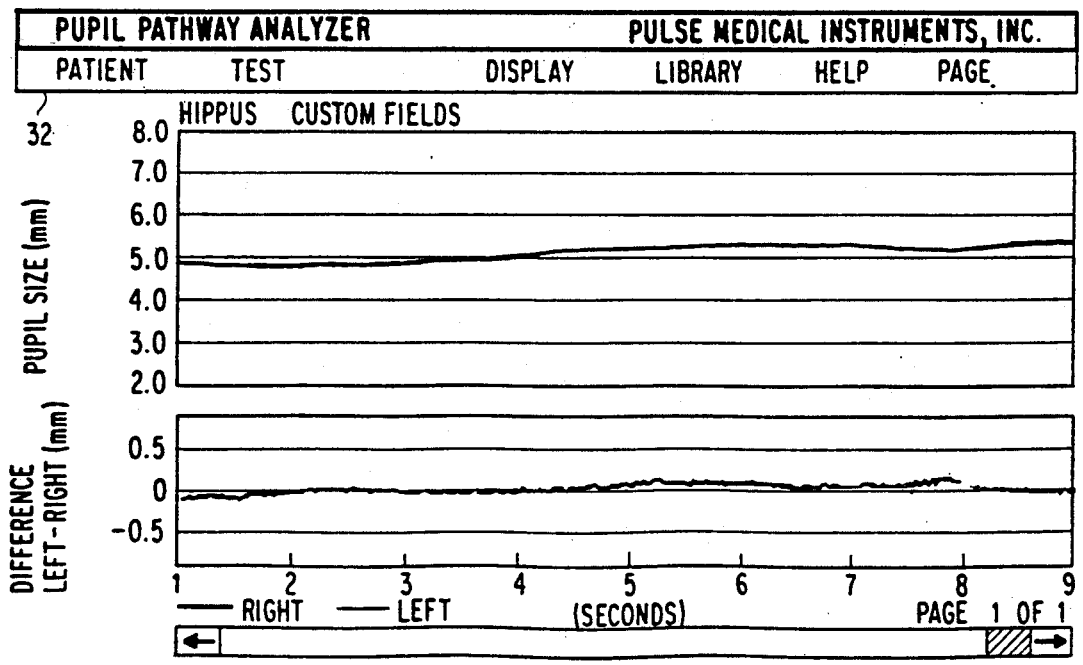
FIG. 29 illustrates the screen of FIG. 28 scrolled to the right.

When the test is complete, the display switches back to the EGA mode, and displays the computed graphical data as shown in FIG. 28. Again, this display can be scrolled as shown in FIG. 29.

Figure 30:
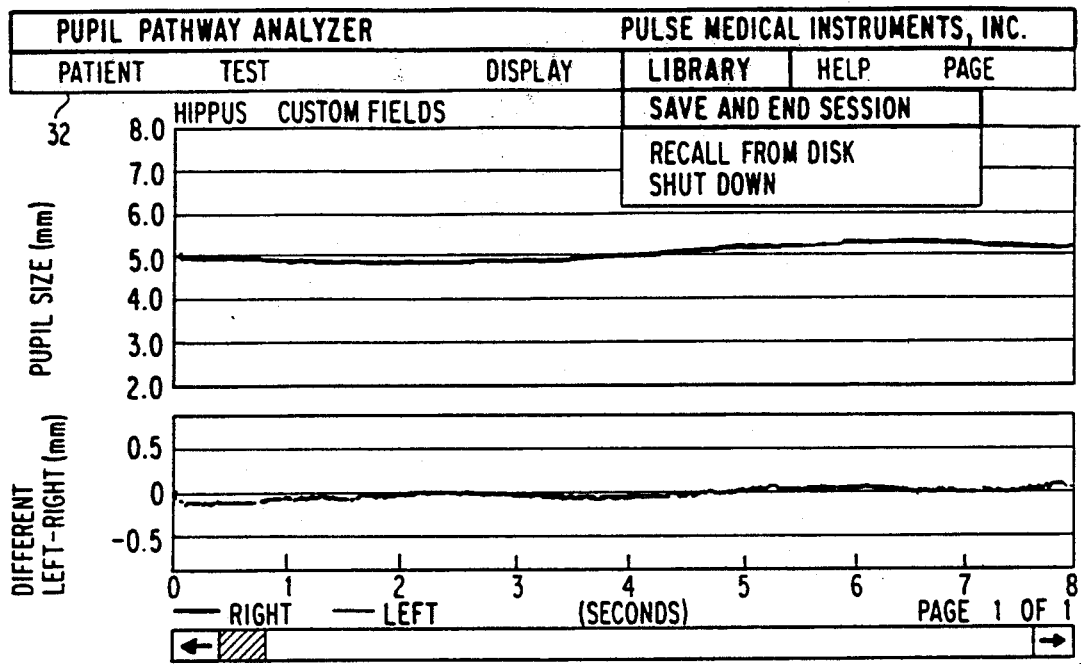
FIG. 30 illustrates the pull down window which is displayed when the LIBRARY command is selected.
Figure 31:
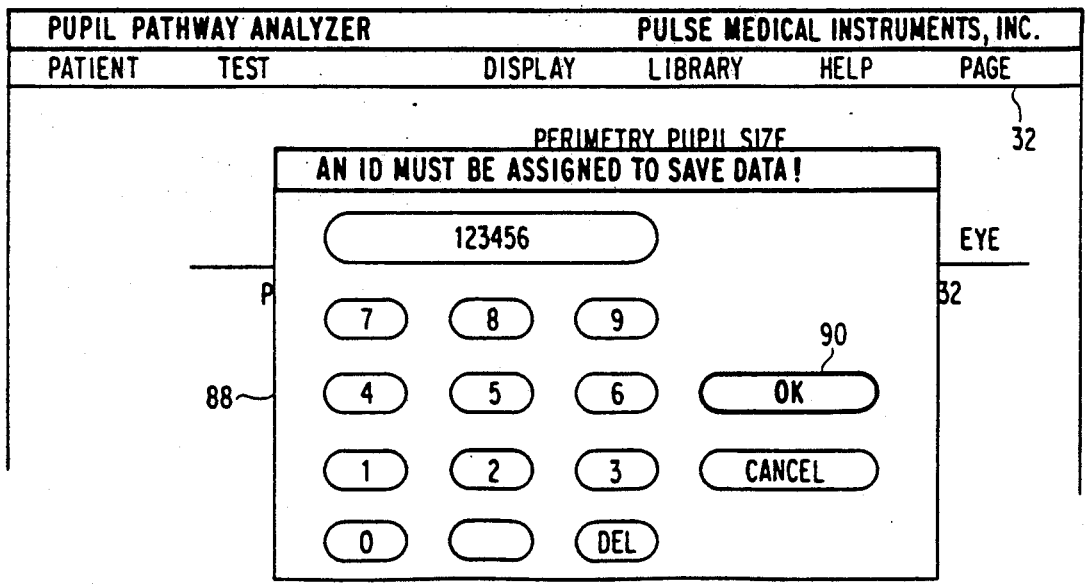
FIG. 31 illustrates the dialog box which is displayed for entering the patient's ID.
Figure 32:
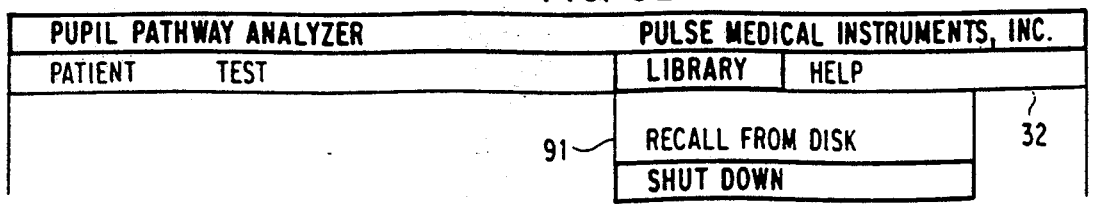
FIG. 32 illustrates the pull down window which is displayed when the LIBRARY command is again selected for ending a session.

For our example, the operator is now finished testing the patient and wants to store the data generated by the tests. Therefore, in FIG. 30, the operator selects the LIBRARY command from the command bar resulting in pull down window 86 being displayed. In this window, the operator selects the SAVE command in the command bar 32. This causes the numeric keypad to be displayed again in dialog box 88 with the request that the operator enter the patient's ID as shown in FIG. 31. The operator has entered an ID of 123456 and selected the OK button 90. The system saves the data to the system hard disk and then clears the display screen. Now, to exit the system, the operator selects the LIBRARY command again from the command bar in the screen shown in FIG. 32 and then selects the SHUT DOWN option in pull down window 91. This causes the system to return to the operating system and the instrument can be turned off.

Having described the overall operation and the external interface of the instrument, the internal subsystems which accomplish this operation will now be described.

Optical Subsystem

Figure 33A:
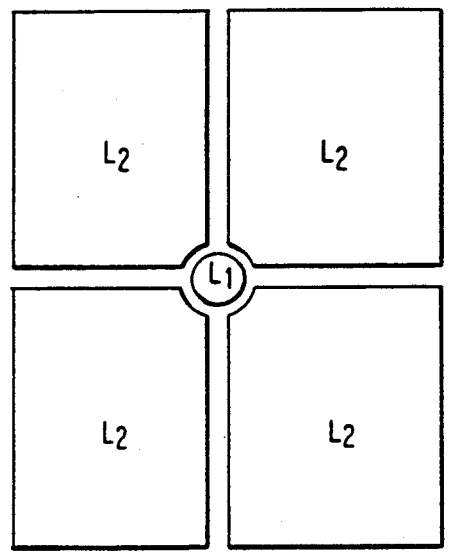
FIG. 33A is an elevation view showing the arrangement of the lenses $L_1$ and $L_2$.
Figure 34:
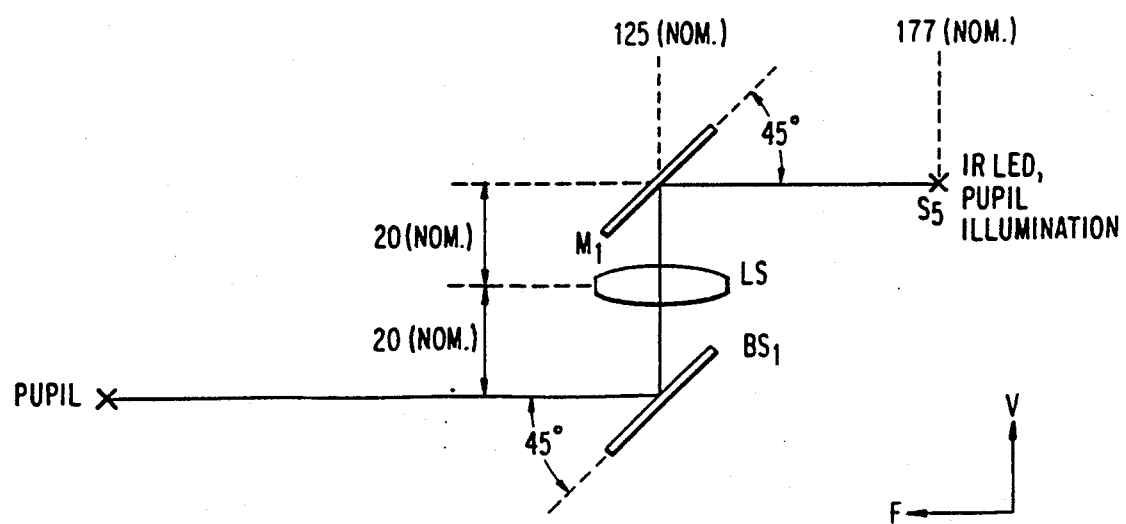
FIG. 34 is a schematic diagram showing the optical system viewed from the left side.

FIGS. 33, 33A and 34 show the structure of the optical subsystem. It will be noted that all of the system nearest the eyes is duplicated (in mirror image) for each eye. The system features independent focus for each eye, four quadrant illumination for each retina and a 30° cone of vision for each eye.

Considering first the portion of the optical system that delivers visible lights to the patient's eyes, source $S_1$ is a small, green light emitting diode (LED) that flickers continuously. Aperture $G_1$ lies in the back focal plane of lens $L_1$ so that the light from $S_1$ that passes through $G_1$ is collimated as it emerges from the other side of lens $L_1$ (see FIG. 33A). That light is reflected from a "cold mirror" $CM_1$ and enters the patient's right pupil. A "cold mirror" is a mirror that reflects visible light, e.g., the green light from source $S_1$, and transmits infrared light.

Light from source $S_1$ passes through lens $L_1$, reflects from cold mirror $CM_1$, passes through the right pupil, and falls on the right retina. Lens $L_1$ forms an image of source $S_1$ in the center and plane of the right pupil, and the optics of the eye, in combination with lens $L_1$, form an image of aperture $G_1$ on the retina. As a consequence, because $G_1$ is round, the patient sees a small flashing disk of green light. Similarly, light from the corresponding LED source $S_3$ and aperture $G_2$ enters the left eye as from a source at infinity. Because the paths followed by the light from these two LEDs from the two cold mirrors $CM_1$ and $CM_2$, respectively, to the two eyes are parallel, the apertures $G_1$ and $G_3$ act as a single "fixation point"; that is, for a normal visual system, the two disks appear as a single, small, flashing green light a long distance away. Their function is simply to provide the patient with something to look at, thus keeping their eyes relatively still and focussed at infinity or as close to infinity as their refractive error allows.

Sources $S_2$ are yellow LEDs. Light from sources $S_2$ pass through lenses $L_2$, and is reflected from cold mirror $CM_1$ to the right eye. Lenses $L_2$ form images of sources $S_2$ in the plane of the patient's pupil, and the light then passes through the pupil and illuminates one or more of the four quadrants of the retina. If the patient is looking at source $S_1$, then the light from sources $S_2$ will fall respectively on the superior and inferior temporal and superior and inferior nasal quadrants of his right retina as indicated, for example, in FIG. 23. The size of source $S_2$ and the magnification of its image in the plane of the patient's pupil are such that the image is much smaller than the smallest pupil diameter. Thus, the amount of light that falls on the retina from sources $S_2$ does not change when the pupil size changes, as it would do under ordinary circumstances.

The lens assembly for lenses $L_1$ and $L_2$ is shown in FIG. 33A and comprises the centrally mounted lens $L_1$ surrounded by four Fresnel lenses $L_2$. These four lenses focus light from each of four LED sources $S_2$ on the right pupil and illuminate the four quadrants of the retina. The lens assembly for lenses $L_3$ and $L_4$ is similar to that shown in FIG. 33A but focus light from sources $S_3$ and $S_4$ on the left pupil.

Considering next the part of the optical system that provides images of the patient's pupils, reference is made to FIG. 34 which shows part of the optics for the right eye. It will be understood that this part of the optics for the left eye is identical and is therefore not shown. Source $S_5$ is a small infrared-emitting LED. Infrared light reflected by mirror $M_1$ passes through lens $L_5$ and half of it is reflected from a beam splitting mirror $BS_1$. Light reflected from mirror $BS_1$ is transmitted through the cold mirror $CM_1$ (FIG. 33) to the right eye. Lens $L_5$ forms an image of source $S_5$ in the plane of the patient's pupil (superimposed on the images of sources $S_1$ and $S_2$). The image of source infrared light passes through the pupil and spreads over a region of the retina.

With continued reference to FIG. 34, some of the infrared light reflected from the retina emerges back out of the pupil and travels back through cold mirror $CM_1$ and beam splitter $BS_1$. Part of that light is reflected from beam splitter $BS_1$ toward lens $L_5$ and lost, but the rest is transmitted by beam splitter $BS_1$ and passes through lens $L_6$ (FIG. 33), which lies at its focal distance from the pupil. Therefore, the infrared image of the pupil, as back lighted by scatter from the retina, is collimated as it emerges from lens $L_6$ This light is reflected from a mirror $M_2$, part of it is reflected from another beam splitter $BS_3$ and passes through lens $L_7$, which forms an image of the pupil in its focal plane. An infrared sensitive video CCD (charge coupled device) camera is placed in that plane and positioned so that the image of the right pupil is centered on the left half of its photosensitive surface as viewed from the patient's perspective. The corresponding optical system for the left eye forms an image of the left pupil on the right side of the video camera by light transmitted through beam splitter $BS_3$. The two pupil images fall at different places on the CCD detector by virtue of the fact that beam splitter $BS_3$ is not positioned at 45°, but is slightly angularly displaced.

The distance between the centers of the two pupils varies over a range of about one inch among different patients. Therefore, when the system is correctly aligned to both pupils, the distance between the mirror $M_2$ and beam splitter $BS_3$ will be different for different patients. Note, however, that because the light from the right pupil is collimated as it passes between mirror $M_2$ and beam splitter $BS_3$, changes in that path length have no effect on the focus of the image of the right pupil.

Mechanical Subsystem

Figure 35:
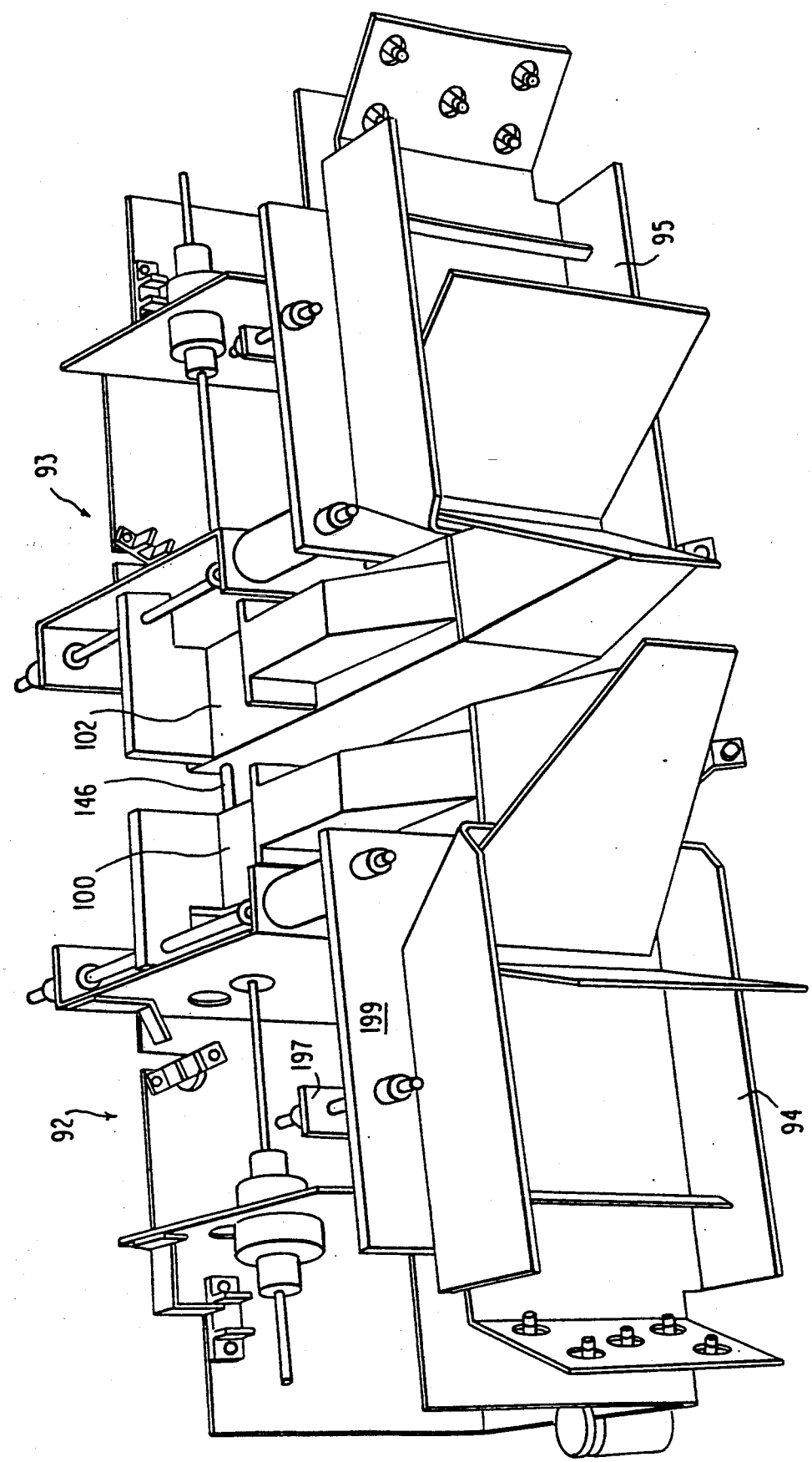
FIG. 35 is a perspective view of the overall mechanical assembly including left and right actuators.

FIG. 35 shows the overall mechanical assembly and includes a left actuator assembly 92 and a right actuator assembly 93. These assemblies provide the automatic focusing and tracking for the left and right pupils, respectively. The left actuator assembly 92 carries a left light box 94 which is shown in more detail in FIG. 36. This light box includes a housing 95 including a back plane 96. The LED sources $S_3$ and $S_4$ are mounted in the back plane 96 and the lens assembly for lenses $L_3$ and $L_4$ is mounted in the housing 95. The cold mirror $CM_2$ is mounted within housing 95 at an angle of 52.5° to the lens assembly. The right light box 97 (FIG. 35) carried by the right actuator assembly 90 is the mirror image of the left light box 94 shown in FIG. 36.

Referring back to FIG. 35, the left actuator assembly 92 also carries a left scope 100, and the right actuator assembly 93 carries a right scope 102. An exploded view of the left scope 100 is shown in FIG. 37, to which reference is now made.

The left scope 100 comprises three basic subassemblies. These are the left scope box 104, the left piston assembly 106 and the IR box assembly 108. The IR box assembly 108 houses the IR LED source $S_6$ and mirror $M_2$ corresponding to source $S_5$ and mirror $M_1$ for the right eye shown in FIG. 34. It is attached to the top of the left scope box 104 by screws.

Figure 37B:
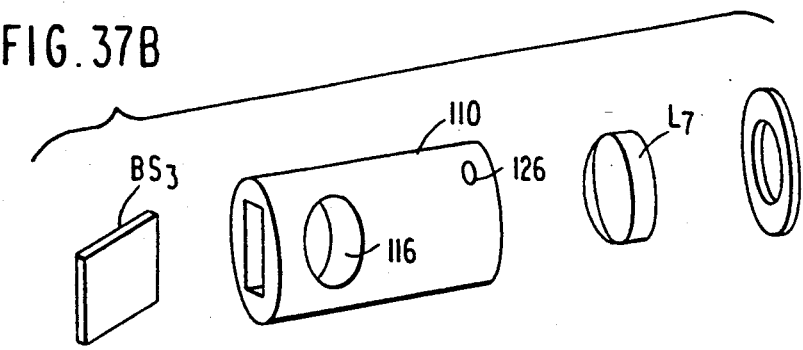
FIG. 37B is an exploded view of the left piston assembly.

The left scope box 104 is shown in exploded view in FIG. 37A and houses lens $L_8$ and beam splitter $BS_2$ which focus and reflect IR light onto the pupil of the left eye. The scope box 104 also houses lens $L_9$ which collimates IR light from the left pupil that passes through the cold mirror $CM_2$ and beam splitter $BS_2$ (FIGS. 34 and 37B).

The left scope box 104 as shown in FIG. 37 also houses the left piston assembly 106, which is shown in exploded view in FIG. 37B. This assembly comprises a piston 110 that houses beam splitter $BS_3$ and lens $L_7$. The left piston assembly is spring loaded within the left scope box 104 by a coil spring 112, and the left scope box 104 is closed by an end cap 114 held to the box by screws, as shown in FIG. 37. As shown in FIGS. 37 and 37B, the left piston 110 has an aperture 116 which registers with a corresponding aperture 118 in the side of left scope box 104. Further, the end cap 114 has an aperture 120 aligned with the longitudinal axis of the left scope box 104, and the opposite end of the scope box 104 is provided with an aperture 122. These apertures provide the light passages for the optical system. In addition, the scope box 104 is provided with a face 124 at an angle to the longitudinal axis of the box to provide clearance to the back of cold mirror $CM_2$ of the left light box assembly (FIG. 36). The piston 110 also has a hole 126 which registers with a notch 128 in the back edge of the left scope box 104. As will be described with respect to the right scope box assembly, this hole receives a rod that connects to the corresponding right piston assembly to maintain the alignment of mirror $M_2$ and beam splitter $BS_3$, shown in FIG. 33.

The construction of the right scope 102 is similar in construction to the left scope 100 and also comprises three basic subassemblies. These are the right scope box 130, the right piston assembly 132 and the IR box assembly 134. The IR box assembly 134 houses the IR LED source $S_5$ and mirror $M_1$. It is attached to the top of the right scope box 130 by screws.

Figure 38:
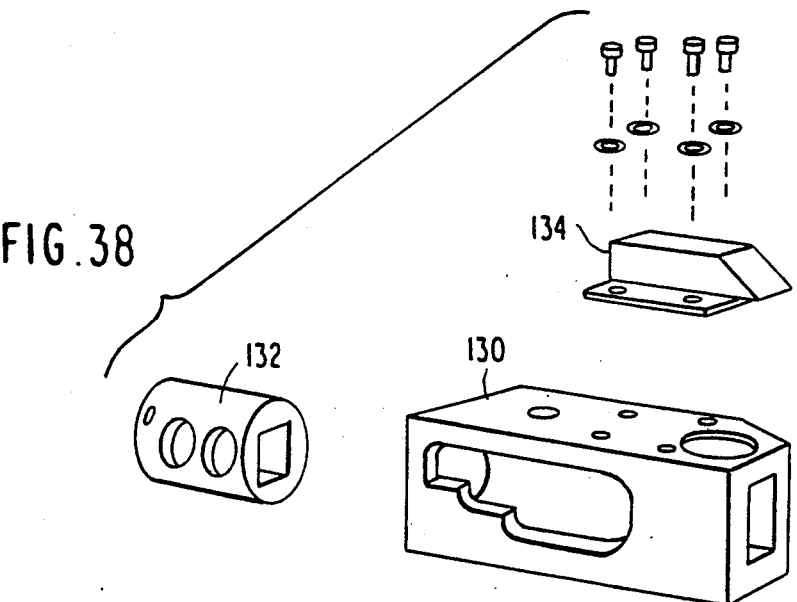
FIG. 38 is an exploded view of the right scope assembly.
Figure 38A:
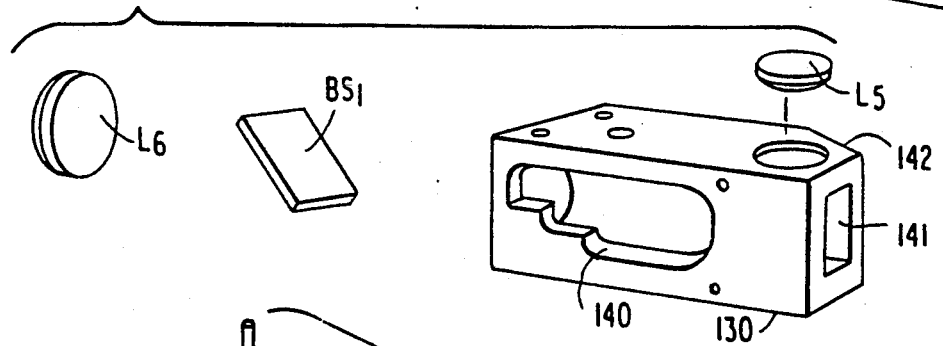
FIG. 38A is an exploded view of the right scope box assembly.

The right scope box 130 is shown in exploded view in FIG. 38A and houses lens $L_5$ and beam splitter $BS_1$ which focus and reflect IR light onto the pupil of the right eye. The scope box 130 also houses lens $L_6$ which collimates IR light from the left pupil that passes through the cold mirror $CM_1$ and beam splitter $BS_1$ (FIGS. 34 and 37B).

Figure 38B:
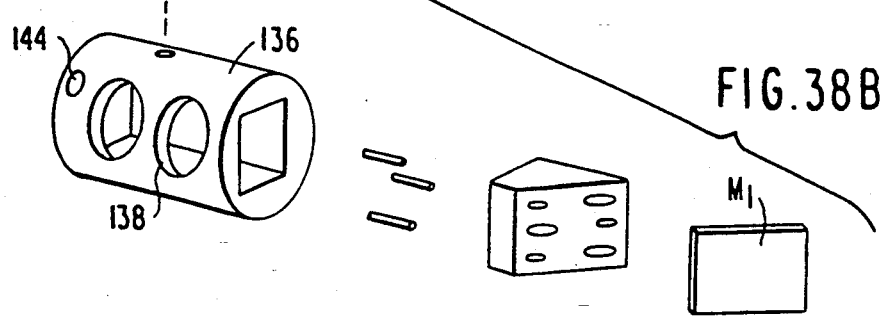
FIG. 38B is an exploded view of the right piston assembly.

The right scope box 130 as shown in FIG. 38 also houses the right piston assembly 132, which is shown in exploded view in FIG. 38B. This assembly comprises a piston 136 that houses mirror $M_2$ As shown in FIGS. 38 and 38B, the right piston 136 has an aperture 138 and the right scope box 130 has an aperture 140 in its side. The end of the scope box 130 nearest lens $L_5$ is provided with an aperture 141. These apertures provide the light passages for the optical system. In addition, the scope box 130 is provided with a face 142 at an angle to the longitudinal axis of the box to provide clearance with the back of cold mirror $CM_1$ of the right light box assembly. The piston 136 also has a hole 144, corresponding to hole 126 in piston 110, which registers with the aperture 140. This hole receives the rod 146 shown in FIG. 35 that connects to the corresponding right and left piston assemblies to maintain the angular alignment of mirror $M_2$ and beam splitter $BS_3$.

Figure 39:
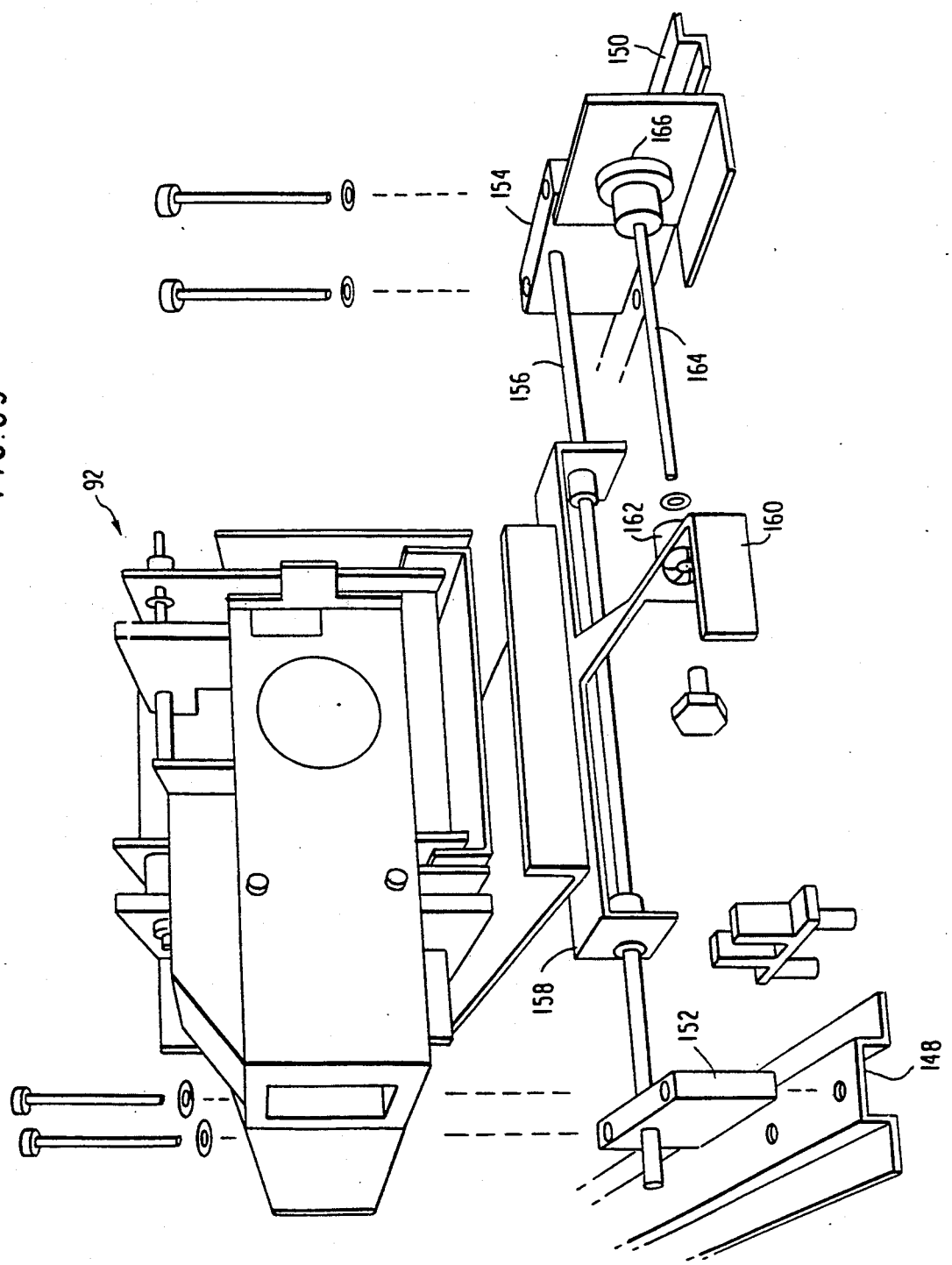
FIG. 39 is an exploded view of the focusing mechanism for the left actuator.

The focusing mechanisms are conventional servo slide positioning systems which move the left and right actuator assemblies forward and backward as viewed in FIG. 35. An exploded view of the focus servo system for the left actuator assembly 92 is shown in FIG. 39. Rails 148 and 150 carry support blocks 152 and 154 that support a rod 156. A carriage 158 is slidably mounted on the rod 156, and the left actuator assembly 92 is mounted to the carriage 158. Integral with the carriage 158 is a projecting arm 160 that carries a shock mount 162. The shock mount 162 carries a threaded actuator shaft 164 which extends through a follower nut internal to a servo motor 166. The rotation of the internal follower nut in servo motor 166 causes carriage 158 to move along the rod 156 in order to perform the focusing operation. A similar servo mechanism is used for the focus operation of the right actuator assembly.

Figure 40:
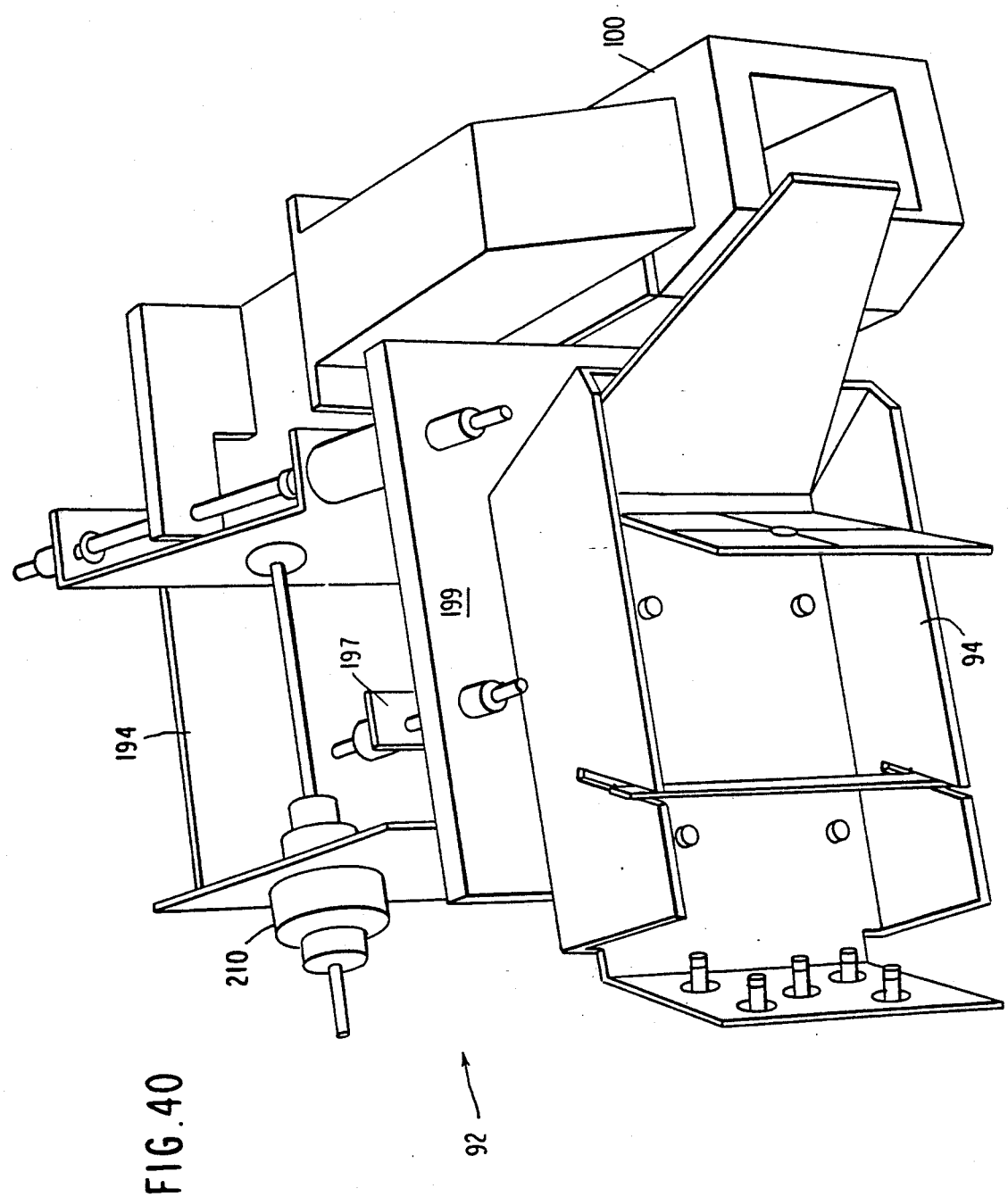
FIG. 40 is a perspective view of the left actuator.
Figure 40A:
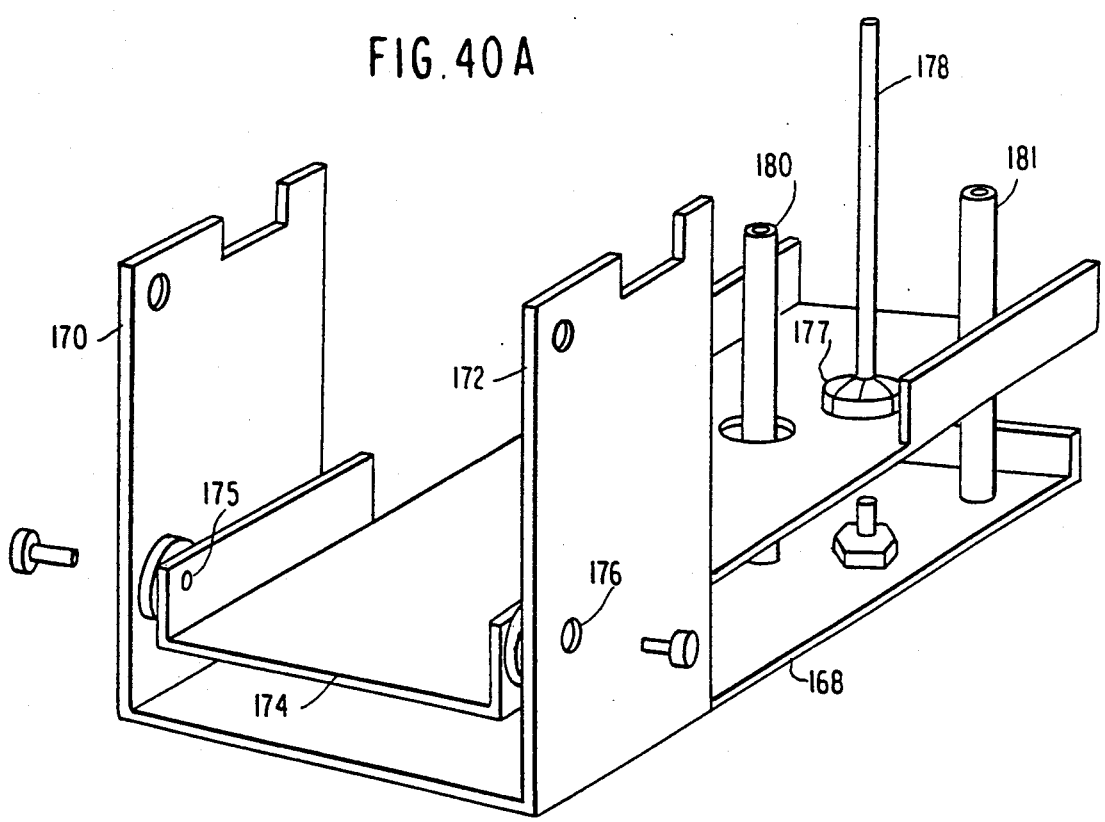
FIG. 40A is a perspective view of the base assembly for the left actuator.
Figure 40B:
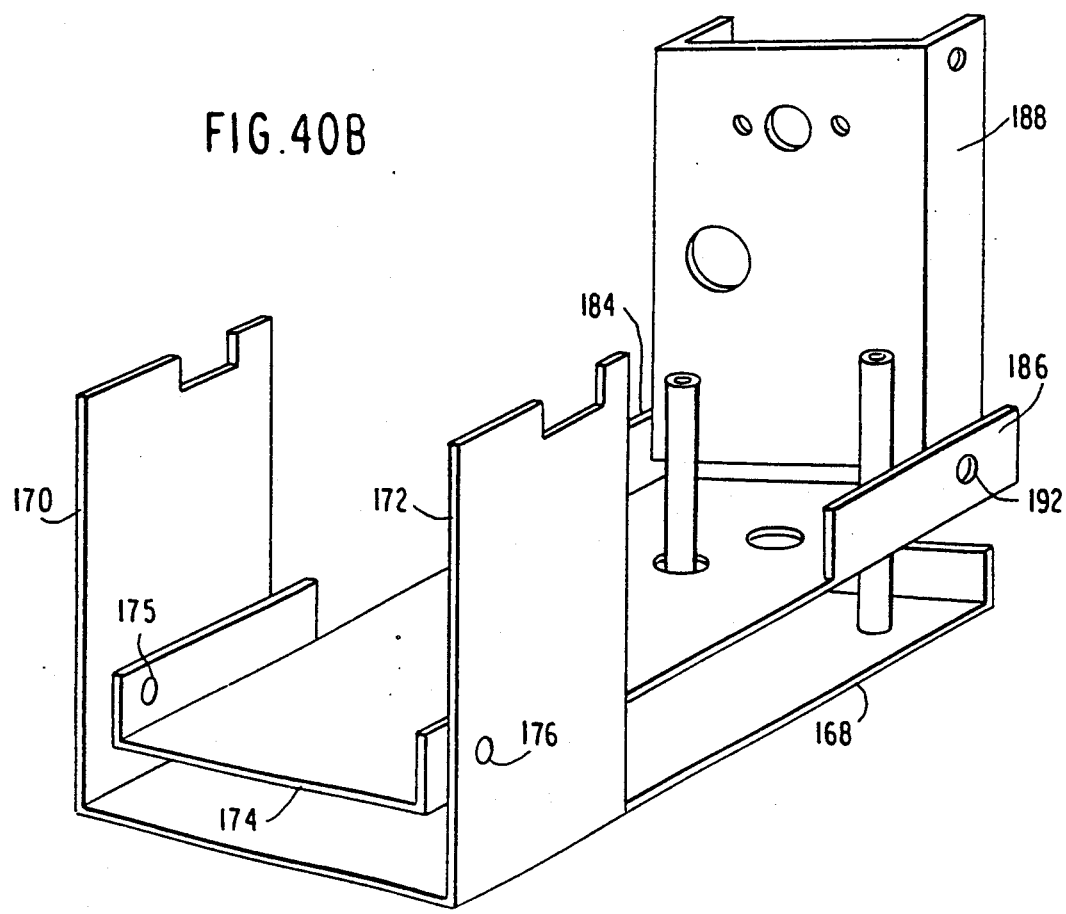
FIG. 40B is a perspective view of the base assembly of FIG. 40A with a pivoted vertical plate added.

While the focusing mechanism is generally conventional in design, the tracking mechanisms are of a unique, light weight and inexpensive design. The left actuator assembly 92 is shown in FIG. 40. As better shown in FIG. 40A, this assembly comprises a base 168 which is mounted to the carriage 158 (FIG. 39). The base 168 includes upwardly projecting flanges 170 and 172 to which one end of a subbase 174 is pivotally mounted at pivots 175 and 176. The opposite end of the subbase 174 therefore rotates about these pivots 175 and 176 to move vertically. Near this end of the subbase 174 is a shock mount 177 which is attached to a threaded actuator shaft 178 which is used to raise and lower the one end of the subbase 174. On either side of the shock mount 177 are two standoffs 180 and 181 which are mounted to base 168 and project up through holes in subbase 174. As will be shown in FIG. 40D, these standoffs are used to mount the servo motor which runs on the actuator shaft 178.

As shown in FIG. 408, the vertically moving end of the subbase 174 is provided with small flanges 184 and 186 to which is pivotally mounted a vertical plate 188 at pivots 190 (not visible) and 192. The opposite end of the vertical plate 188 therefore rotates about these pivots 190 and 192 to move horizontally.

Figure 40C:
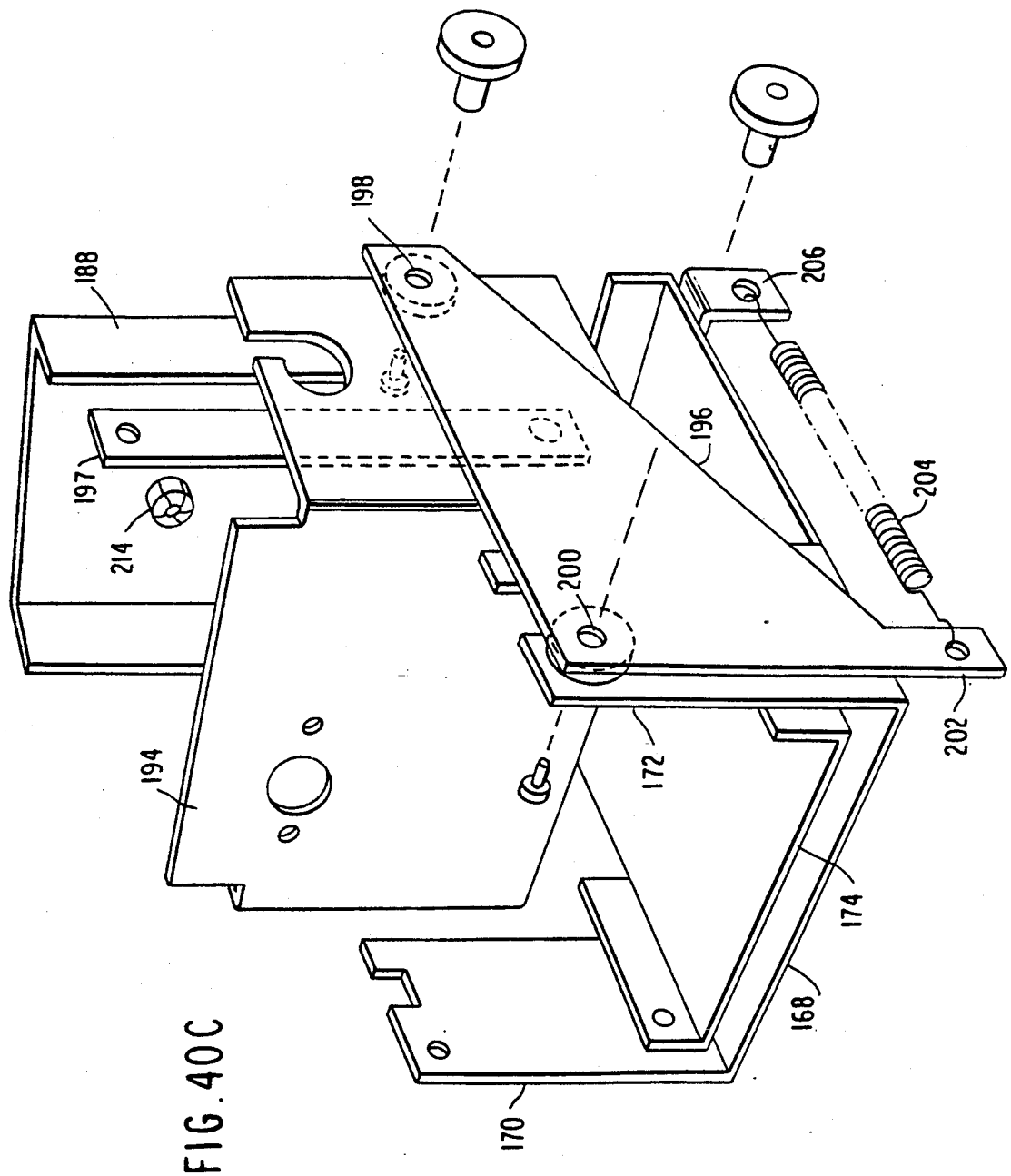
FIG. 40C is a perspective view of the base assembly of FIG. 40B with a subframe added.

FIG. 40C shows the addition of a subframe 194 which is attached to a generally triangularly shaped bracket 196 on one side thereof. More particularly, bracket 196 is connected to the subframe 194 by a first pivot 198, and the bracket 196 is in turn mounted to flange 172 by a second pivot 200. Parts 174, 168, 194 and 196 form a parallelogram at pivots 176, 192, 200 and 198. Thus, since the orientation of base 168 is held constant, so too is that of subframe 194 (the opposite side of the parallelogram). A downwardly projecting tab 202 is connected by a spring 204 to a downwardly projecting tab 206 on the base 168. This spring serves to unload the vertical servo by counterbalancing the weight of the assembly attached to the subframe 194.

Figure 40D:
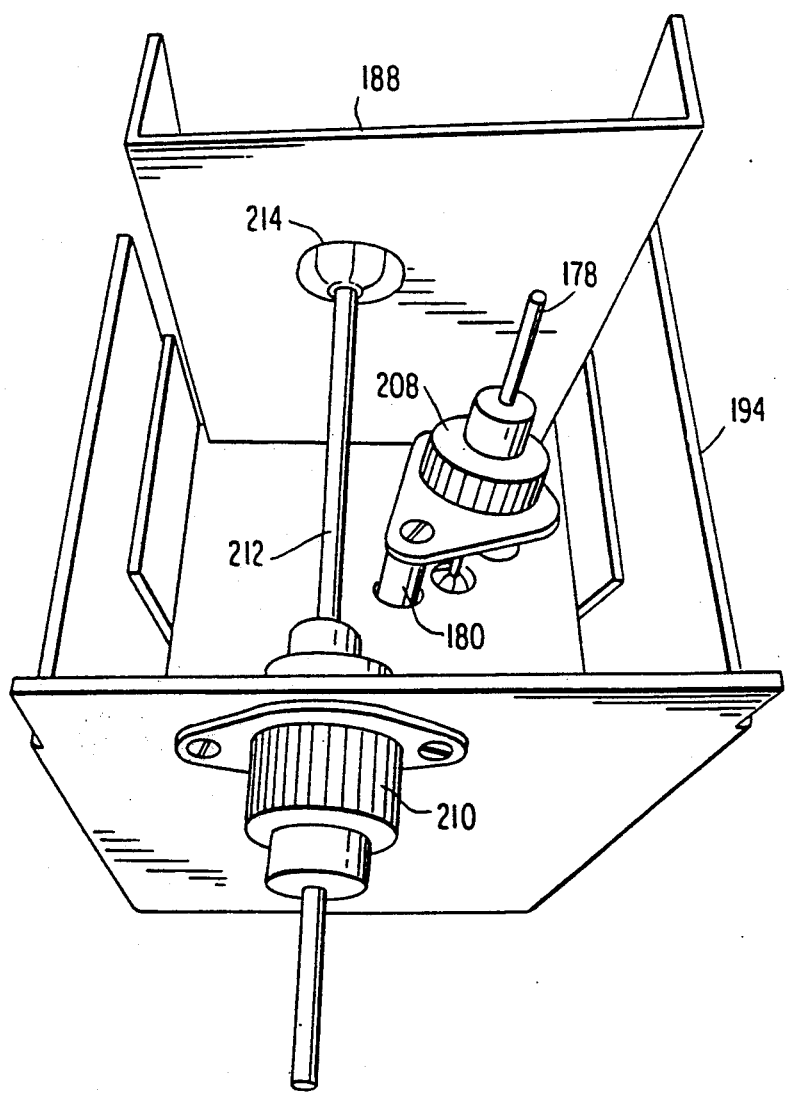
FIG. 40D is a perspective view looking into the subframe assembly shown in FIG. 40C.

FIG. 40D is a view down into the assembly showing a servo motor 208 mounted to the standoffs 180 and 181 for running on actuator shaft 178. The subframe 194 carries a second servo motor 210 which runs on a second actuator shaft 212 that engages a shock mount 214 in the vertical plate 188. Thus, horizontal motion is produced by servo motor 210 and vertical motion is produced by servo motor 208. A second parallelogram is formed by plate 188, subframe 194, the vertical linkage arm 197 and the plate 199 (see FIG. 40) to which the telescope assembly 100 is attached. In this way, the orientation of the telescope assembly 100 is held constant relative to that of subframe 194, and thus it is constant relative to base 168. This provides the capability for independent horizontal and vertical "swinging" motions, with no change in orientation of the telescope assembly. The mechanism is very lightweight and rugged, eliminating the usual slide mechanisms for producing the horizontal and vertical motions. In addition, the resulting mechanism is compact and inexpensive to manufacture.

Electronic Subsystem

Figure 41:
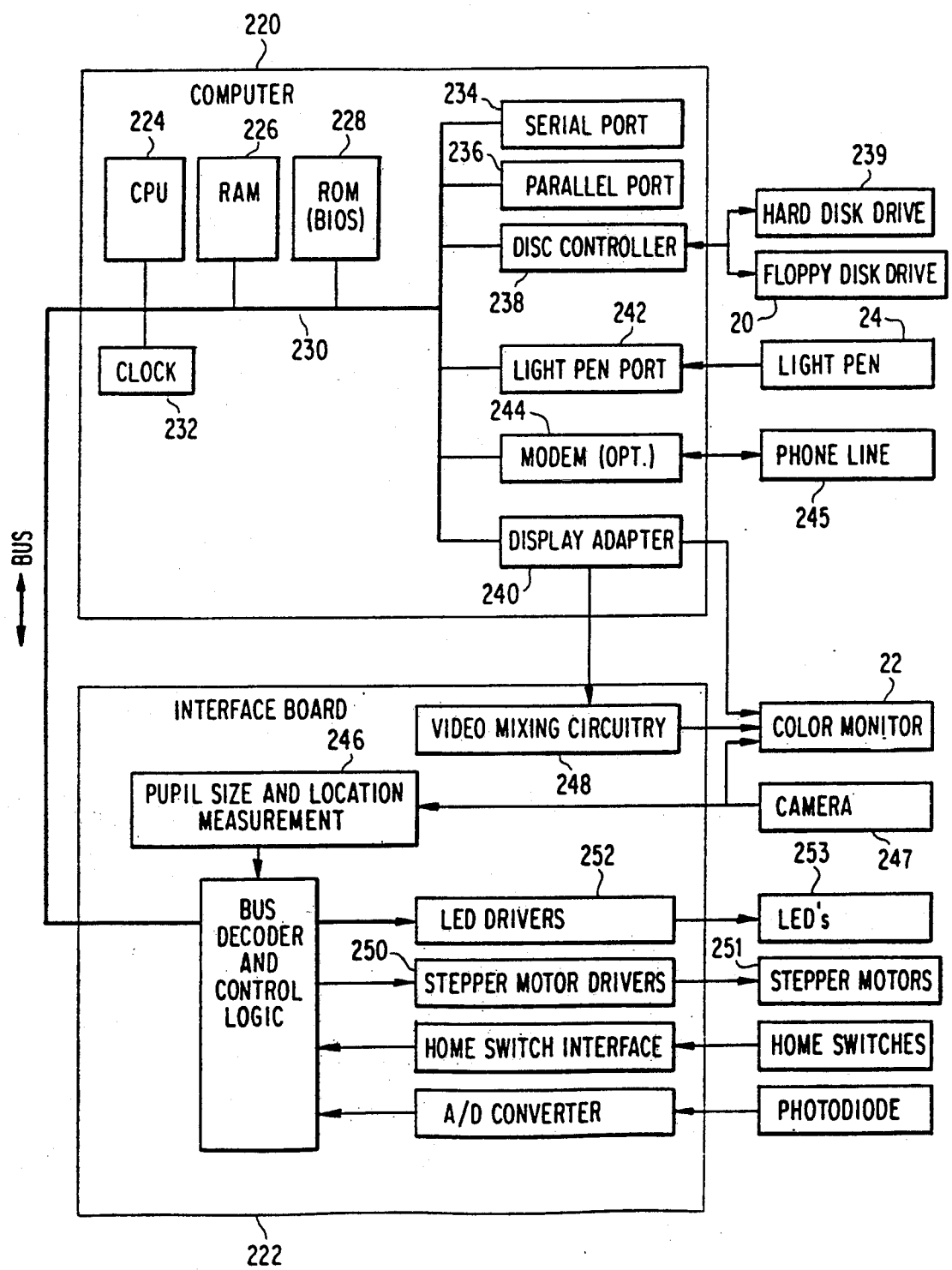
FIG. 41 is a block diagram showing the electronics of the system.

FIG. 41 is a block diagram of the instrument electronics. The two main subsystems are a digital computer 220 and interface electronics 222. The computer 220 may be, for example, an IBM personal computer or compatible based on Intel 8088, 8086, 80286 or 80386 microprocessors. Obviously, other computers based on other and different microprocessors may be used, and those skilled in the art will understand that, for example, an Appleo Macintosh!! computer or other computers based on Motorola 68000 or 68020 microprocessors could be used. The point is simply that the various components of the computer 220 are well known and available commercially from a variety of sources.

The computer 220 typically includes a microprocessor or central processing unit (CPU) 224 and supported by random access memory (RAM) 226 and read only memory (ROM) 228 connected to a common bus 230. The RAM 226 temporarily stores the controlling program for performing the focusing, alignment and tracking functions and for performing the selected tests on the patient. The ROM 228 stores the basic input/output system (BIOS) which provides the first level interface between the computer hardware and software. The CPU 224 may support a time of day and calendar clock 232 for time and data stamping data records.

Also attached to the bus 230 are a number of input/output (I/O) controllers and devices. For example, a serial port 234 might be connected to a local area network (LAN) or other devices requiring serial input/output (I/O) connection, and a parallel port 236 would typically be connected to a printer (not shown). A disk controller 238 provides both input from and output to a hard disk drive 239 and a floppy disk drive 20. A display adapter 240 provides outputs to a color monitor 22 and to the interface electronics 222. A light pen port 242 is connected to light pen 24. Additional controllers may be provided but are optional. For example, an internal modem 244 may connected to a telephone line 245 to provide a communication link to a remote database.

The interface electronics 222 is connected to the internal bus 230 of the computer 220. In practice, the computer 220 is provided with a plurality of "slots" or connectors in which the various adaptor printed circuit boards are inserted to make the connection with the bus 230. The interface electronics 222 is preferably fabricated on a printed circuit board and inserted into one of these available slots to make the connection with the bus 230.

The heart of the electronic interface 222 is the pupil size and location measurement circuitry 246. This circuitry receives an input from a video camera 247 (CCD in FIG. 33). One of the outputs of the display adaptor 240 is connected to an input of the video mixing circuitry 248 in order to generate a "superimpose" signal to the monitor, so that the image produced on the color monitor 22 is a superposition of the video images of the patient's eyes and computer generated text and graphics or markings, such as cross hairs for assisting in the initial positioning of the optical system by the operator.

The automated servo positioning control system described with respect to the actuator assemblies shown in FIG. 35 is controlled by computer generated commands. More particularly, the measurement circuitry 246 provides basic measurement data to the CPU 224 via bus 230, and the CPU 224 performs the necessary calculations required to track the patient's eyes during a test. These calculations result in commands which are communicated over bus 230 to stepper motor drivers 250 to the stepper motors 251. There are six stepper motors, and it will be understood that there is one driver for each servo motor.

During a test, various of the LEDs are controlled by the CPU 224 according to a stored program, and again commands are communicated over bus 230 to LED drivers 252 to turn LEDs 253 on and off. There are fourteen LEDs (eight field or quadrant, two fixation, two infrared pupil illuminators, and two face lamps), and it will be understood that there is one driver for each LED.

Figure 42:
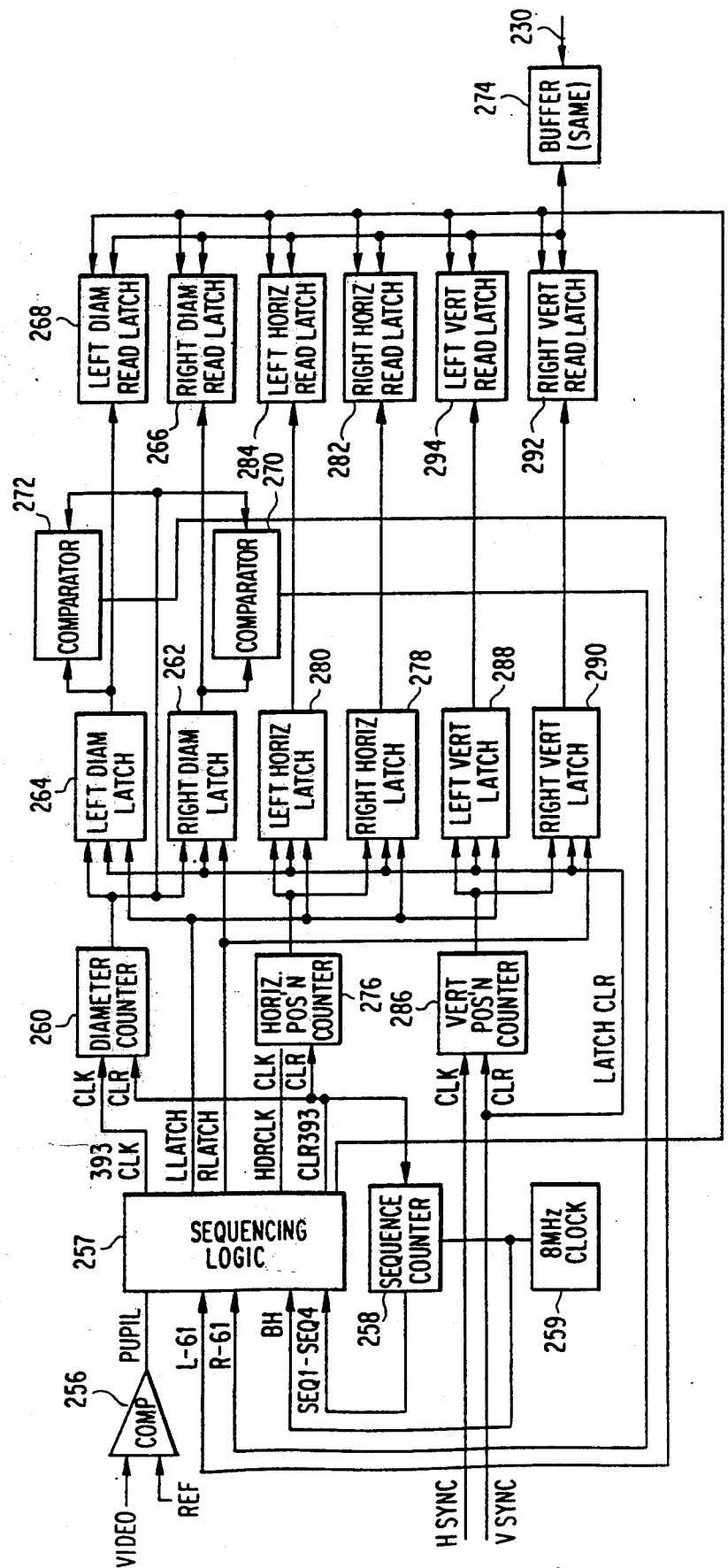
FIG. 42 is a detailed block diagram of a component of the interface electronics shown in FIG. 41.

Referring now to FIG. 42, there is shown in more detail the pupil size and location circuitry 246. The video from camera 247 is supplied to a comparator 256 which receives a reference value corresponding to an expected threshold for the backlit pupil. The comparator 256 provides an output when the scan of the camera is within the pupil area, and this output is supplied to the sequencing logic 257. The sequencing logic 257 steps through its sequence of operations under the control of a sequence counter 258 driven by a clock 259. The output of clock 259 is also supplied directly to the sequencing logic 257 which supplies the clock signal to various counters.

On the leading edge of the output from comparator 256, the sequencing logic enables diameter counter 260 which counts clock pulses from sequencing logic 257. On the trailing edge of the output from comparator 256, the sequencing logic disables diameter counter 260 so that the count in this counter is proportional to the length of a chord corresponding to a scan of the camera 247 across the patient's pupil. The first such count on a scan will be for the patient's right pupil. If the count is greater than the previous value in 262, the count in diameter counter 260 is latched into right diameter latch 262. Next, diameter counter 262 is reset and the camera will scan across the patient's left pupil and a count will be accumulated in diameter counter 260 proportional to the length of the chord scanned. If the count is greater than the previous count in 264, this count is latched into left diameter latch 264. The diameter counter 260 is again reset.

At the completion of a vertical scan, corresponding to a vertical sync pulse from the video camera 247, the counts latched into right and left diameter latches 262 and 264 are transferred to right and left read latches 266 and 268, respectively. Also, at the beginning of each horizontal scan of the video camera 247, the sequencing logic 257 resets horizontal position counter 276 which starts counting. On the first leading edge of an output from comparator 256, the sequencing logic disables counter 276. At the end of this half scan, the count in counter 276 is latched into right horizontal latch 278 if and only if the diameter count is greater than the count stored in latch 262. Counter 276 is then reset and re-enabled. On the second leading edge of an output from comparator 256, the sequencing logic disables counter 276 again. The count in counter 276 is latched into left horizontal latch 280 if and only if the diameter count is greater than the count in latch 264. The counts in these two latches are transferred to right and left horizontal read latches 282 and 284, respectively, on the vertical sync.

When the right and left pupil diameters are detected, then the counts in the right and left horizontal read latches 282 and 284 correspond to the horizontal positions of the left edges of the two pupils. By simply dividing the diameters in half and adding that value to the horizontal positions, the CPU 224 determines the horizontal centers of each of the right and left pupils. This information is used by CPU 224 for horizontal tracking.

Now, it is only necessary to determine the vertical centers of the right and left pupils. This is done by the vertical position counter 286 which is cleared by the vertical sync pulse from the video camera 247 and counts the horizontal sync pulses. The sequencing logic 257 causes the contents of the vertical counter 286 to be latched into right vertical latch 288 whenever a new diameter count is latched into latch 262 and into the left vertical latch 290 whenever a new diameter count is latched into latch 264. The contents of these latches are latched into right and left vertical read latches 292 and 294, respectively, at the vertical sync pulse. The content of the right vertical read latch 292 is a measure of the vertical center of the right pupil. Likewise, the content of the left vertical read latch 294 is a measure of the vertical center of the left pupil. These values are used by the CPU 224 for vertical tracking.

The pupil size and location measured by the pupil size and location measurement circuit 246 is supplied to the CPU 224 which generates the tracking commands used to control the horizontal and vertical stepper motors 251. In addition to tracking the patient's pupils, the CPU 224 also automatically focuses the images of the patient's pupils. The focusing algorithm used is best explained by reference to FIG. 43 which shows a representation of the patient's pupils 295 and 296 as scanned by the television camera and a graph of the analog video line for a scan across the diameters of the patient's pupils. It will be observed that the video line has positive going pulses 297 and 298 corresponding to scans across the diameters of the pupils 295 and 296, respectively. FIG. 43A shows an enlarged view of the leading edge of one of the pulses. This leading edge will have a somewhat shallow slope, as represented by the dashed line 299, when the image is out of focus but a rather steep slope, as represented by the solid line 300, when the image is in focus. Thus, the CPU 224 adjusts the positions of the left and right actuator assemblies to maximize the slopes of the signals corresponding to the left and right pupils, respectively, by generating commands to the focusing stepper motors 251. These slopes are evaluated by setting two different values for the video threshold and observing the magnitude of the difference in measured pupil diameters.

Besides focusing and tracking the images of the patient's eyes, the CPU 224 also runs the selected tests by generating commands to the LED drivers 252. The data produced in the form of pupil size measurement is stored to RAM 226. Once a test is completed, the CPU 224 must then analyze the data generated during the test and provide video and printed outputs to operator and-/or store the data to floppy disk. All this is controlled by the computer software.

Computer/Software Subsystem

As mentioned, the computer 220 shown in FIG. 41 can be an IBM PC/XT computer or equivalent. The computer is programmed in one of the many languages supported by that computer. In the preferred embodiment, the computer is programmed in the C++ language which is an object-oriented programming language based on the C programming language originally developed by Bell Telephone Laboratories. The computer/software subsystem has already been partially described by reference to the screens presented to the user during the operation of the system as illustrated in FIGS. 2 to 32.

Figure 44:
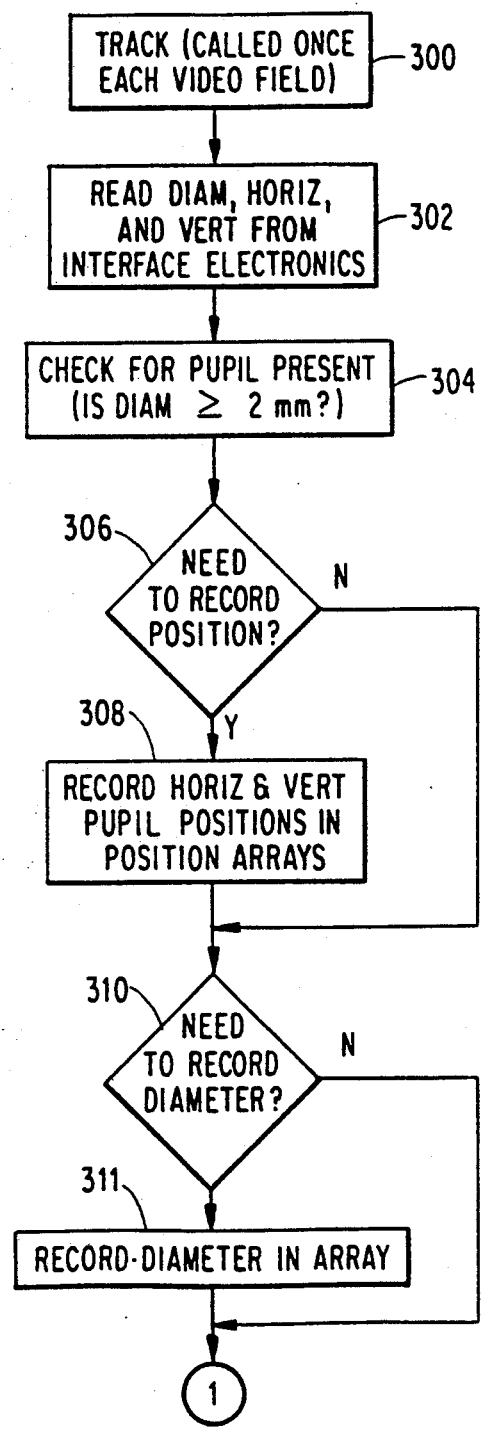
FIGS. 44, 45 and 46, taken together, are a flow diagram showing the logic of the data acquisition and tracking software.
Figure 45:
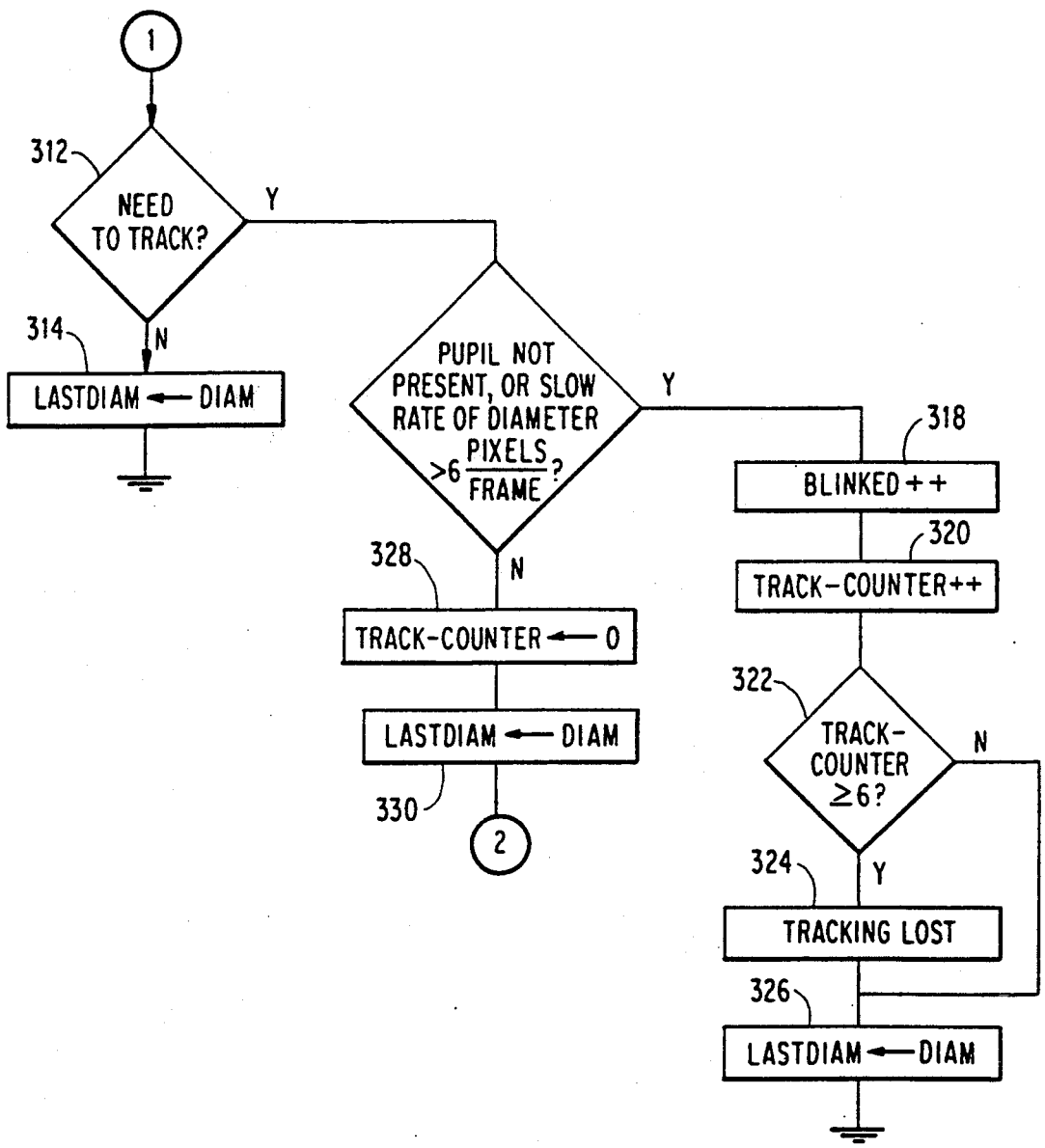
Figure 46:
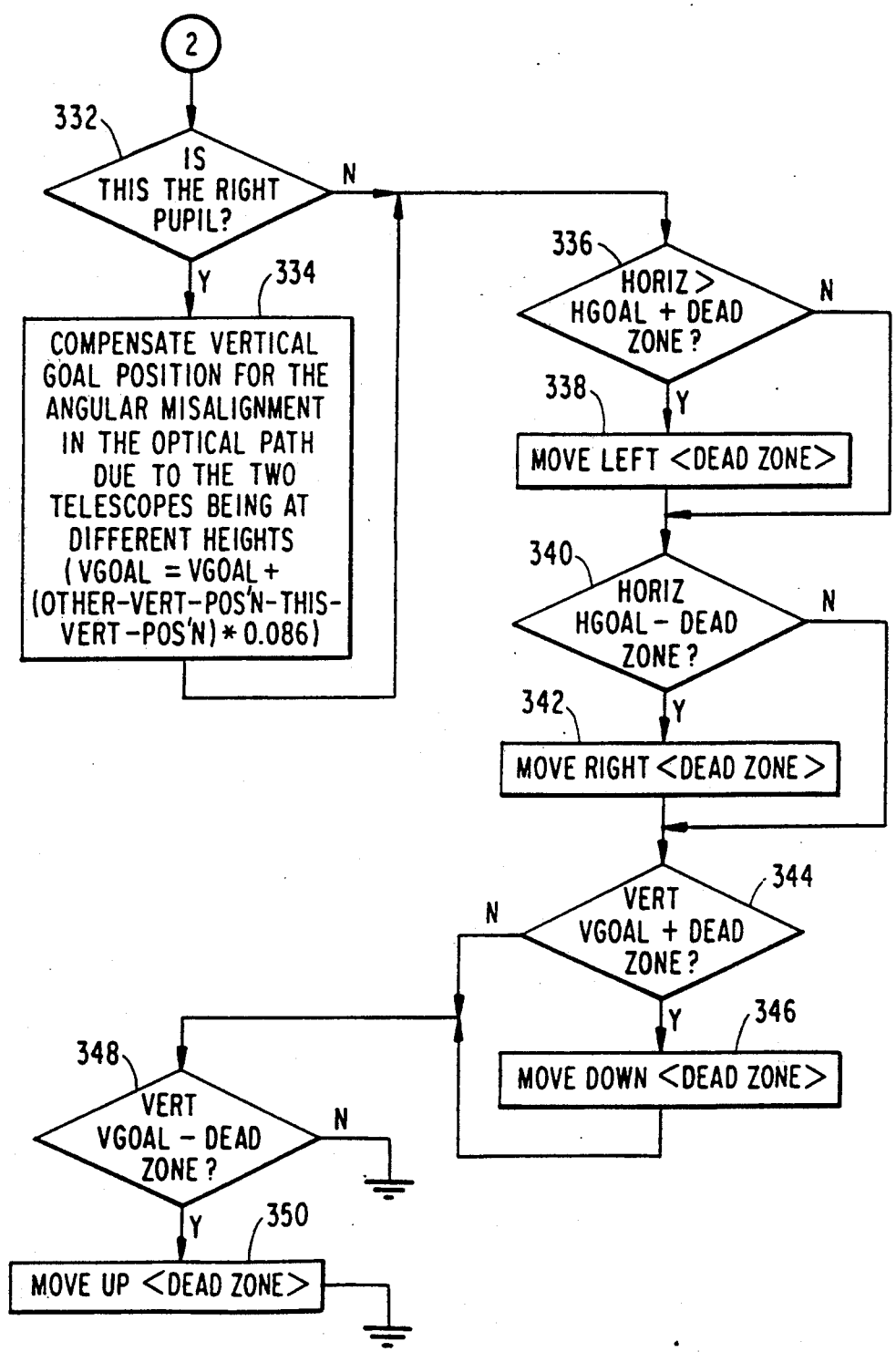

FIGS. 44, 45 and 46 show the logic of the data acquisition and tracking software. The procedure is called once each video field, as indicated by function block 300 in FIG. 44. When the procedure is called, the values of the pupil diameter and horizontal and vertical measurements are read from the electronic interface in function block 302. A check is made in function block 304 for the presence of a pupil. This is a threshold test which, in this case, requires the pupil diameter to be greater than or equal to 2 mm. A test is then made in decision block 306 to determine if the pupil position should be recorded. If so, the horizontal and vertical pupil positions are recorded in position arrays in function block 308. If not, or after the positions are recorded, a test is made in decision block 310 to determine if the diameter should be recorded. If so, that value is recorded in a diameter array in block 311. If not, or after the diameter is recorded, a test is made in decision block 312 in FIG. 45 to determine if tracking is required. If not, the last diameter is set to the present diameter in function block 314, and the process ends.

If tracking is required as determined by the test made in decision block 312, then a further test is made in decision block 316 to determine if the pupil is not present or if the slew rate of the pupil diameter is greater than six pixels per frame. If so, a blink counter is incremented in function block 318 and a track counter is incremented in function block 320. A test is then made in decision block 322 to determine if the count in the track counter is equal to or greater than six. If so, the tracking is declared lost in function block 324; otherwise, or if tracking is lost, the last diameter is set to the present diameter in function block 326, and the process ends for this video field.

Assuming that the test in decision block 316 is negative, the track counter is reset in function block 328 and the last diameter is set to the present diameter 330 before control goes to decision block 332 in FIG. 46. In decision block 332, a test is made to determine if the right pupil is being tracked. If so, the vertical goal position is compensated for the angular misalignment in the optical path due to the two telescopes being at different heights, as indicated in function block 334. If it is the left pupil or after the compensation is made for the right pupil, a test is made in decision block 336 to determine if the horizontal position is greater than the horizontal goal plus a dead zone. If so, the tracking system is moved left in function block 338. Then a test is made in decision block 340 to determine if the horizontal position is less than the horizontal goal minus a dead zone. If so, the tracking system is moved right in function block 342. Next, a test is made in decision block 344 to determine if the vertical position is greater than the vertical goal plus a dead zone. If so, the tracking system is moved down in function block 346. Then a test is made in decision block 348 to determine if the vertical position is less than the vertical goal minus a dead zone. If so, the tracking system is moved up in function block 350, and the process ends for this video field.

In the flow diagrams of FIGS. 47 to 55 which are described next, a rectangular box is a program action that occurs without user intervention, a circle is a program test for condition that occurs without user intervention, and a diamond shape signifies that user input is required before the program continues. Except for the flow diagram of FIG. 47, these flow diagrams illustrate the logic of the user menu selection software. It will be observed that each of the flow diagrams of FIGS. 48 to 55 begin with a command from the command bar 32. The main and submenu items may be either grey or not. Grey signifies that the item is inactive (nonresponsive) because it is inappropriate. A variable, State, determines whether greyable items are grey or not. Greyable items and values for State are as follows:

| State | BEGIN | DISPLAY | Save | Comment |
|---|---|---|---|---|
| 0 | grey | grey | grey | Initial condition and condition after saving or discarding results. |
| 1 | active | grey | grey | Tests have been defined, but none have been run. |
| 2 | grey | active | active | Tests have been run and no new tests defined. |
| 3 | active | active | active | Tests have been run and new tests defined. |
| 4 | grey | active | grey | Tests have been recalled from disk. |

Referring first to FIG. 47, upon startup and before the main menu is active, the user is prompted in block 352 to verify that the computer clock has the correct time. If the time is correct, State is set to 0 in function block 354, and the process ends. If the time is not correct, the user is prompted in block 356 to set the clock time and date. The system checks the user's input in block to determine if the setting is valid. If it is, the process loops back to block 352; otherwise, an error message is displayed in block 360, and control loops back to block 356. In the flow diagram shown in FIG. 48, the command PATIENT is selected. This command allows the user to enter the patient identification (ID) number. When the PATIENT command is selected, the system first checks in block 362 to determine if both live data and ID number are present. If so, the user is prompted in block 364 to select whether the data is to be saved. If the user selects to save the data, the data is written to disk in block 366, and the data is then discarded in block 368 before the State is set to 0 in block 370. The system then checks in block 372 to determine if recalled data is present. If so, that data is discarded in block 374 before the State is set to 0 in block 376. The user is then prompted in block 378 to enter the patient's ID number. The user can either enter an ID number or cancel the operation. If an ID number is entered, the system checks in block 379 to determine if any tests have been run for this ID number. If not, the user is prompted in block 380 to select single or both eye testing and to select manual or auto tracking. At this point, the ID line at the top of the screen is reset in block 382, and the process ends.

Figure 49:
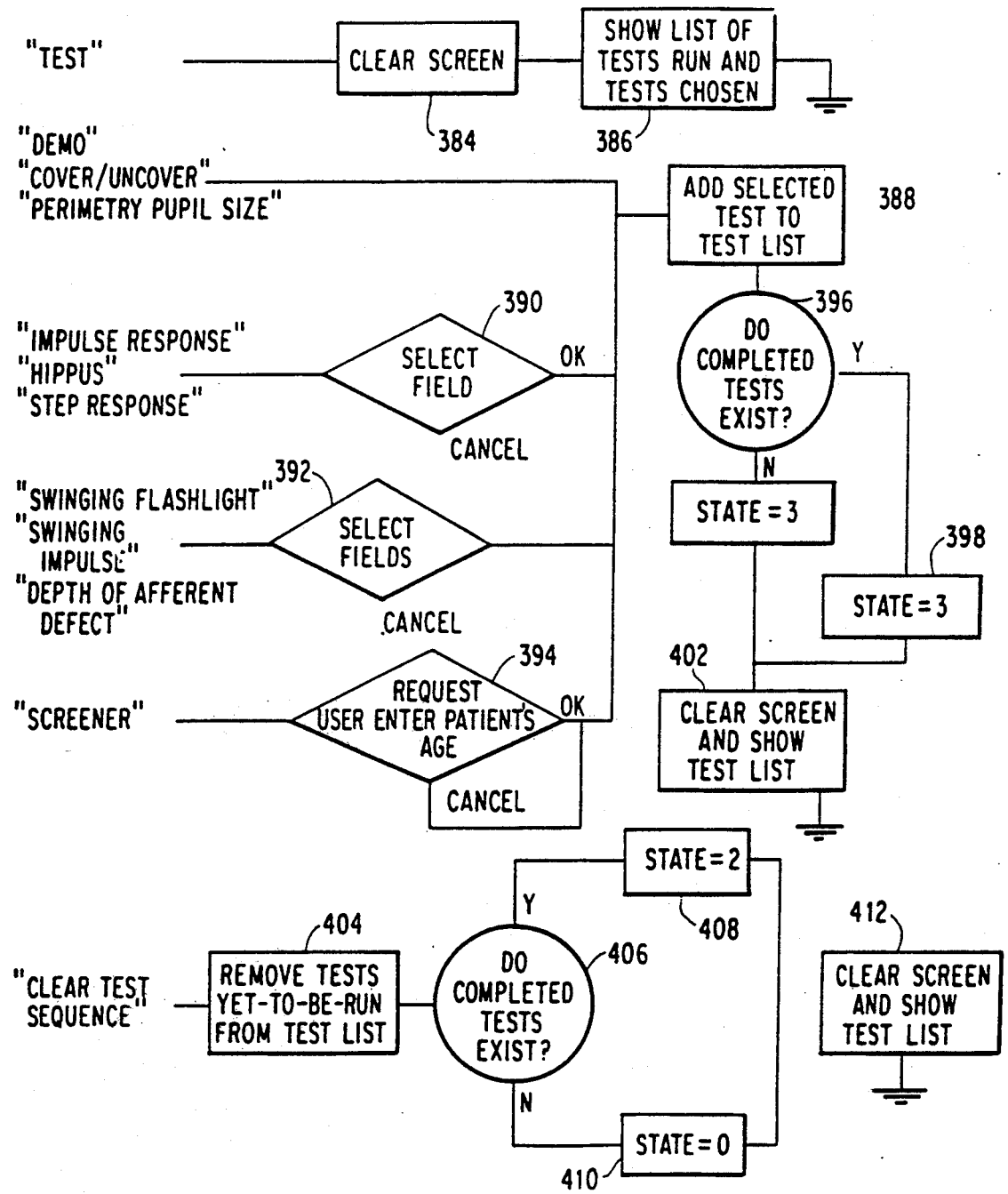

Next, in FIG. 49, the TEST command is used to select test to run. If the TEST command is used without selecting any submenu items, the process begins in block 384 by clearing the screen and then showing the list of test run and tests chosen in block 386. If the demo, cover/uncover or perimetry pupil size tests are selected from the TEST submenu, that test is added to the test list in block 388. If the impulse response, hippus or step response tests are selected from the TEST submenu, then the user is prompted in block 390 to select the field before the test is added to the test list. If the swinging flashlight, swinging impulse or depth of afferent defect tests are selected from the TEST submenu, then the user is again prompted in block 392 to select the field before the test is added to the test list. Finally, if the screener is selected from the TEST submenu, the user is prompted in block 394 to enter the patient's age before the tests of the screener are added to the test list. After tests have been added to the list, the system determines in block 396 whether completed tests exist. If so, the State is set to 3 in block 398; otherwise, the State is set to 1 in block 400. Then the screen is cleared and the test list is displayed in block 402.

The user has another option under the TEST command, and that is to clear the test sequence. If this is selected, then the tests which have not been run are removed from the test list in block 404. The system then checks in block 406 to see if completed tests exist. If so, the State is set to 2 in block 408; otherwise, the State is set to 0 in block 410. Then the screen is cleared and the test list is displayed in block 412.

Figure 50:
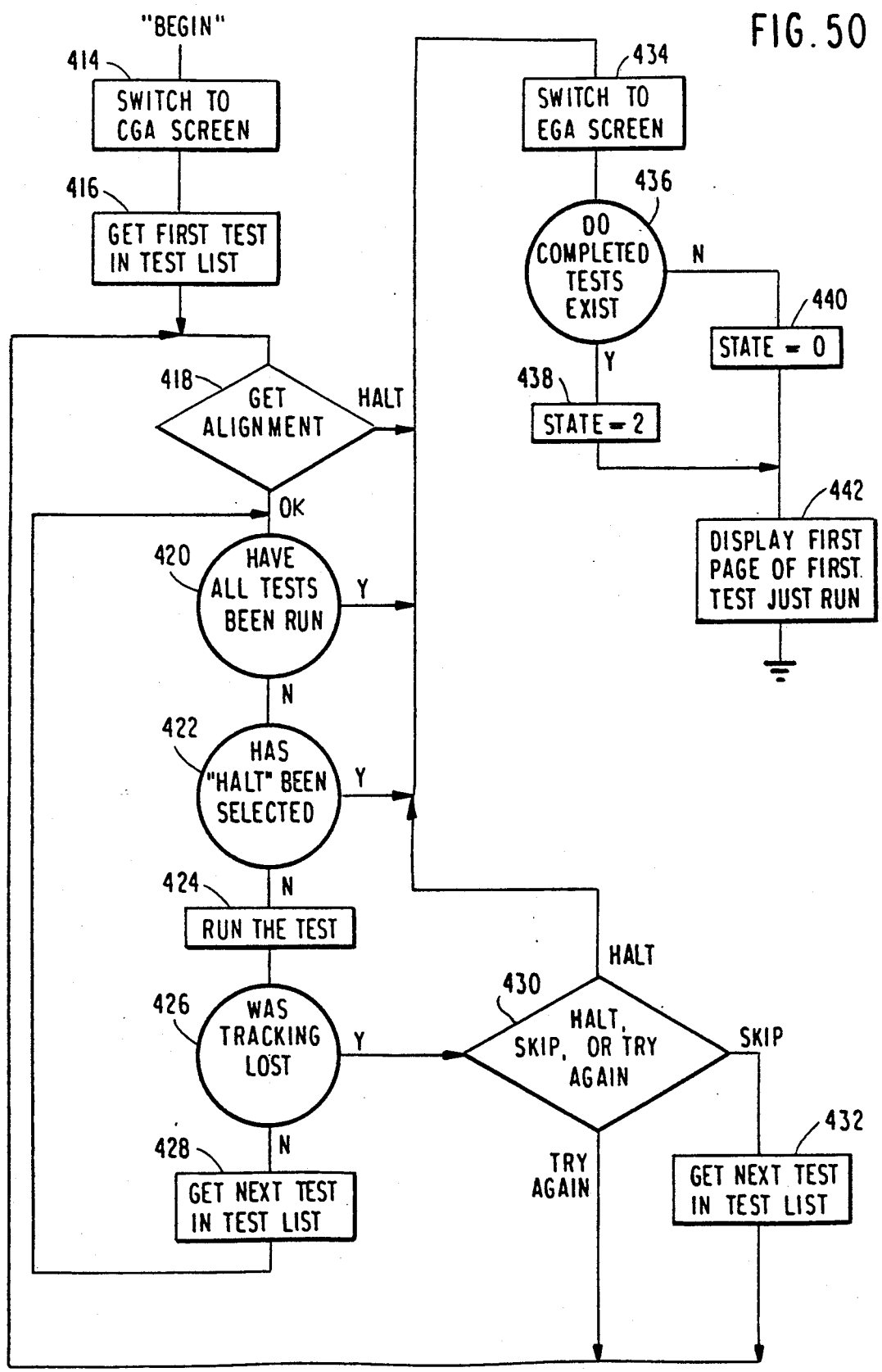

In FIG. 50, the BEGIN command is selected. This causes the system to switch to the CGA screen in block 414. Then the first test in the test list is retrieved in block 416. The user is then prompted in block 418 to make the manual alignment. When the user indicates that alignment has been made, the system checks in block 420 to determine if all tests have been run. If not, the system checks in block 422 to determine if "halt" has been selected by the user. If not, the test is run in block 424. During the test, the system constantly checks in block 426 to determine if tracking was lost. If not, at the completion of the test, the next test in the list of tests is retrieved in block 428, and control loops back to block 420. If tracking is lost during a test, the user is prompted in block 430 to select among the options of halt, skip or try again. If the latter is selected, then control loops back to block 418. If skip is selected, the next test in the test list is retrieved in block 432 before control loops back to block 418. If halt is selected or if either of the system tests made in block 420 or 422 are true, the system switches back to the EGA screen in block 434. The system then determines in block 436 if any completed tests exist. If so, the State is set to 2 in block 438; otherwise, the State is set to 0 in block 440. Then the system displays in block 442 the data from the first test in the list of tests just run.

In FIG. 51 the DISPLAY command is selected. Although individual results are displayed automatically after each test, the operator can use this command to go back and review previous results. When DISPLAY is selected, the screen is cleared in block 444 and then, in block 446, the current page of the current test is displayed.

Figure 52B:
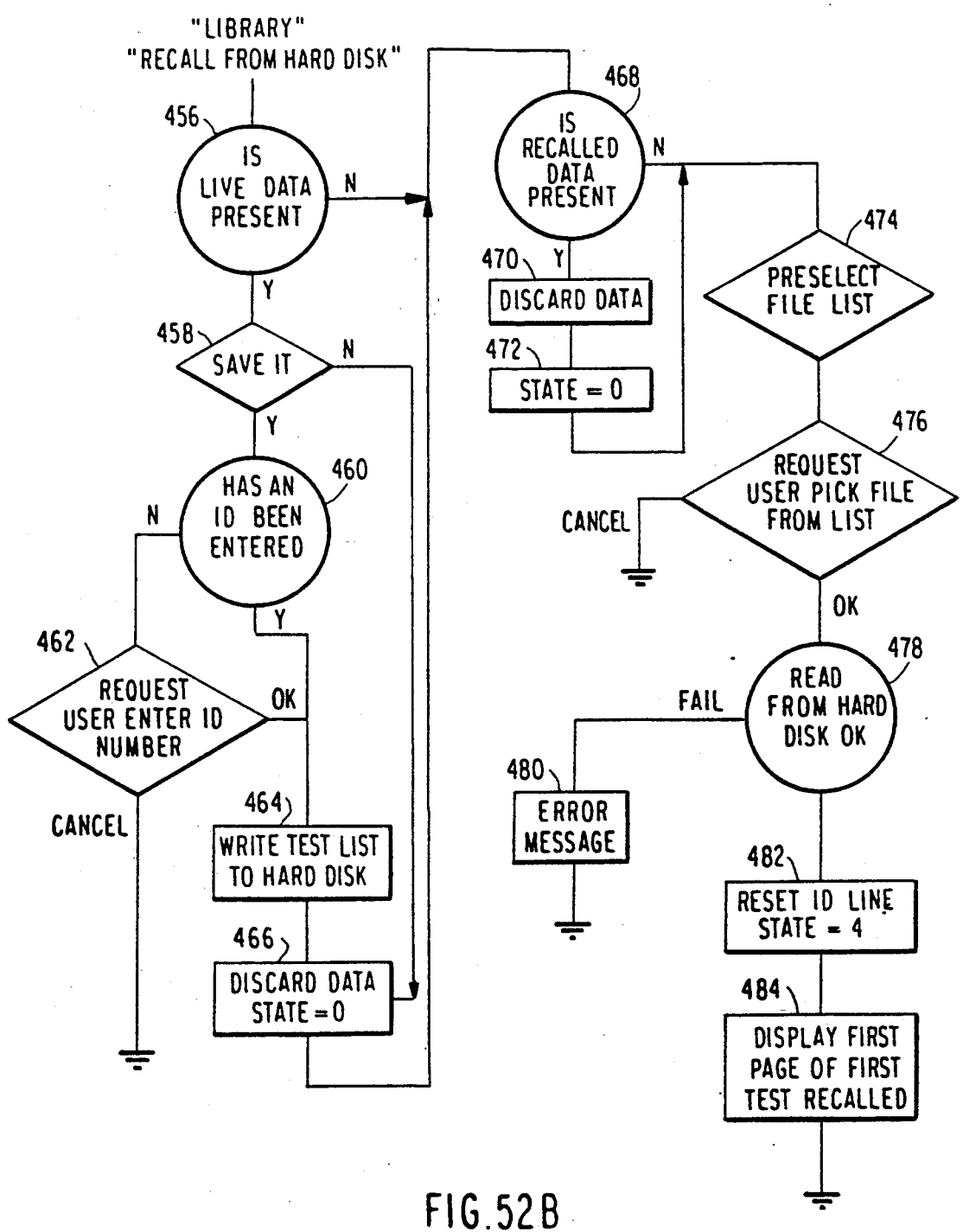

The LIBRARY command logic is shown in FIGS. 52A to 52D. This command allows the user to (1) save the results from all tests that have been run satisfactorily to disk, (2) recall previous test results for display, (3) delete previous test results from disk, or (4) terminate the program. When the LIBRARY command is selected, the operator may select from these four options. If the save to disk option is selected, as shown in FIG. 52A, the system checks in block 448 to determine if an ID has been entered. If not, the user is prompted in block 450 to enter an ID number. Then, in block 452, the data is saved to disk and, in block 454, the State is set to 0 before the process ends.

If the user selects the recall from disk option as shown in FIG. 52B, then the system checks in block 456 to determine if live data is present. If so, the user is prompted in block 458 whether the data is to be saved. If the user elects to save the data, the system makes a further check in block 460 to determine if an ID has been entered. If not, the user is prompted in block 462 to enter an ID number. Then, in block 464, the data is written to disk and, in block 466, the State is set to 0. At this point, or if live data is not present, the system checks in block 468 to determine if recalled data is present. If so, the data is discarded in block 470 before the State is set to 0 in block 472. Now, the user is prompted in block 474 whether a preselect file list is to be displayed, and if so, the user is then prompted in block 476 to select the desired file from the list. Then the system attempts to read the file from disk in block 478. If the attempt fails, an error message is displayed in block 480 before the process ends. If the attempt is successful, then the ID line is reset and the State is set to 4 in block 482, and the first page of the first test recalled is displayed in block 484.

If the user selects the third LIBRARY option as shown in FIG. 52C, the user is prompted in block 486 whether the preselect file list is to be displayed. If so, the user is prompted in block 488 to pick a file from the list to be deleted. The selected file is deleted in block 490, and the process loops back to block 488 until the user selects the cancel button indicating that all files to be deleted have been deleted.

If the user selects the shut down option of the LIBRARY command as shown in FIG. 52D, the system first checks in block 492 to determine if live data is present. If so, the user is prompted in block 494 whether the data is to be saved. If so, the system checks in block 496 whether an ID number has been entered. If not, the user is prompted in block 498 to enter an ID number. Then the system writes the data to disk in block 500 and, in block 502, the data is discarded and the State set to 0 before the program is terminated in block 504.

Figure 53:
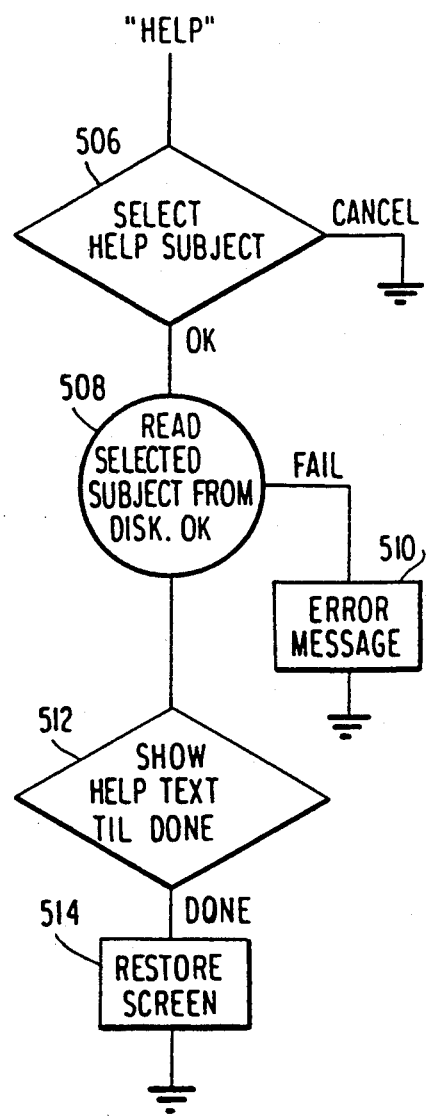

The HELP command shown in FIG. 53 can be selected during any of the other operations. It allows the user to select a topic and read a brief explanation of the topic and then return to whatever was present on the screen. If HELP is selected by the user, the user is prompted in block 506 to select a help subject. Once a topic has been selected, the system attempts to read the selected topic from disk. If the attempt fails, an error message is displayed in block 510. If the attempt is successful, then the help text is displayed for the user in block 512 until the user indicates that they are done with the text. At that point, the system restores the original screen in block 514.

Figure 54:
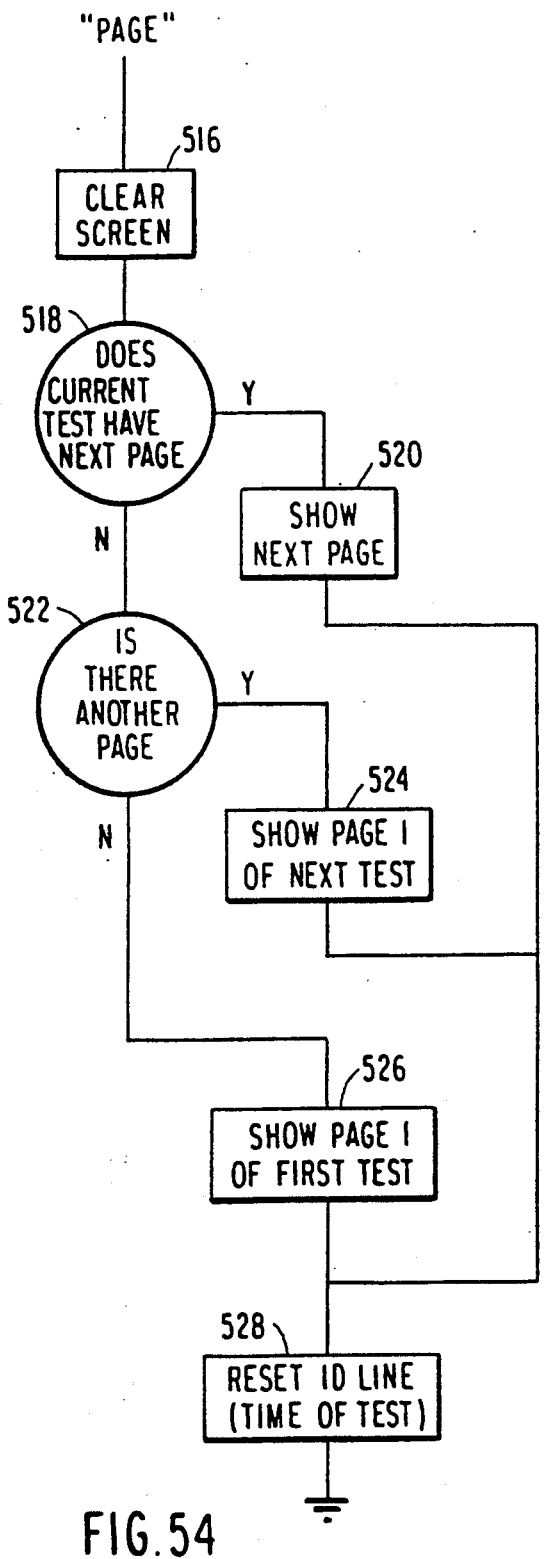
Figure 55:
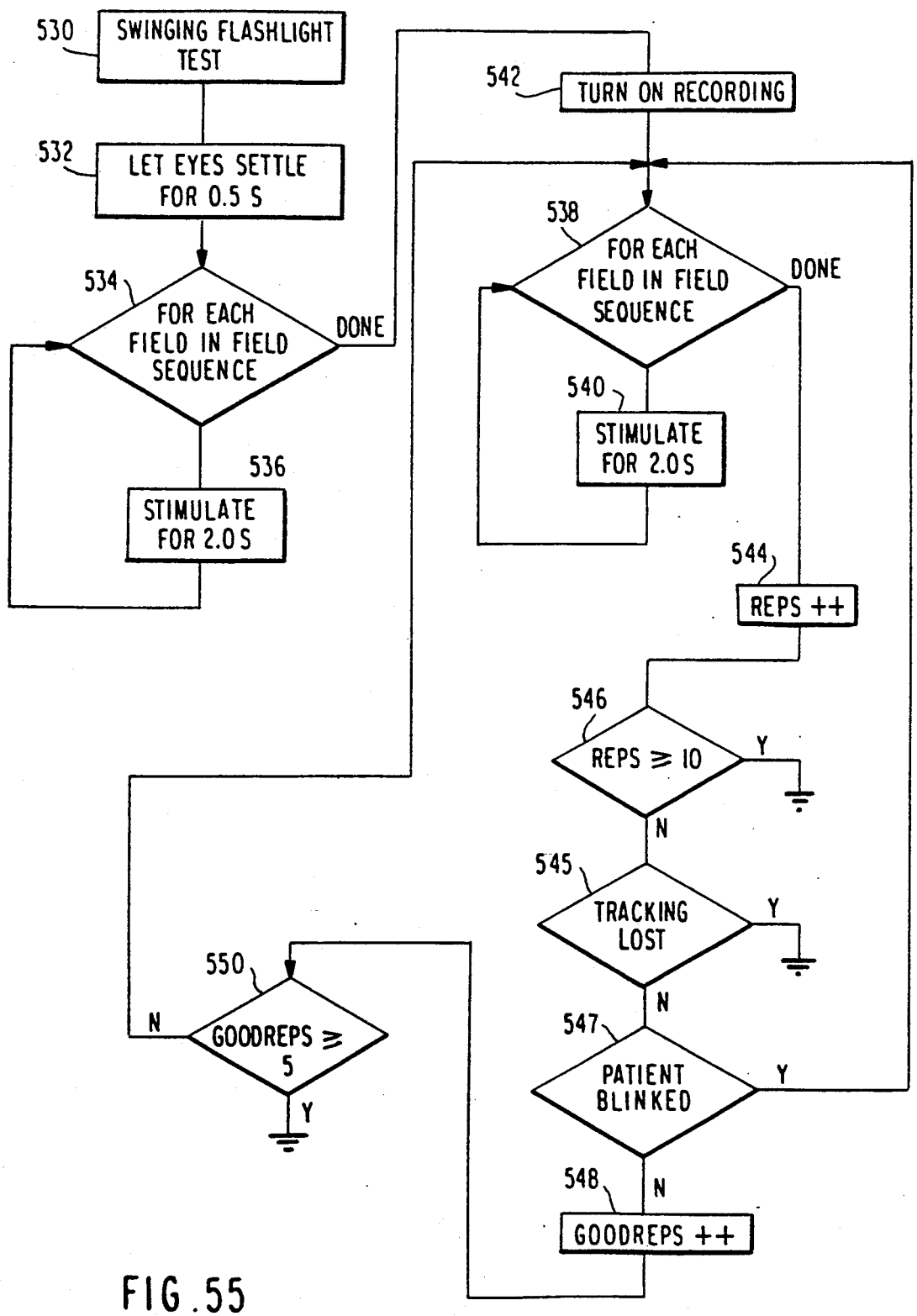

When the user selects the PAGE command as shown in FIG. 54, the system first clears the screen in block 516 before checking to determine if the current test has a next page in block 518. If there is a next page, it is displayed in block 520; otherwise, the system checks if there is another test in block 522. If there is, the first page of the next test is shown in block 524; otherwise, page one of the first test is shown in block 526. After each of these displays, the system resets the time of test in the ID line in block 528.

The tests that can be selected (see the flow diagram of FIG. 49) are themselves controlled by software. The logic of the software for the swinging flashlight test is shown by the flow diagram of FIG. 55. When this test is selected from the test list in block 530, the system lets the patient's eyes settle for half a second in block 532 before beginning the control sequence in block 534. In this sequence, each field in the field sequence is stimulated for two seconds in block 536 until the sequence is completed. This first sequence is not recorded but is used to accustom the patient to the test. The process is then repeated in blocks 538 and 540 after turning on the data recording process in block 542. Each time the sequence is done, a repetition counter is incremented in block 544, and this continues until the number of repetitions is greater than or equal to ten as determined in block 546. During a test, the system checks in block 545 to determine if tracking has been lost. If so, the process stops. The system also checks in block 547 to determine if the patient blinked during the test and, if so, the process loops back to block 538; otherwise, the good repetitions counter is incremented in block 548 and the count is checked in block 550 to determine if there has been at least five good repetitions of the test. If not, control loops back to block 538 to repeat the test.

Figure 56:
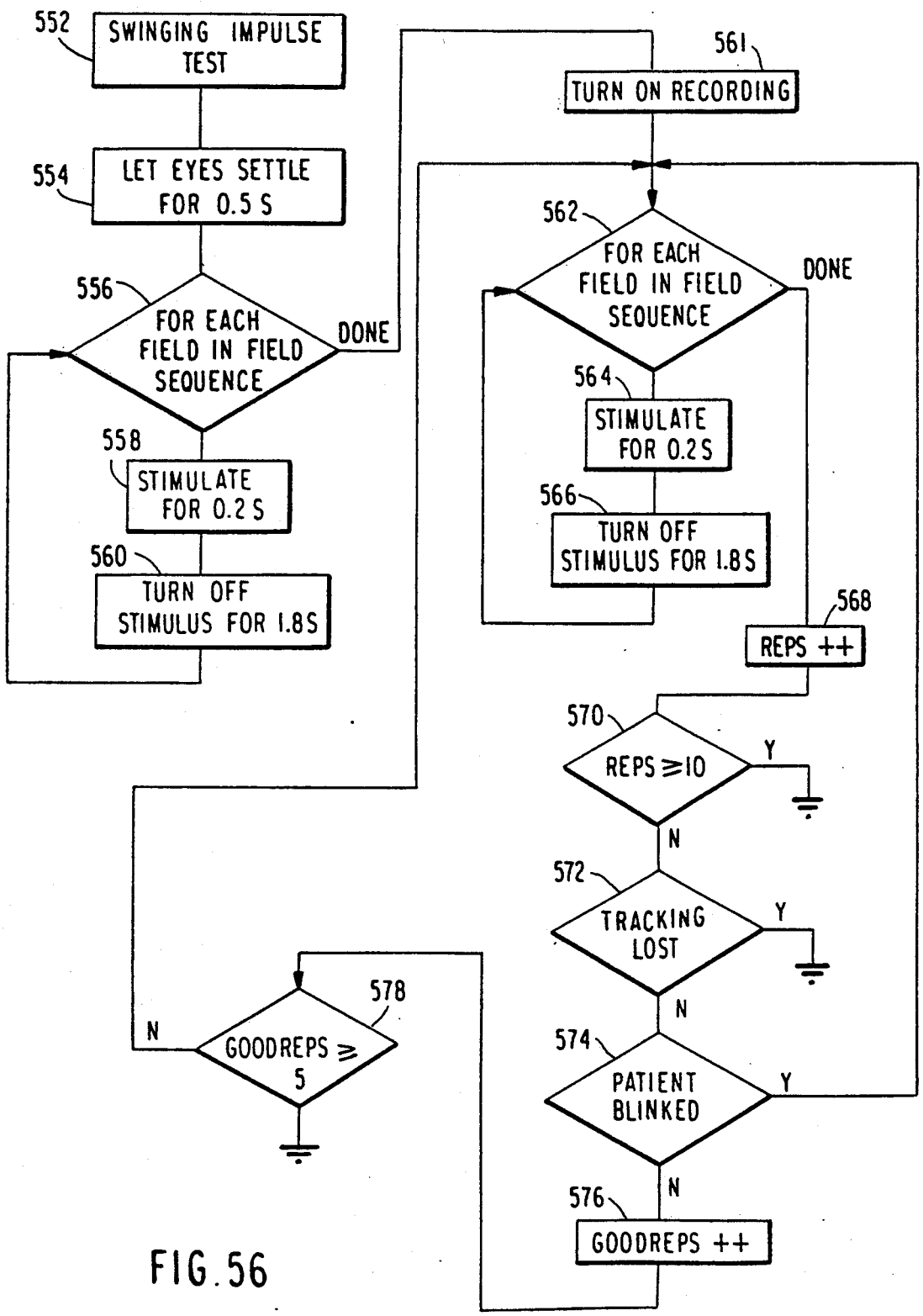

The swinging impulse test is selected in block 552 as shown in FIG. 56. Again, the system lets the patient's eyes settle for half a second in block 554 before the test sequence begins in block 556. In this sequence, the stimulus is for a duration of 0.2 seconds in block 558 with the stimulus turned off for 1.8 seconds in block 560. When the sequence is completed, the data recording is turned on in block 561 and the sequence is repeated in blocks 562, 564 and 566. After each repetition, the repetition counter is incremented by one in block 568 and then the count in the counter is checked in block 570 to determine if it has reached ten. If not, checks are made in blocks 572 and 574 to determine if tracking has been lost or if the patient blinked during the test. If not, the good repetition counter is incremented in block 576 and the count in the counter is checked in block 578 to determine if the number of good repetition is greater than or equal to five. If not, control loops back to block 562.

The hippus test is selected in block 580 in FIG. 57, and the system turns on the stimulus for the selected field(s) for three seconds in block 582. The system immediately starts recording in block 584, and recording continues for nine seconds in block 586.

The perimetry test is selected in block 588 in FIG. 58, and the system turns on the binocular full-field stimulus for two seconds in block 590. The system immediately starts recording in block 592. The system then waits for a third of a second in block 594 and checks in block 596 to determine if the patient blinked. If not, the repetition counter is incremented in block 598 and a check is made in block 600 to determine if the number of repetitions is greater than or equal to six. If not, control loops back to block 594; otherwise, the test ends.

The step response test is selected in block 602 in FIG. 59, and the system lets the patient's eyes settle for one and a half seconds in block 604 before starting recording in block 606. Then the selected fields are stimulated for four seconds in block 608 followed by turning off the stimulus for four seconds in block 610. The repetition counter is incremented in block 612, and the count in the counter is checked in block 614 to determine if the number of repetitions is greater than or equal to eight. If not, the system checks for lost tracking in block 616 and whether the patient blinked in block 618. If not, the good repetitions counter is incremented in block 620 and the count in the counter is checked in block 621 to see if it is greater than or equal to four. If not, control loops back to block 608; otherwise, the test ends.

Figure 60:
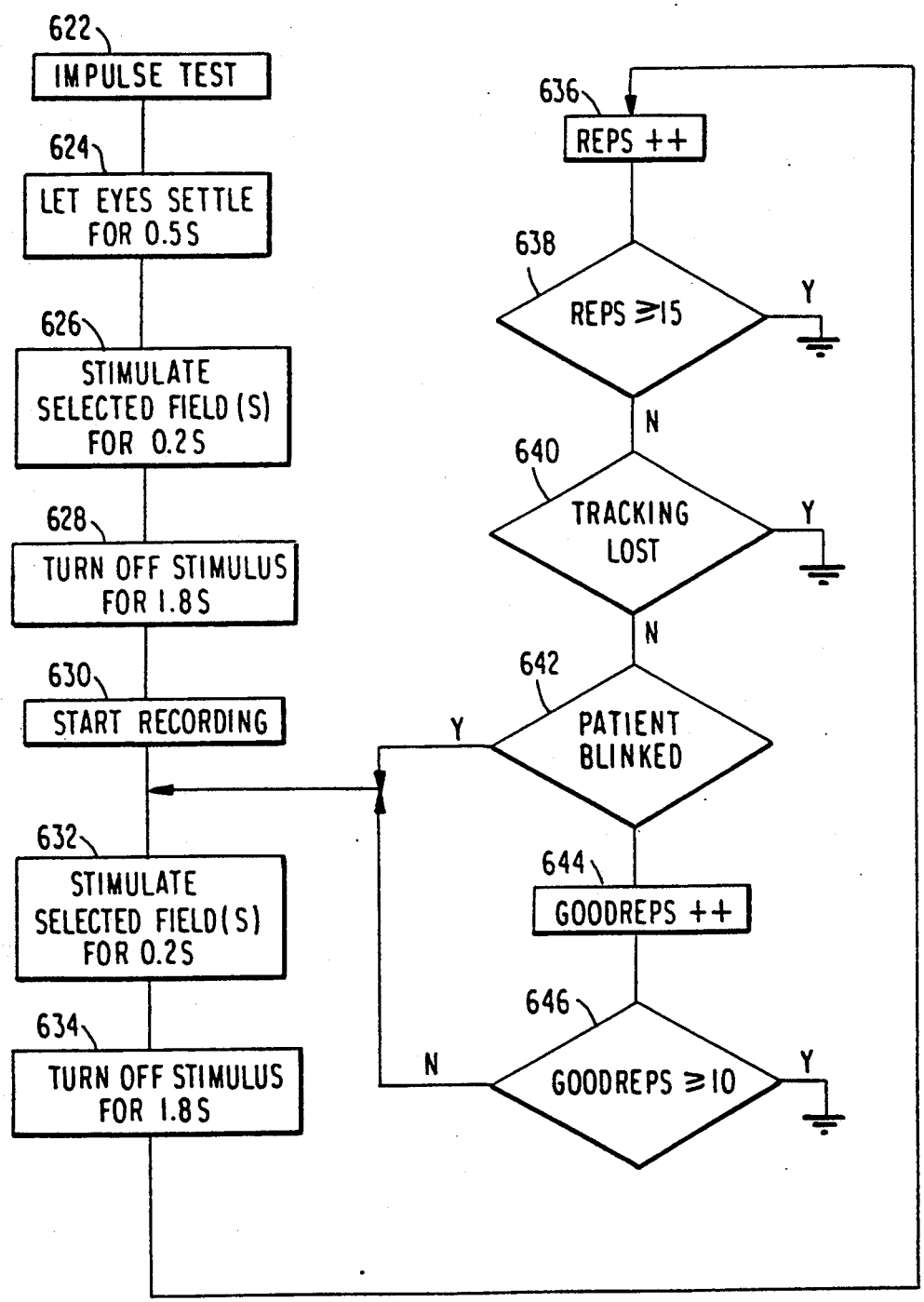

The impulse test is selected in block 622 in FIG. 60, and the system lets the patient's eyes settle for a half second in block 624 before stimulating the selected field(s) for 0.2 seconds in block 626 followed by turning off the stimulus for 1.8 seconds in block 628. At this point, the system turns on recording in block 630 and repeats the test sequence in block 632 and 634. Each time the test sequence is repeated, the repetition counter is incremented in block 636 and the count in the counter is checked in block 638 to determine if it is greater than or equal to fifteen. If not, the system checks to determine if tracking is lost or if the patient blinked during the test 640 and 642. If not, the good repetitions counter is incremented in block 644 and the count is checked in block 646 to determine if there have been at least ten good repetitions. If not, control loops back to block 632; otherwise, the test ends.

Figure 61A:
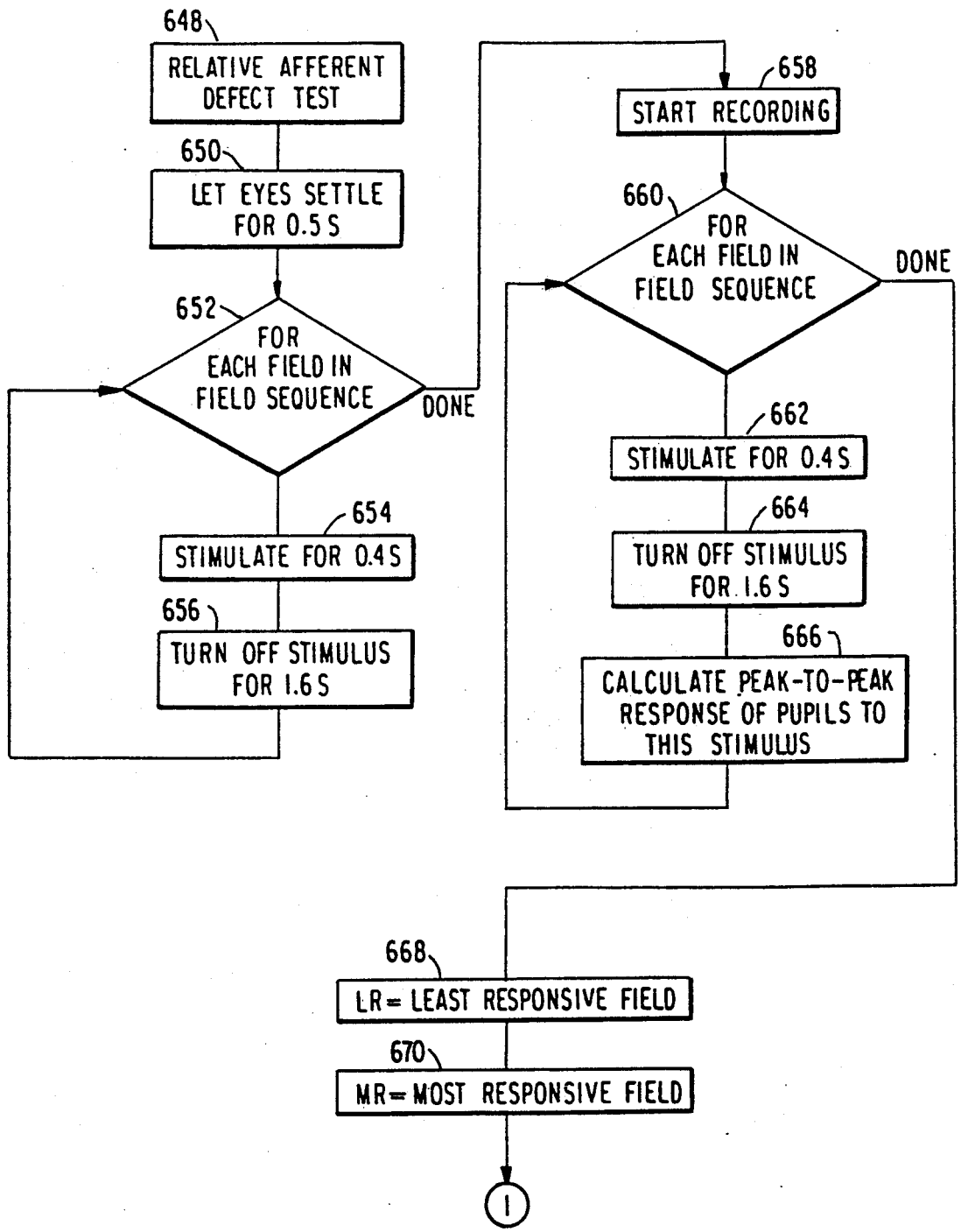
Figure 61:
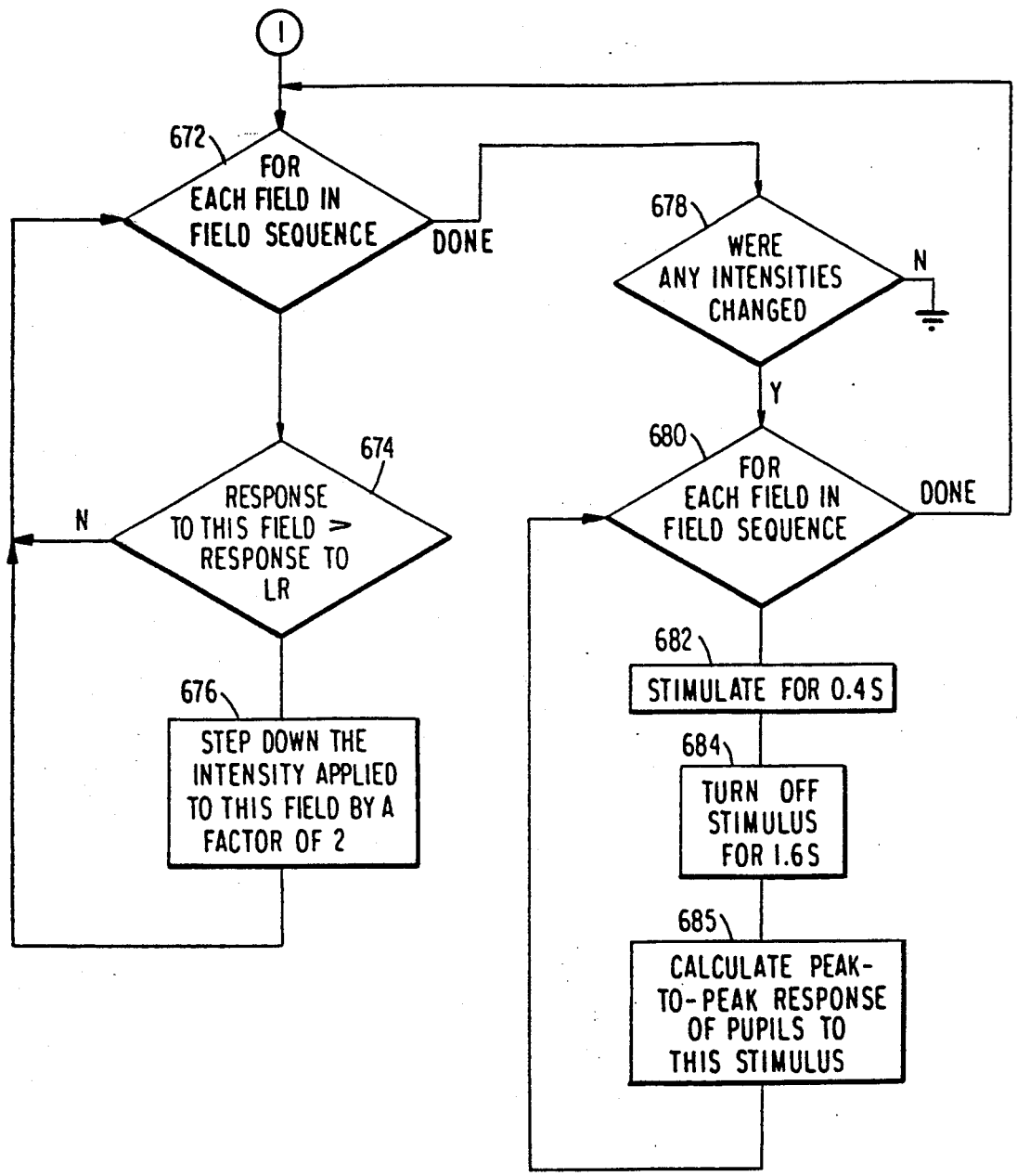

The relative afferent defect test is selected in block 648 in FIG. 61A, and the system first lets the patient's eyes settle for a half second in block 650 before beginning the test sequence in block 652. In this sequence, each field in the field sequence is stimulated for 0.4 seconds in block 654 followed by turning off the stimulus for 1.6 seconds in block 656. At this point, the system turns on the data recording in block 658 and the test sequence is repeated in block 660, 662, and 664. After the stimulus sequence for each field, the system calculates in block 666 the peak-to-peak response of the patient's pupils to the stimulus. When the test sequence is finished, the least responsive field is recorded in block 668 and the most responsive field is recorded in block 670. Then, in FIG. 61B, a new test sequence is begun in block 672. For each field, a test is made in block 674 to determine if the response to this field is greater than the least responsive field recorded in block 668. If so, the intensity applied to the field is stepped down by a factor of two in block 676. When the test sequence is completed, a check is made in block 678 to determine if any intensities have changed. If so, a new test sequence is begun in block 680. This test sequence comprising blocks 680, 682, 684 and 685 is like that of the test sequence comprising blocks 660, 662, 664 and 666. When that test sequence is complete, control loops back to block 672, and the process continues until the test in block 678 is negative, at which point the test ends.

Figure 62:
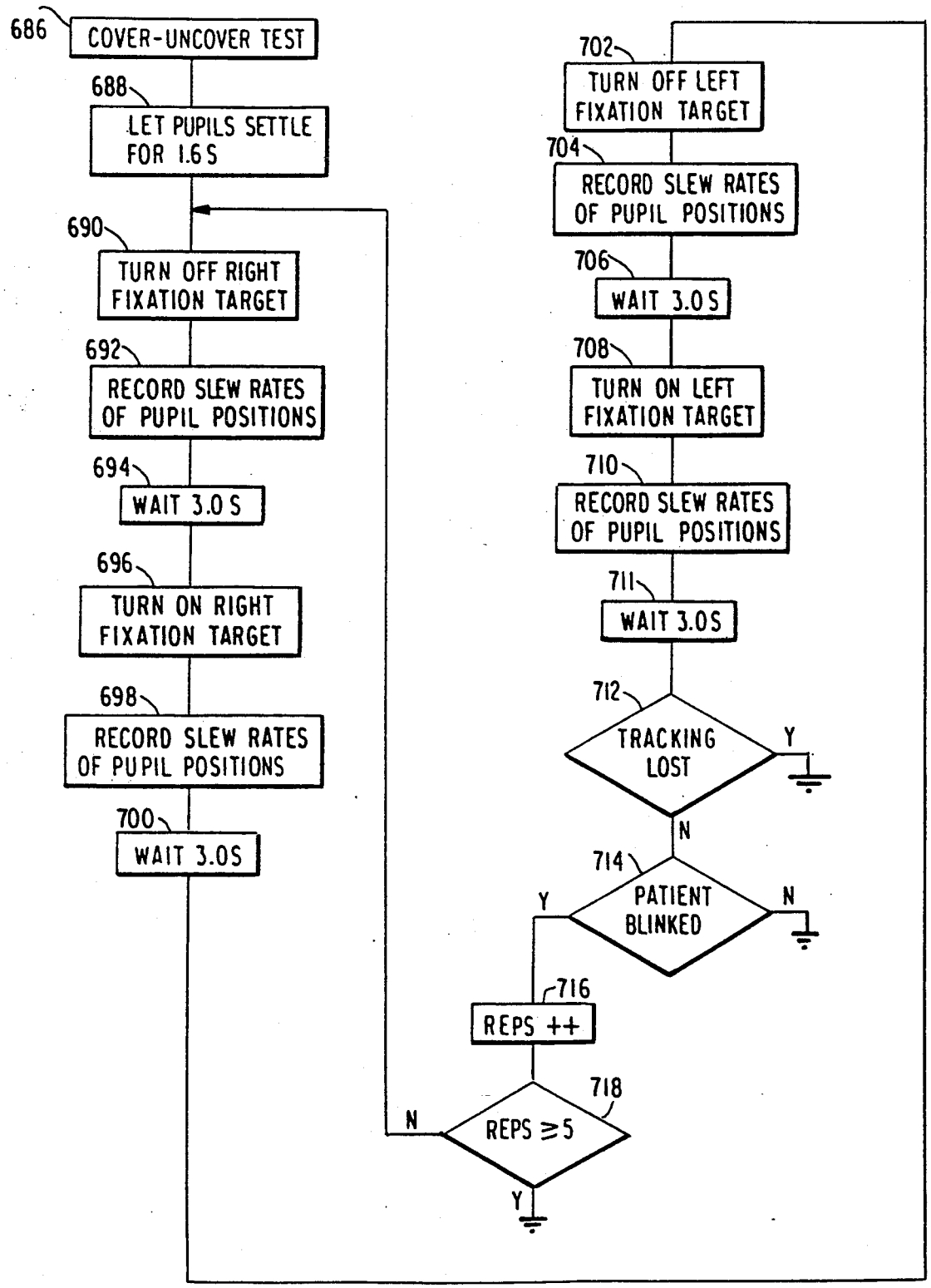

The cover/uncover test is selected in block 686 in FIG. 62, and the system lets the patient's pupils settle for 1.6 seconds in block 688 before turning off the right fixation target 690. Next, the system records slew rates of pupil positions in block 692. After waiting three seconds in block 694, the system turns on the right fixation target in block 696 and records slew rates of pupil positions in block 698. After another wait of three seconds in block 700, the system turns off the left fixation target in block 702 and records slew rates of pupil positions in block 704. After a wait of three seconds in block 706, the left fixation target is turned on in block 708 and the slew rates of pupil positions are recorded in block 710, after which there is another wait of three seconds in block 711. During the test, the system checks to determine if tracking is lost or if the patient blinked in blocks 712 and 714. If tracking is not lost but the patient blinked, the repetition counter is incremented in block 716 and the count in the counter is checked in block 718 to determine if the number of repetitions is greater than five. If not, control goes to block 690 to repeat the test.

Figures 63, 64:
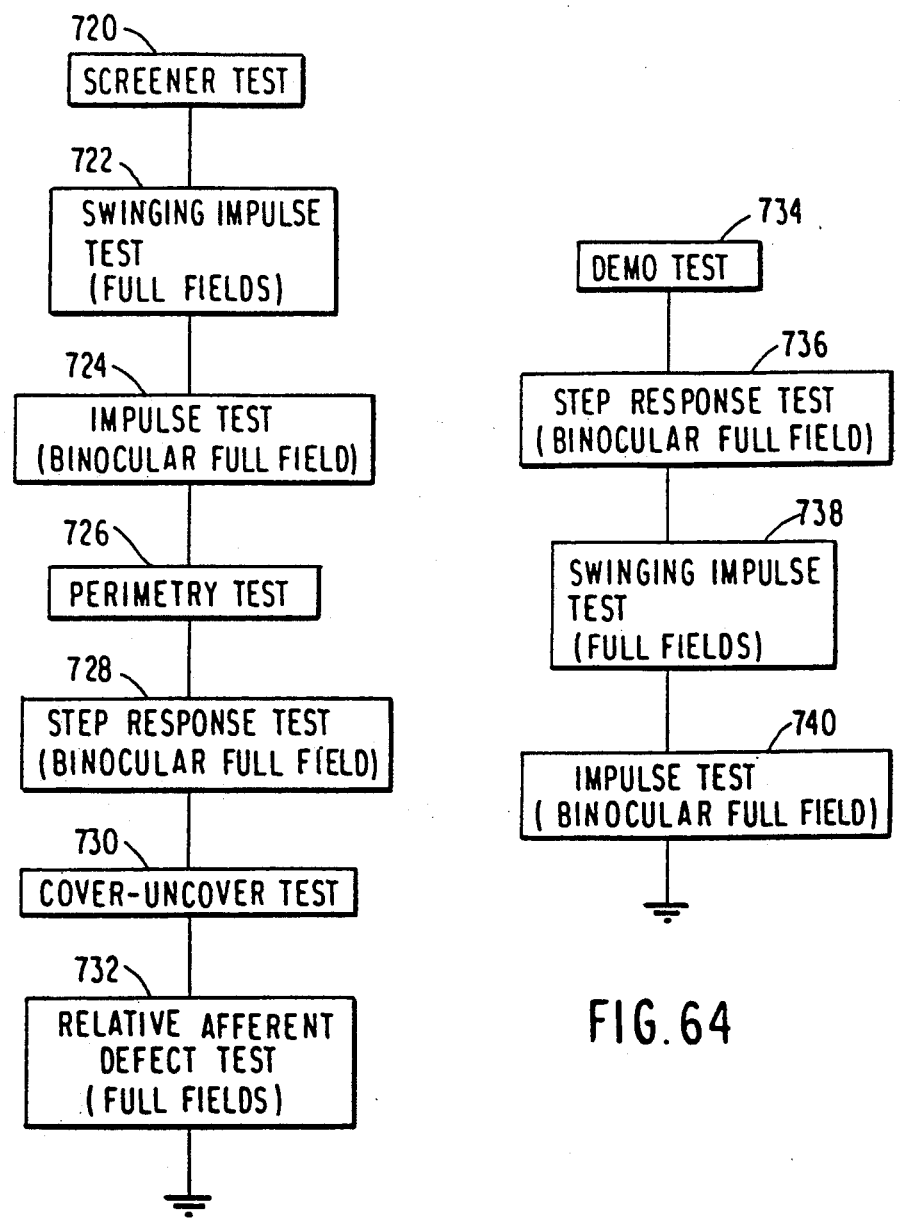

The screener test is selected in block 720 in FIG. 63. This is a series of tests including the swinging impulse test in block 722, the impulse test in block 724, the perimetry test in block 726, the step response test in block 728, the cover/uncover test in block 730, and the relative afferent defect test in block 732. These tests are performed in order as described above.

A demo test is included in the repertoire, and it is selected in block 734 in FIG. 63. When this test is selected, the system performs the step response test in block 736, the swinging impulse test in block 738 and the impulse test in block 740.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. In an ophthalmological instrument for examination of pupillary responses and extrinsic eye muscle balance including pupil imaging optics and a video camera having a photosensitive image plane on which images of a patient's pupils are focused by the pupil imaging optics, pupil measurement apparatus comprising:

an analog comparator connected to receive a video output signal from said video camera, said comparator providing an output when one of said patient's pupils is detected during a horizontal scan by said video camera;

a counter responsive to the output of said comparator for counting clock pulses during said comparator output to provide a measure of a chord of the patient's pupil;

a first latch temporarily storing a count in said counter;

a digital comparator connected to said first latch and to said counter to compare the count in the counter with a previous count stored in said first latch and storing the count in said counter in said first latch when said count is greater than said previous count in said first latch; and a second latch connected to said first latch and storing the count stored in said first latch during a vertical sync pulse of said video camera, said second latch storing a count corresponding to a horizontal measurement the patient's pupil.

2. The pupil measurement apparatus recited in claim further comprising:

a second counter for counting clock pulses from a reference point until an output is received from said analog comparator;

a third latch temporarily storing a count in said second counter and responsive to said digital comparator and storing the count in said second counter when the count in said first counter is greater than the count in said first latch; and a fourth latch connected to said third latch and storing the count of said third latch during said vertical sync pulse, said fourth latch storing a count corresponding to a horizontal measurement of a position of an edge of the patient's pupil along said diameter.

3. The pupil measurement apparatus recited in claim 2 further comprising:

a third counter for counting horizontal synchronization pulses from said video camera from a reference point;

a fifth latch temporarily storing a count in said third counter and responsive to said digital comparator and storing the count in said third counter when the count in said first counter is greater than the count in said first latch; and a sixth latch connected to said fifth latch and storing the count of said fifth latch during said vertical sync pulse, said sixth latch storing a count corresponding to a vertical measurement of a position of the center of the patient's pupil.

4. The pupil measurement apparatus recited in claim 1 wherein said first and second latches respectively store counts corresponding chord and diameter measurements of a patient's left pupil, said apparatus further comprising:

a third latch temporarily storing a count in said counter corresponding to a chord diameter of a patient's right pupil;

a second digital comparator connected to said third latch and to said counter to compare the count in the counter with a previous count stored in said third latch and storing the count in said counter in said third latch when said count is greater than the count in said third latch; and a fourth latch connected to said third latch and storing the count of said third latch during said vertical sync pulse, wherein said fourth latch stores a count corresponding to a diameter measurement of a patient's right pupil.

5. The pupil measurement apparatus recited in claim 4 further comprising means for generating tracking commands based on contents of said second and fourth latches.

6. The pupil measurement apparatus recited in claim 4 further comprising:

a second counter for counting clock pulses from a reference point until outputs are received from said analog comparator;

a fifth latch responsive to said first digital comparator and storing the count in said second counter when the count in said first counter is greater than the count in said first latch;

a sixth latch connected to said fifth latch and storing the count of said fifth latch during said vertical sync pulse, said sixth latch storing a count corresponding to a horizontal measurement of a position of an edge of the patient's left pupil along its diameter;

a seventh latch responsive to said second digital comparator and storing the count in said second counter when the count in said first counter is greater than the count in said third latch; and an eighth latch connected to said seventh latch and storing the count of said seventh latch during said vertical sync pulse, said eighth latch storing a count corresponding to a horizontal measurement of a position of an edge of the patient's right pupil along its diameter.

7. The pupil measurement apparatus recited in claim 6 further comprising means for generating tracking commands based on contents of said second, fourth, sixth and eighth latches.

8. The pupil measurement apparatus recited in claim 6 further comprising:

a third counter for counting horizontal synchronization pulses from said video camera from a reference point;

a ninth latch temporarily storing a count in said third counter and responsive to said first digital comparator and storing the count in said third counter when the count in said first counter is greater than the count in said first latch;

a tenth latch connected to said ninth latch and storing the count of said ninth latch during said vertical sync pulse, said tenth latch storing a count corresponding to a vertical measurement of a position of the center of the patient's left pupil;

an eleventh latch temporarily storing a count in said third counter and responsive to said second digital comparator and storing the count in said third counter when the count in said first counter is greater than the count in said third latch; and a twelfth latch connected to said eleventh latch and storing the count in said eleventh latch during said vertical sync pulse, said twelfth latch storing a count corresponding to a vertical measurement of a position of the center of the patient's right pupil.

9. The pupil measurement apparatus recited in claim 6 further comprising means for reading counts stored in said second, fourth, sixth, eighth, tenth and twelfth latches.

10. The pupil measurement apparatus recited in claim 9 wherein said means for reading is a microprocessor, said means being programmed to compute horizontal measurements of the centers of the patient's pupils from the counts read said second, fourth, sixth and eighth latches.

11. In an ophthalmological instrument for examination of pupillary responses and extrinsic eye muscle balance including pupil imaging optics and a video camera having a photosensitive image plane on which images of a patient's pupils are focused by the pupil imaging optics, pupil tracking apparatus comprising:

an analog comparator connected to receive a video output signal from said video camera, said comparator providing an output when one of said patient's pupils is detected during a horizontal scan by said video camera;

a first counter responsive to the output of said comparator for counting clock pulses during said comparator output to provide a measure of a chord of the patient's pupil;

a first latch temporarily storing a count in said counter;

a digital comparator connected to said first latch and to said first counter to compare the count in said first counter with a previous count stored in said first latch and storing the count in said counter in said first latch when said count is greater than the count in said first latch;

a second latch connected to said first latch and storing the count of said first latch during a vertical sync pulse of said video camera, the count in said second latch corresponding to a measurement of the pupil diameter;

a second counter for counting clock pulses from a reference point until an output is received from said analog comparator;

a third latch temporarily storing a count in said second counter and responsive to said digital comparator and storing the count in said second counter when the count in said first counter is greater than the count in said first latch;

a fourth latch connected to said third latch and storing the count in said third latch during said vertical sync pulse, said fourth latch storing a count corresponding to a horizontal measurement of a position of an edge of the patient's pupil along said diameter;

a third counter for counting horizontal synchronization pulses from said video camera from a reference point;

a fifth latch temporarily storing a count in said third counter and responsive to said digital comparator and storing the count in said third counter when the count in said first counter is greater than the count in said first latch;

a sixth latch connected to said fifth latch and storing the count in said fifth latch during said vertical sync pulse, said sixth latch storing a count corresponding to a vertical measurement of a position of the center of the patient's pupil;

a microprocessor connected to read said second, fourth and sixth latches, said microprocessor being programmed to compute horizontal measurements of the centers of the patient's pupils from the counts read said second and fourth latches; and horizontal and vertical drive means connected to said pupil imaging optics and responsive to said microprocessor to track a patient's pupil.

12. The pupil tracking apparatus recited in claim 11 further comprising focus drive means connected to said pupil imaging optics and wherein said microprocessor is programmed to maximize a slope of an analog video line from said video camera, said focus drive means being responsive to said microprocessor to focus said pupil imaging optics.

13. In an ophthalmological instrument for examination of pupillary responses and extrinsic eye muscle balance including pupil imaging optics and a video camera having a photosensitive image plane on which images of a patient's pupils are focused by the pupil imaging optics, pupil tracking apparatus comprising:

an analog comparator connected to receive an video output signal from said video camera, said comparator providing an output when one of said patient's pupils is detected during a horizontal scan by said video camera;

a first counter responsive to the output of said comparator for counting clock pulses during said comparator output to provide a measure of a chord of the patient's pupil;

a first latch temporarily storing a count in said first counter;

a first digital comparator connected to said first latch and to said first counter to compare the count in said first counter with a previous count stored in said first latch and storing the count in said first counter in said first latch when said count is greater than the count in said first latch;

a second latch connected to said first latch and storing the count in said first latch during a vertical sync pulse of said video camera, the count in said second latch corresponding to a measurement of the diameter the patient's left pupil;

a third latch temporarily storing a count in said first counter;

a second digital comparator connected to said third latch and to said first counter to compare the count in said first counter with a previous count stored in said third latch and storing the count in said first counter when said count is greater than the count in said third latch;

a fourth latch connected to said third latch and storing the count in said third latch during said vertical sync pulse, the count in said fourth latch corresponding to a measurement of the diameter the patient's right pupil;

a second counter for counting clock pulses from a reference point;

a fifth latch temporarily storing a count in said second counter and responsive to said first digital comparator and storing the count in said second counter when the count in said first counter is greater than the count in said first latch;

a sixth latch connected to said fifth latch and storing the count in said fifth latch during said vertical sync pulse, said sixth latch storing a count corresponding to a horizontal measurement of a position of an edge of the patient's left pupil along said diameter;

a seventh latch temporarily storing a count in said second counter and responsive to said second digital comparator and storing the count in said second counter when the count in said first counter is greater than the count in said third latch;

an eighth latch connected to said seventy latch and storing the count in said seventh latch during said vertical sync pulse, said eighth latch storing a count corresponding to a horizontal measurement of a position of an edge of the patient's right pupil along said diameter;

a third counter for counting horizontal synchronization pulses from said video camera from a reference point;

a ninth latch temporarily storing a count in said third counter and responsive to said first digital comparator and storing the count in said third counter when the count in said first counter is greater than the count in said first latch;

a tenth latch connected to said ninth latch and storing the count in said ninth latch during said vertical sync pulse, said tenth latch storing a count corresponding to a vertical measurement of a position of the center of the patient's left pupil;

an eleventh latch temporarily storing a count in said third counter and responsive to said second digital comparator and storing the count in said third counter when the count in said first counter is greater than the count in said first latch;

a twelfth latch connected to said eleventh latch and storing the count in said eleventh latch during said veritcal sync pulse, said twelfth latch storing a count corresponding to a vertical measurement of a position of the center of the patient's right pupil;

a microprocessor connected to read said second, fourth, sixth, eighth, tenth, and twelfth latches, said microprocessor being programmed to compute horizontal measurements of the centers of the patient's pupils from the counts read said second, fourth, sixth and eighth latches; and horizontal and vertical drive means connected to said pupil imaging optics and responsive to said microprocessor to independently track the patient's left and right pupils.

14. The pupil tracking apparatus recited in claim 13 further comprising focus drive means connected to said pupil imaging optics and wherein said microprocessor is programmed to maximize a slope of an analog video line from said video camera, said focus drive means being responsive to said microprocessor to independently focus said pupil imaging optics for each of said left and right pupils.

* * * * *